United States Patent [19]

Hara et al.

[11] Patent Number: 5,233,035
[45] Date of Patent: Aug. 3, 1993

[54] CEPHALOSPORIN DERIVATIVES

[75] Inventors: Ryuichiro Hara, Tokyo; Noriaki Nagano, Ibaraki; Hideki Anan, Ibaraki; Tokuo Koide, Ibaraki; Ei-ichi Nakai, Tokyo; Masaki Yokota, Ibaraki; Katsuhiko Hamaguchi, Tokyo; Masato Sato; Toru Yoden, both of Ibaraki; Tetsuya Maeda, Saitama, all of Japan

[73] Assignee: Yamanouchi Pharmaceutical Co., Ltd., Tokyo, Japan

[21] Appl. No.: 860,306

[22] Filed: Mar. 27, 1992

Related U.S. Application Data

[63] Continuation of Ser. No. 586,262, Sep. 19, 1990, abandoned.

[30] Foreign Application Priority Data

Sep. 26, 1989 [JP] Japan .................................. 1-249713
Dec. 27, 1989 [JP] Japan .................................. 1-344677
Jan. 29, 1990 [JP] Japan .................................. 2-18668
Feb. 2, 1990 [JP] Japan .................................. 2-24057

[51] Int. Cl.$^5$ ................. C07D 501/36; A61K 31/545
[52] U.S. Cl. ................................. 540/227; 540/226; 540/225
[58] Field of Search ............... 540/227, 222, 225, 221; 514/206, 202, 203

[56] References Cited

U.S. PATENT DOCUMENTS 4,840,945  7/1984  Ohnishi et al. ...................... 540/227

Primary Examiner—Nicholas S. Rizzo
Attorney, Agent, or Firm—Burgess, Ryan & Wayne

[57] ABSTRACT

A cephalosporin compound represented by the general formula:

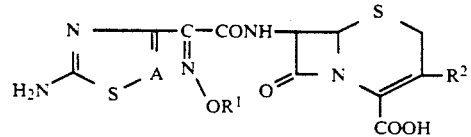

This compound exhibits a high antimicrobial activity.

2 Claims, No Drawings

CEPHALOSPORIN DERIVATIVES

This application is a continuation of application Ser. No. 586,262, filed Sep. 21, 1990 now abandoned.

BACKGROUND OF THE INVENTION

1. Field of the Invention

The present invention relates to cephalosporin compounds represented by the general formual (I) and salts thereof and to processes producing them

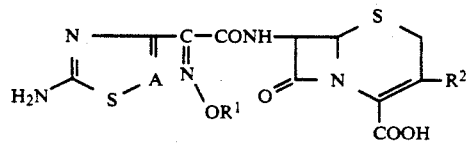

wherein A represents CH or N; $R^1$ is a group represented by

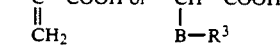

(wherein B is a single bond or a sulfur atom; and $R^3$ is lower alkyl, pyridyl, thienyl, or a group of the formula

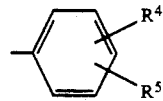

(wherein $R^4$ and $R^5$ represent hydrogen atom or hydroxyl which may be protected)); $R^2$ represents

or $-X-R^6$ (wherein X represents $-CH_2O-$, $-CH_2-S-$, $-CH=CH-$ or $-CH=CH-S-$; $R^6$ represents

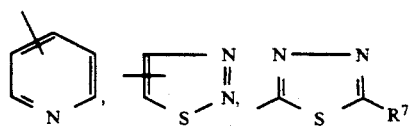

(wherein $R^7$ is hydrogen or lower alkyl),

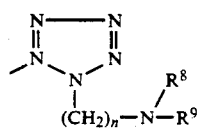

(wherein n is an integer of 1 to 5; $R^8$ and $R^9$ represent hydrogen or lower alkyl),

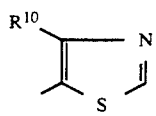

(wherein $R^{10}$ is hydrogen or lower alkyl),

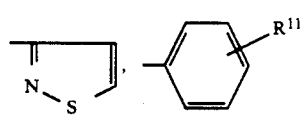

(wherein $R^{11}$ is hydrogen, halogen, hydroxyl or lower alkoxy),

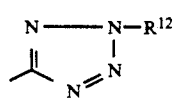

(wherein $R^{12}$ is hydrogen or lower alkyl), or

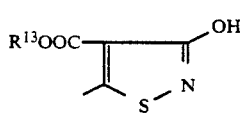

(wherein $R^{13}$ is hydrogen or a protective group for carboxyl) with the proviso that the following case is excluded A is CH, X is $-CH_2-S-$, $R^3$ is

B is a single bond, in combination.

2. Description of the Related Art (Prior Art and Subject to be Solved by the Invention)

The compounds of the present invention have antibacterial activity against a wide range of pathogens (gram positive and negative bacteria), and, in particular, show superior antibacterial activity against *Pseudomonas aeruginosa*.

According to the state of the art, are known many cephalosporin compounds having specific substituents at the 3- and 7- positions, as described in, for example, EP 197, 409.

SUMMARY OF THE INVENTION

The present invention provides cephalosporin compounds having the characteristics that (a) the substituent at the 3-position is a heterocyclicvinyl group, a heterocyclicthiovinyl group or an aryloxymethyl group, and the substituent at the 7-position is an acetamido group substituted by [(carboxy) (aryl) methoxy]imino, or (b) the substituent at the 3-position is a specific heterocyclicthiomethyl group and the substituent at the 7-position is an acetamido group substituted by [(carboxy) (arylthio or lower alkylthio or heteroaryl)methoxy]imino. Thus, the structure of the present compounds differ from that of prior art compounds.

DESCRIPTION OF THE PREFERRED EMBODIMENTS

Means for Solving the Problems

In the present specification, the group represented by the formula:

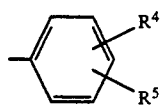

is, for example, phenyl, phenyl substituted by one or two hydroxyl(s), or phenyl substituted by one or two protected-hydroxyl(s). The hydroxyl(s) or protected hydroxyl(s) may be present at any position of the phenyl group. The protective groups for the protected hydroxyl are, for example, lower acyl, lower alkoxycarbonyl, lower alkylsilyloxy.

When the protected hydroxyls exist, each other, at the adjacent position, both protective groups may form a ring together. Typical groups for such groups are dimethylsilyldioxy, oxalyl, etc.

The term "lower" in the present specification means a straight or branched carbon chain having 1 to 6 carbon atoms. Thus examples of the "lower alkyl" are methyl, ethyl, propyl, butyl, pentyl, hexyl, isobutyl, tert-butyl, isopropyl, etc.; and examples of the "lower acyl" are formyl, acetyl, propionyl, butanoyl, iso-butanoyl, veleryl, iso-valeryl, hexanoyl, etc.; and examples of the "lower alkoxy" are methoxy, ethoxy, propoxy, butoxy, pentyloxy, hexyloxy, iso-butoxy, tert-butoxy, isopropoxy, etc.

"Halogen" for the definition of $R^{11}$ is, for example, fluorine, chlorine, bromine or iodine. Examples of "protective groups for carboxy" in the definition of $R^{13}$ are tri(lower)alkylsilyl such as trimethylsilyl, benzhydryl, beta-methylsulfonylethyl, phenacyl, p-methoxybenzyl, tert-butyl, p-nitrobenzyl, etc.

The salts of the compounds of the present invention of formula I are the pharmacologically acceptable nontoxic salts of the compounds such as nontoxic acid addition salts or base addition salts. As the salts with acids, there may be mentioned inorganic acid salts such as hydrochloric acid salts, sulfate, phosphate etc. and salts with organic acids such as acetates, lactate, tartrate, fumarate, maleates, methanesulfonates, ethanesulfonates, etc.; further, as the salts with the bases, there are alkali metal salts such as sodium salt, potassium salt, alkaline earth metal salts such as calcium salts, magnesium salts, and salts with organic bases and basic amino acids such as ammonium, teimethylamine, triethylamine, cyclohexylamine, dicylcohexylamine, diethanolamine, arginine, lysine etc.

The compounds of this invention of formula (I) have an asymmetric carbon atom, an iminoether type oxime portion and 2-aminothiazoyl group; thus the compounds of this invention include optical isomers, geometrical isomers and tautomers. When the substituent at the 3-position include a vinyl group, there exist geometrical isomers such as cis(Z), trans(E). The invention includes all these R and S optical isomers, all these Z-form and E-form geometrical isomers and mutual tautomers (according to the 7-position substituent) alone and in any combination, and also includes all these Z-form and E-form geometrical isomers (according to the 3-position substituent) alone and in any combination.

The compounds of the present invention may be produced by various processes. Typical production processes are shown below.

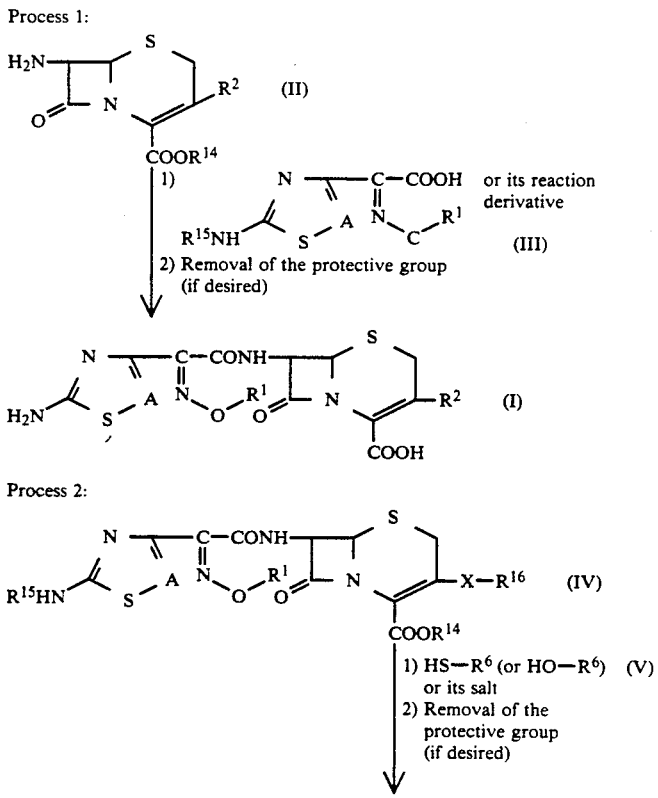

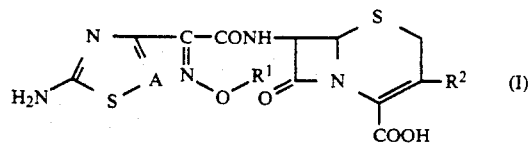

(I)

Process 3:

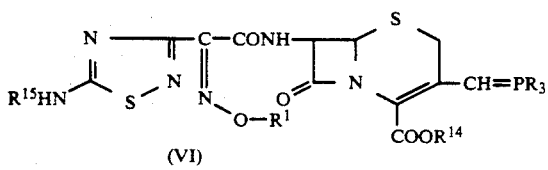

(VI)

1) OHC—R⁶ (VIII)
2) Removal of the protective group (if desired)

1) (R¹⁷)₃P=CH—R⁶ (IX)
2) Removal of the protective group (if desired)

(VII)

(Iₐ)

(In the above formulas, A, $R^1$, $R^2$ and $R^6$ have the same significances as defined before; $R^{15}$ represents a protective group for the amino group; $R^{14}$ represents a protective group for the carboxyl group; $R^{16}$ represents a halogen atom, a lower acyloxy group or a substituted sulfoxy group; and $R^{17}$ represents a phenyl group.)

As the halogen atom in the definition of $R^{16}$, there may be mentioned, for example, a chlorine atom, a bromine atom, a iodine atom, etc. As the lower acyloxy group, there may be mentioned, for example, an acectoacetoxy group, an acetoxy group, a propionyloxy group, an isopropionyloxy group, a butyryloxy group, an iso-butyryloxy group, a valeryloxy group, etc. As the substituted sulfonyloxy group, there may be mentioned for example, a lower alkylsulfonyloxy group, a trichlorosulfonyloxy group or a phenyl group which may unsubstituted or substituted by halogen, lower alkyl or nitro.

As the protective group for the carboxyl group in the definition of $R^{14}$, there may be mentioned, for example, an tri(lower)alkylsilyl group such as trimethylsilyl, an benzhydryl group, a beta-methylsulfonylethyl group, a phenacyl group, a p-methoxybenzyl group, tert-butyl group, p-nitrobenzyl group (that is, protective groups which may be removed easily under mild conditions).

The protective group for the amino group in the definition of $R^{15}$ is a protective group which may be removed easily under mild conditions. Practical examples of such protective group are a tri(lower)alkylsilyl group such as trimethylsilyl, a formyl group, an acetyl group, a propionyl group, a tert-butoxycarbonyl group, a methoxyacetyl group, a methoxypropionyl group, a benzyloxycarbonyl group, a p-nitrobenzyloxycarbonyl group (acyl type protective groups), a benzyl group, a benzhydryl group, trityl group (aralkyl type protective groups) etc. and the like.

Process 1:

The compounds (I) of the present invention may be produced by a 7-amino-3-substituted-methyl (or vinyl)-3-cephem-4-carboxylate derivative represented by the general formula (II) or its salt with α-(thiazol)-α-substituted-iminoacetic acid represented by the general formula (III) or a reactive derivative thereof, and if desired, removing the protective group(s).

The reaction of the formula (II) compound with the formula (III) compound or its reactive derivative is generally conducted in a solvent with cooling or at room temperature. The solvent is not particularly restricted as long as it does not participate in the reaction, but as those generally employed, there may be mentioned acetone, dioxane, ether, tetrahydrofuran, methyl ethyl ketone, chloroform, dichloroethane, dichloromethane (methylene chloride), ethyl acetate, ethyl formate, dimethylformamide, dimethylsulfoxide, water, etc. These solvents may also be used by appropriately mixing.

The compound (III) may be used in the reaction not only as the state of a free carboxylic acid but also as a reactive derivative of the carboxylic acid. Those suitable are activated esters (for example, benzotriazole esters), mixed acid anhydrides, acid halides, activated amides, acid anhydrides, acid azides etc. When the compound (III) is used in the state of a free carboxylic acid, it is preferred to use a condensing agent such as N, N'-dicyclohexylcarbodiimide, N,N'-diehtylcarbodiimide etc.

Further, depending on the kind of the reactive derivative of the carboxylic acid used, there is such case that is preferred for smoothly proceeding the reaction to react in the presence of a base. As this base, there may be mentioned inorganic bases such as sodium bicarbonate, potassium bicarbonate, sodium carbonate, potassium carbonate etc., and organic bases such as trimethylamine, triethylamine, dimethylaniline, pyridine, etc.

The removal of the protective group from the thus obtained product may be easily effected, for example, by contacting with water in the case of the protective group being tri(lower alkyl)silyl, or by using an acid such as formic acid, trifluoroacetic acid, a trifluoroacetic acid-anisole mixture, a a hydrobromic acid-acetic acid mixture, a hydrochloric acid-dioxane mixture etc. in the case of the protective group being benzhydryl, p-methoxybenzyl, trityl, tert-butyl, formyl etc.

Further, the removal of the protective group for the hydroxyl group (for example, lower acyl and other easily removable groups) may be effected by solvolysis using an aqueous solvent containing a base such as sodium bicarbonate, sodium carbonate, ammonium hydroxide, ammonium carbonate or ammonium carbamate etc.

Process 2

The formula (I) compound of the present invention may be produced by reacting a cephalosporin compound of the formula (IV) or its salt with a mercapto compound (or alcohol compound) of the formula (V) or its salt, and, if desired, removing the protective group(s) in the product.

The reaction is generally conducted in a solvent such as water, phosphate buffer, organic solvent (for example, dimethylsulfoxide, dimethylformamide, nitrobenzene, acetone, chloroform, dichloromethane, dichloroethane, methanol, ethanol, ether, dioxane, tetrahydrofuran etc.), a mixed solvent of hydrophilic organic solvent and water. For a smoothly proceeding reaction, there may be added a base or various kinds of salt. As this base, there may be mentioned inorganic bases such as sodium hydroxide, potassium hydroxide, sodium carbonate, potassium carbonate, etc. and organic bases such as trialkylamine, etc. As the salt, there may be mentioned quarternary ammonium salt such as tetraalkylammonium salt. The reaction may easily procced with ice-cooling or at room temperature. The removal of the protective group(s) in the product may be effected in the same way as described in the above Process 1.

Process 3

The formula ($I_a$) compound of the present invention may be produced by reacting an aldehyde compound of the formula (VII) or (VIII) with a Wittig reagent represented by the formula (VI) or (IX) or its reactive derivative. As the reactions using a reagent equivalent to the Wittig reagent, there may be mentioned Horner-Emmons reaction, Peterson reaction, Julia's olefine synthesis reaction.

The solvent is not particularly restricted as long as it does not participate in the reaction, but as those generally employed, there may be mentioned methylene chloride, diethyl ether, tetrahydrofuran, dimethylformamide, dimethylsulfoxide, etc.

The formed C—C double bond may be in the form of cis or trans, and, if desired, it is possible to produce separately. For example, if a stable ylide compound is used as the Wittig reagent ($III_a$) or if LiBr is added in the reaction system, a trans-form compound can be obtained preferentially; and, if the removal of silicon atom is effected under acidic condition or basic condition, it is possible to porduce cis-form or trans-form separately. Further, it is also possible to isolate the crystal for only one among the both forms, if an appropriate solvent is added to the cis-trans mixture obtained after the reaction.

It is preferable to use the compound (VI) or (VII) in an amount equimolar or excess of the compound (VIII) or (IV). The reaction can be conducted with cooling, at room temperature or with heating depending on the kind of C—C double bond forming reaction used, but usually at room temperature or with cooling.

Production processes for the formula (I) compounds of the present invention are not particularly reastricted to the above-mentioned processes, and, any other production processes known can be used for the production of the present compounds.

The salts of the compounds of the present invention represented by the general formula (I) may be produced by the production by previously using the salt of the starting material in the above-described production process, or by applying a salt-forming reaction conventionally employed in this field to the free compound produced by the above-described process.

For example, an alkali metal salt can be produced by adding a n-butanol solution of alkali 2-ethylhexanoate followed by the addition of an organic solvent(s) which has different solubility, such as ether, ethyl acetate etc.; an organic base salt or a basic amino acid salt can be produced by adding equivalent amount or a little excess amount of an organic base or a basic amino acid such as dicylcohexylamine, triethylamine, cyclohexylamine, diethanolamine, arginine, lysine etc. ect; and an ammonium salt can be produced by adding aqueous ammonia.

Isolation and purification of the compounds of the present invention (I) or salts thereof may be conducted in the conventional manner, and separation and purification by extraction with organic solvents, crystallization, column chromatography etc. are employed.

The compounds of the present invention (I) exhibit a high antimicrobial activity against a wide range of pathogens including gram positive bacteria and gram negative bacteria. In particular, they show markedly superior antibacterial activity against *Pseudomonas aeruginosa*.

The antimicrobial activity of the compounds of the present invention is shown in the following Table.

TABLE

| Name of Strain | (Minimum Growth Inhibition Concentration) Example No. | | | | | | | | |
| --- | --- | --- | --- | --- | --- | --- | --- | --- | --- |
| | 1 | 2 | 5 | 7 | 13 | 15 | 19 | 23 | 29 |
| S. aureus FDA209P JC-1 | 12.5 | 25 | 6.25 | 50 | 0.78 | 0.78 | 25 | 0.78 | 0.78 |
| E. Coli O-1 | 0.05 | 0.025 | 0.1 | 0.1 | 0.05 | 0.05 | 0.025 | 0.1 | 0.05 |
| C. freundii NIH 10018-68 | 0.05 | — | 0.1 | 0.1 | 0.05 | 0.05 | 0.013 | 0.05 | 0.1 |
| P. mirabilis IFO OM-9 | ≦0.006 | ≦0.006 | 0.025 | ≦0.006 | 0.025 | 0.025 | ≦0.006 | 0.05 | 0.025 |

TABLE-continued

| | (Minimum Growth Inhibition Concentration) | | | | | | | |
|---|---|---|---|---|---|---|---|---|
| | Example No. | | | | | | | |
| Name of Strain | 1 | 2 | 5 | 7 | 13 | 15 | 19 | 23 | 29 |
| P. aeruginosa NCTC 10490 | 0.05 | 0.05 | ≦0.006 | 0.1 | 0.2 | 0.1 | 0.05 | 0.05 | 0.1 |

The preparation of the respective formulations containing the compound of the present invention as an active ingredient may be effected in the conventional manner by adding excipients, preservatives, stabilizers etc. employed in the pharmaceutical field.

The compounds of the present invention or salts thereof are orally administered as tablets, pills, capsules, granules etc., or parenterally as injections such as intravenous injections, intramuscular injection, suppository etc. The dosage varies depending on the severity graveness of the condition, the age, sex etc. of the patients, etc., and is 200–4,000 mg per day for adults, and this is administered in 1 to 4 portions.

Then, the production process of this invention will be further desribed in the following examples.

REFERENCE EXAMPLE 1

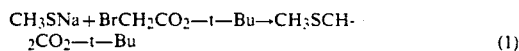
(1)

Under ice cooling, 33.4 g of tert-butyl bromoacetate was gradually added to 80.0 g of 15% sodium methylmercaptan aqueous solution and the resulting mixture was reacted at room temperature overnight. After completion of the reaction, the reaction mixture was extracted 4 times with ethyl acetate and the extract was washed with saturated sodium chloride aqueous solution. After the ethyl acetate layer was dried over magnesium sulfate, ethyl acetate was distilled off to give 26.8 g of crude tert-butyl (methylthio)acetate.

Nuclear magnetic resonance spectrum (in $CDCl_3$) $\delta$ (ppm): 1.50 (9H, s), 2.20 (3H, s), 3.10 (2H,s).

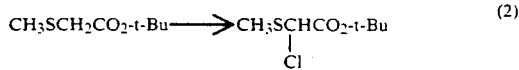
(2)

After 15.2 g of tert-butyl (methylthio)acetate obtained in (1) was dissolved in 100 ml of carbon tetrachloride, 14.9 g of N-chlorosuccinimide was gradually added to the solution under ice cooling. The mixture was stirred at room temperature for 6 hours. After insoluble matters were filtered off, carbon tetrachloride was removed by distillation to give 20.3 g of crude tert-butyl 2-chloro-2-(methylthio)acetate.

Nuclear magnetic resonance spectrum (in $CDCl_3$) $\delta$ (ppm): 1.50 (9H, s) 2.30 (3H, s), 5.28 (1H, s).

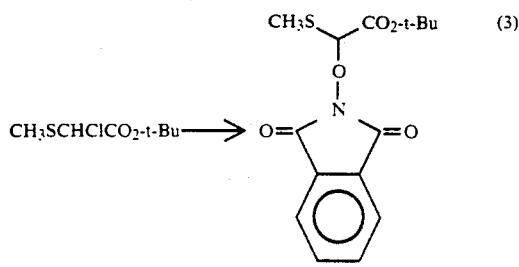
(3)

After 15.3 g of N-hydroxyphthalimide was dissolved in 90 ml of dimethylformamide, 14.3 ml of triethylamine was dropwise added to the solution under ice cooling. Then, 20.3 g of tert-butyl 2-chloro-2-(methylthio)acetate obtained in (2) was dropwise added to the mixture followed by stirring at room temperature for 3 hours and a half. After ethyl acetate was added to the reaction mixture, the resulting mixture was washed with water and then with saturated sodium chloride aqueous solution. After the organic phase was dried over magnesium sulfate, the solvent was distilled off to give 32.4 g of crude tert-butyl 2-(methylthio)-2-phthalimidoxyacetate.

Nuclear magnetic resonance spectrum (in $CDCl_3$) $\delta$ (ppm): 1.51 (9H, s), 2.35 (3H, s), 5.65 (1H, s) 7.5–8.0 (4H, m).

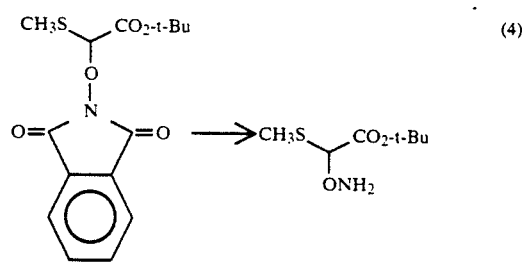
(4)

After 32.4 g of tert-butyl 2-(methylthio)-2-phthalimidoxyacetate obtained in (3) was dissolved in 370 ml of methylene chloride, 9.5 ml of hydrazine monohydrate was dropwise added to the solution at room temperature. After stirring for 2 hours, 300 ml of 10% ammonia water was added to the reaction mixture followed by extracting 3 times with methylene chloride. After washing with saturated sodium chloride aqueous solution, the methylene chloride layer was dried over anhydrous magnesium sulfate. Methylene chloride was distilled off to give 15.9 g of crude tert-butyl 2-aminooxy-2-(methylthio)acetate.

Nuclear magnetic resonance spectrum (in $CDCl_3$) $\delta$ (ppm: 1.51 (9H, s), 2.15 (3H, s), 4.97 (1H, s).

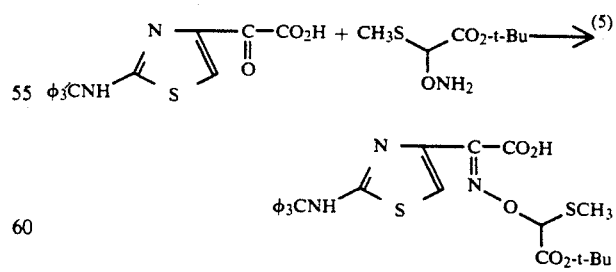
(5)

After 3.00 g of 2-(2-tritylaminothiazol-4-yl)-2-oxoacetic acid was dissolved in 250 ml of methanol, a solution of 3.00 g of tert-butyl 2-aminooxy-2-(methylthio)acetate obtained in (4) in 100 ml of methanol was dropwise added to the former solution. After stirring at room temperature for an hour and a half, the solvent was distilled off to give 9.23 g of crude (Z)-2-(2-tritylamino-4-thiazolyl)-2-[[(tert-butoxycarbonyl)(methylthio)methoxy]imino]acetic acid.

Infrared absorption spectrum $\nu_{max}^{KBr}$: 3072, 1740, 1678, 1598, 1540, 1152, 702.

Nuclear magnetic resonance spectrum (in DMSO-$d_6$) δ (ppm): 1.42 (9H, s), 2.10 (3H, s), 5.54 (1H, s), 6.88 (1H, s), 7.0–7.6 (15H, m).

EXAMPLE 1

2-(2-tritylamino-4-thiazolyl)-2-[[(R S)-(tert-butoxycarbonyl)(methylthio)methoxy]imino]acetamido]-3-chloromethyl-3-cephem-4-carboxylate.

Nuclear magnetic resonance spectrum (in DMSO-$d_6$) δ (ppm): 1.42 (9H, s, t-Bu), 2.11, 2.13 (3H, s each, S$\underline{CH}_3$), 3.2–3.8 (2H, m, $\underline{CH}_2$ at the 2-position), 3.74 (s, 3H, O$\underline{CH}_3$), 4.44, 4.55 ($\overline{2H}$, AB pattern, —$\underline{CH}_2$Cl), 5.1–5.3 ($\overline{1H}$, C$\underline{H}$SCH$_3$), 5.27 (2H, s,

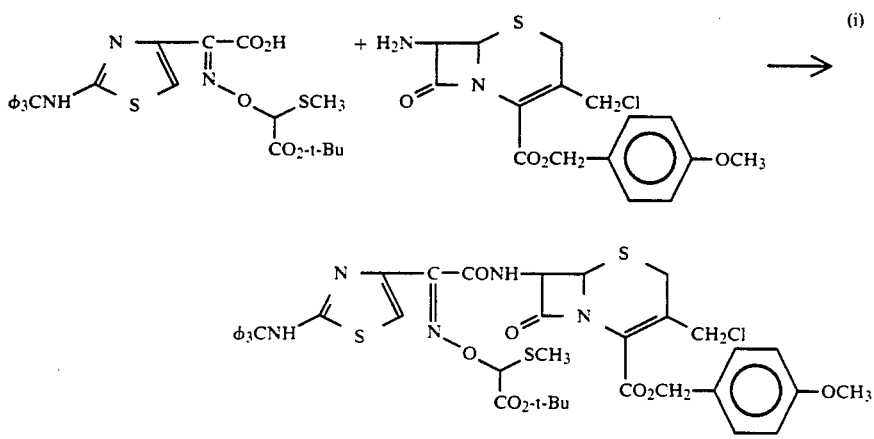

After 2.20 g of (Z)-2-(2-tritylamino-4-thiazolyl)-2-[[(tert-butoxycarbonyl)(methylthio)methoxy]imino]acetic acid was dissolved in 20 ml of methylene chloride, 776 mg of phosphorus pentachloride was added to the solution under ice cooling. The mixture was stirred for 15 minutes under ice cooling to give a solution of the acid chloride in methylene chloride. On the other hand, 3.19 g of p-methoxybenzyl 7-amino-3-chloromethyl-3-cephem-4-carboxylate was dissolved in 20 ml of methylene chloride and, 1.66 ml of pyridine was added to the solution at −40° C. The solution of the acid chloride in methylene chloride previously prepared was added to the resulting solution at −40° C. After stirring for 10 minutes, the temperature was elevated to −20° C. and, 40 ml of ice water and 6 ml of 1N-HCl aqueous solution were added to the reaction mixture. The mixture was extracted 3 times with ethyl acetate. After the organic phase was washed with saturated sodium chloride aqueous solution and dried over anhydrous sodium sulfate, the solvent was distilled off to give 5.12 g of caramel. This caramel was subjected to silica gel column chromatography and the column was eluted with benzene-ethyl acetate to give 1.37 g of p-methoxybenzyl 7β-[(Z)-

—CH$_2$—⟨⟩—OCH$_3$), 5.45 (1H, d, C$\underline{H}$ at the 6-position), 5.68–5.78 (1H, m, C$\underline{H}$ at the 7-position), 6.74 (1H, s, ⟨thiazole⟩ ), 6.9–7.5 (19H, m,

—CH$_2$—⟨(H)(H)⟩—OCH$_3$,

Tr), 9.60, 9.64 (1H, d each, CON$\underline{H}$).

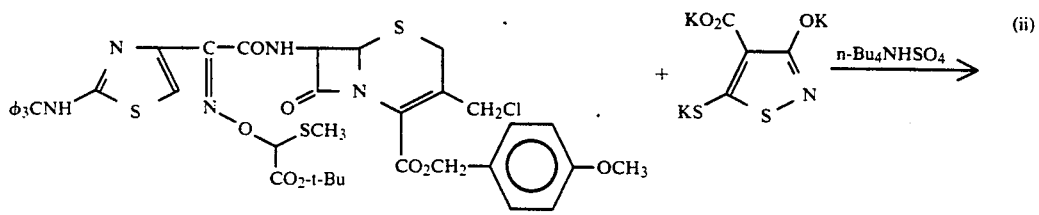

-continued

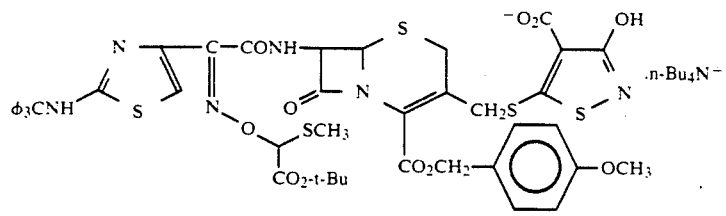

After 848 mg of 5-mercapto-4-carboxy-3-hydroxyisothiazole tripostassium salt was dissolved in 10 ml of water, 10 ml of methylene chloride, 1.98 g of tetra-n-butylammonium hydrogensulfate and 2.28 g of p-methoxybenzyl 7β-[(Z)-2-tritylamino-4-thiazolyl)-2-[[(R S)-(tert-butoxycarbonyl)(methylthio)methoxy]imino]acetamido]-3-chloromethyl-3-cephem-4-carboxylate obtained in (i) were added to the solution at room temperature. After stirring at room temperature overnight, the methylene chloride phase was washed with 4 ml of 1N-HCl aqueous solution, 6 ml of water and then 6 ml of saturated sodium chloride aqueous solution. After drying over anhydrous sodium sulfate, the solvent was distilled off to give 3.65 g of caramel. This caramel was subjected to silica gel column chromatography and the column was eluted with chloroform-methanol to give 1.98 g of p-methoxybenzyl 7β-[(Z)-2-(2-tritylamino-4-thiazolyl)-2-[[(R S)-(tert-butoxycarbonyl)(methylthio)methoxy]imino]acetamido]-3-cephem-4-carboxylate tetra-n-butylammonium salt.

Nuclear magnetic resonance spectrum (in DMSO-d6) δ (ppm): 1.4 (9H, s, t-Bu), 2.11, 2.13 (3H, s each, SCH3), 3.2-3.8 (2H, m, CH2 at the 2-position), 3.74 (s, 3H, OCH3), 3.8-4.3 (2H, AB pattern, —CH2S—), 5.1-5.3 (1H, CHSCH3), 5.27 (2H, s,

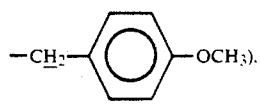

5.41 (1H, d, CH at the 6-position), 5.5-5.8 (1H, m, CH at the 7-position), 6.72 (1H, s,

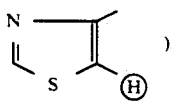

6.9-7.5 (19H, m,

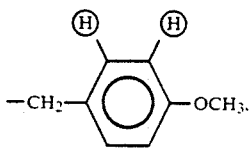

Tr), 9.60, 9.64 (1H, d each, CONH)

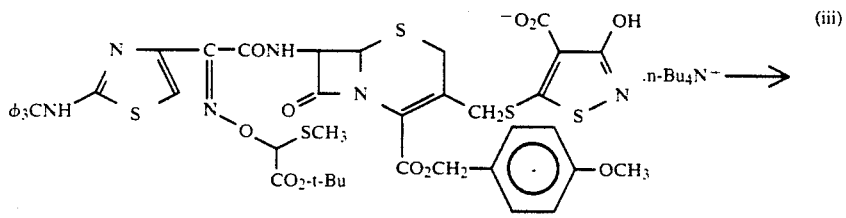

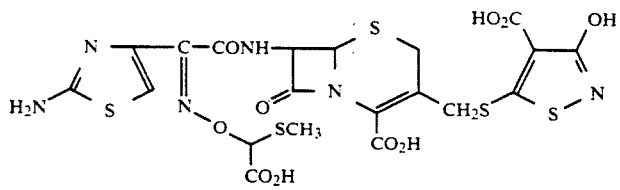

After 1.98 g of p-methoxybenzyl 7β-[(Z)-2-(2-tritylamino-4-thiazolyl)-2-[[(R S)-(tert-butoxycarbonyl)(methylthio)methoxy]imino]acetamido]-3-[[(4-carboxy-3-hydroxy-5-isothiazolyl)thio]methyl]-3-cephem-4-carboxylate tetra-n-butylammonium salt obtained in (ii) was dissolved in 10 ml of methylene chloride and 1 ml of anisole, 5 ml of trifluoroacetic acid was dropwise added to the solution under ice cooling. The mixture was then stirred at room temperature for an hour. Trifluoroacetic acid and methylene chloride were distilled off under reduced pressure ethyl ether was added to the residue to form powders. The powders obtained by filtration were further suspended in 6 ml of water. Under ice cooling, 9 ml of trifluoroacetic acid was added to the suspension. After stirring at room temperature for an hour, trifluoroacetic acid and water were removed by distillation under reduced pressure. Ethyl ether was added to the residue to make powders. By filtration, 550 mg of powders were obtained. After the powders were dissolved in diluted sodium hydrogencarbonate aqueous solution, 1N-HCl aqueous solution was added to the solution to adjust pH to 3. The aqueous solution was adsorbed to DIAION HP20 followed by elution with waster and then methanol-water. The fractions containing the desired product were collected. After concentration, the concentrate was freeze dried to give 152 mg of 7β-[(Z)-2-(2-amino-4-thiazolyl)-2-[[(RS)-(carboxy)(methylthio)methoxy]imino]acetamido]-3-[[(4-carboxy-3-hydroxy-5-isothiazolyl)thio]methyl]-3-cephem-4-carboxylic acid.

Infrared absorption spectrum $\nu_{max}^{KBr}$: 1778.

Nuclear magnetic resonance spectrum (in DMSO-d$_6$) δ (ppm): 2.17, 2.19 (3H, s each, SCH$_3$), 3.56, 3.76 (2H, AB pattern, CH$_2$ at the 2-position), 3.74 (s, 3H, OCH$_3$), 4.12, 4.28 (2H, AB pattern, —CH$_2$S—), 5.17-5.22 (1H, CHSCH$_3$), 5.56 (1H, d, CH at the 6-position), 6.77, 6.79 (1H, s each,

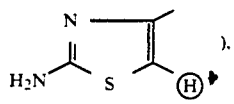

), 9.59, 9.65 (1H, d each, CONH).

REFERENCE EXAMPLE 2

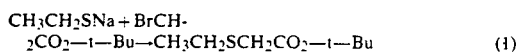  (1)

Under ice cooling, 4.6 ml of ethyl mercaptan was added to 62 ml of 1N-NaOH aqueous solution followed by stirring for 30 minutes. Furthermore, 10.1 ml of tert-butyl bromoacetate was gradually added to the mixture under ice cooling and the resulting mixture was reacted at room temperature for 3 hours. After completion of the reaction, the reaction mixture was extracted 4 times with ethyl acetate and the extract was washed with saturated sodium chloride aqueous solution. After the ethyl acetate layer was dried over magnesium sulfate, ethyl acetate was distilled off to give 12.0 g of crude tert-butyl (ethylthio)acetate.

Infrared absorption spectrum $\nu_{max}^{KBr}$ (cm$^{-1}$): 3608, 1732, 1294, 1132.

Mass spectrum EI: 176.

Nuclear magnetic resonance spectrum (in CDCl$_3$) δ (ppm): 1.28 (3H, t), 1.50 (9H, s), 2.68 (2H, q), 3.16 (2H, s).

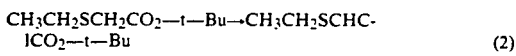  (2)

After 11.9 g of tert-butyl (ethylthio)acetate obtained in (1) was dissolved in 100 ml of carbon tetrachloride, 10.4 of N-chlorosuccinimide was gradually added to the solution under ice cooling. The mixture was stirred at room temperature for 6 hours. After the insoluble materials insoluble matters were filtered off, carbon tetrachloride was removed by distillation to give 15.4 g of crude tert-butyl 2-chloro-2-(ethylthio)acetate.

Infrared absorption spectrum $\nu_{max}^{KBr}$ (cm$^{-1}$): 1746, 1144.

Mass spectrum EI: 210.

Nuclear magnetic resonance spectrum (in CDCl$_3$) δ (ppm): 1.35 (3H, t), 1.50 (9H, s), 2.80 (2H, q), 5.32 (1H, s).

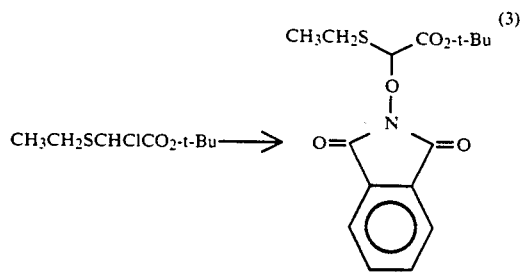

After 11. 1 g of N-hydroxyphthalimide was dissolved in 70 ml of dimethylformamide, 11.0 ml of trietylamine was dropwise added to the solution under ice cooling. Then, 15.1 g of tert-butyl 2-chloro-2-(ethylthio)acetate obtained in (2) was dropwise added to the mixture followed by stirring at room temperature for 3 hours and a half. After ethyl acetate was added to the reaction mixture, the resulting mixture was washed with water and then with saturated sodium chloride aqueous solution. After the organic phase was dried over magnesium sulfate, the solvent was distilled off to give 19.6 g of crude tert-butyl 2-(ethylthio)-2-phthalimidoxyacetate.

Infrared absorption spectrum $\nu_{max}^{KBr}$ (cm$^{-1}$):1740.

Mass spectrum FAB (Pos.): 338.

Nuclear magnetic resonance spectrum (in CDCl$_3$) δ (ppm): 1.28 (3H, t), 1.52 (9H, s), 2.95 (2H, q), 5.63 (1H, s), 7.6-8.0 (4H, m).

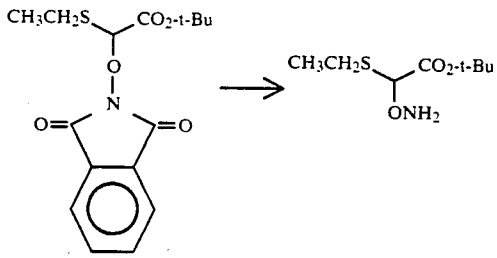

After 19.5 g of tert-butyl 2-(ethylthio)-2-phthalimidoxyacetate obtained in (3) was dissolved in 160 ml of methylene chloride, 3.1 ml of methyl hydrazine was dropwise added to the solution. The temperature was then elevated to 0° C. After stirring for an hour, insoluble matters were removed by filtration. Methylene chloride was distilled off to give 12.7 g of the crude product. The crude product was subjected to silica gel column chromatography and the column was eluted with hexane-ethyl acetate to give 9.34 g of tert-butyl 2-aminooxy-2-(ethylthio)acetate.

Infrared absorption spectrum $\nu_{max}^{KBr}$ (cm$^{-1}$): 2992, 1740, 1154.

Mass spectrum FAB (Pos.): 208.

Nuclear magnetic resonance spectrum (in CDCl$_3$) δ (ppm): 1.29 (3H, t), 1.58 (9H, s), 2.71 (2H, d, q), 5.04 (1H, s), 5.0 (2H, brs).

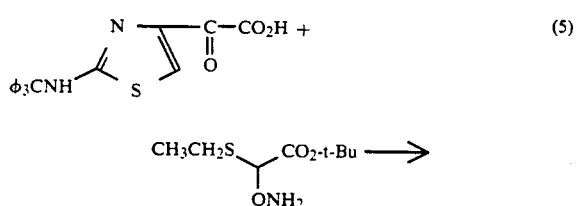  (5)

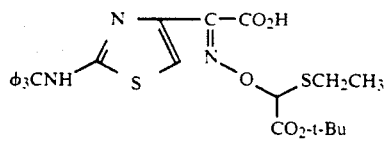

After 18.5 g of 2-(2-tritylaminothiazol-4-yl-2-oxoacetic acid was dissolved in 200 ml of methanol, 9.27 g of tert-butyl 2-aminooxy-2-(ethylthio)acetate obtained in (4) was dropwise added to the solution. After stirring at room temperature for an hour and a half, the solvent was distilled off to give 25.7 g of crude (Z)-2-(2-tritylamino-4-thiazolyl)-2-[[(tert-butoxycarbonyl)(ethylthio)methoxy]imino]acetic acid.

Infrared absorption spectrum $\nu_{max}^{KBr}$ (cm$^{-1}$): 1746, 1152, 754.

Mass spectrum FAB (Pos.): 604.

Nuclear magnetic resonance spectrum (in CD$_3$OD) δ (ppm): 1.15 (3H, t), 1.38 (9H, s), 2.4–2.9 (2H, m), 5.41 (1H, s), 6.68 (1H, s), 7.0–7.5 (15H, m).

EXAMPLE 2 phase was washed with saturated sodium chloride aqueous solution and dried over anhydrous sodium sulfate, the solvent was distilled off to give 39.4 g of caramel. This caramel was subjected to silica gel column chromatography and the column was eluted with benzene-ethyl acetate to give 15.8 g of p-methoxybenzyl 7β-[(Z)-2-(2-tritylamino-4-thiazolyl)-2-[[(R  S)-(tertbutoxycarbonyl) (ethylthio)methoxy]imino]acetamido]-3-chloromethyl-3-cephem-4-carboxylate.

Infrared absorption spectrum $\nu_{max}^{KBr}$ (cm$^{-1}$);1794.

Mass spectrum FAB (Pos.): 954.

Nuclear magnetic resonance spectrum (in DMSO-d$_6$) δ (ppm): 1.15, 1.16 (3H, t each, SCH$_2$CH$_3$), 1.41 (9H, s, t-Bu), 2.68, 2.71 (2H, s each, SCH$_2$CH$_3$), 3.4–3.8 (2H, m, CH$_2$ at the 2-position), 3.73 (s, 3H, OCH$_3$), 4.44, 4.54 (2H, AB pattern, —CH$_2$Cl), 5.16, 5.23 (2H, AB pattern,

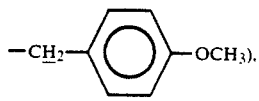

5.1–5.3 (1H, m, CH at the 6-position), 5.46 (1H, m

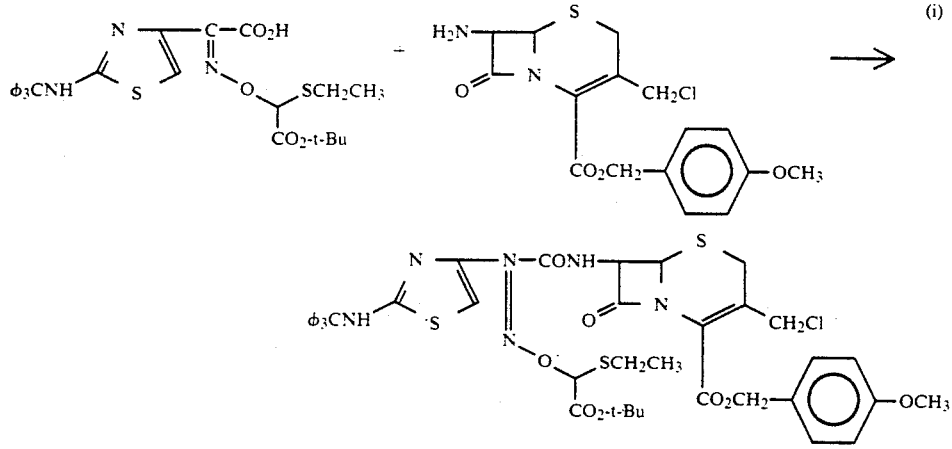

After 14.6 g of (Z)-2-(2-tritylamino-4-thiazolyl)-2-[[(tert-butoxycarbonyl)(ethylthio)methoxy]imino]acetic acid was dissolved in 20 ml of methylene chloride, 5.12 g of phosphorus pentachloride was added to the solution at −20° C. The mixture was stirred for an hour at −20° C. to give a solution of the acid chloride in methylene chloride. On the other hand, 9.81 g of p-methoxybenzyl 7-amino-3-chloromethyl-3-cephem-4-carboxylate hydrochloride was dissolved in 20 ml of methylene chloride and, 6.0 ml of (N,O-bistrimethylsilyl)acetamide was added to the solution. After stirring for 20 minutes, 1.66 ml of pyridine was further added to the mixture at −40° C. The solution of the acid chloride in methylene chloride previously prepared was added to the resulting solution at −60° C. After stirring for 10 minutes, the temperature was elevated to −20° C. and, 40 ml of ice water and 6 ml of 1N-HCl aqueous solution were added to the reaction mixture. The mixture was extracted 3 times with ethyl acetate. After the organic CHSCH$_2$), 5.6–5.8 (1H, m, CH at the 7-position), 6.71, 6.72 (1H, s each,

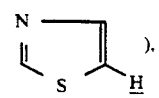

6.8–7.5 (19H, m,

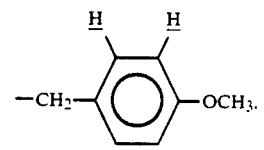

Trityl), 8.84, (1H, s, TrNH), 9.59, 9.62 (1H, d each, CONH).

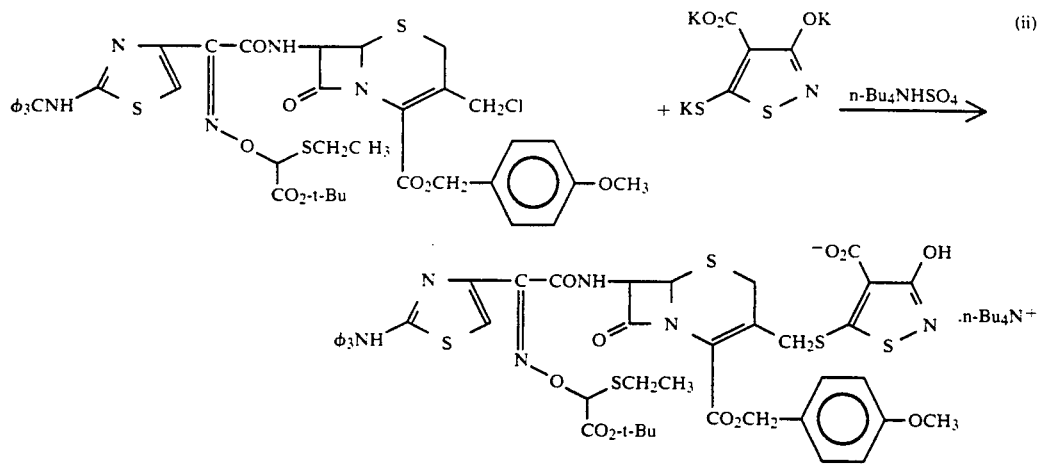

After 1.68 g of 5-mercapto-4-carboxy-3-hydroxyisothiazole tripotassium salt was dissolved in 20 ml of water, 20 ml of methylene chloride, 3.91 g of tetra-n-butylammonium hydrogensulfate and 5.00 g of p-methoxybenzyl 7β-[(Z)-2-(2-tritylamino-4-thiazolyl)-2-[[(R S)-(tert-butoxycarbonyl) (ethylthio)methoxy]-imino]acetamido]-3-chloromethyl-3-cephem-4-carboxylate obtained in (i) were added to the solution at room temperature. After stirring at room temperature overnight, the methylene chloride phase was washed with 4 ml of 1N-HCl aqueous solution, 6 ml of water and then 6 ml of saturated sodium chloride aqueous solution. After drying over anhydrous sodium sulfate, the solvent was distilled off to give 8.08 g of carmel. This caramel was subjected to silica gel column chromatography and the column was eluted with chloroform-methanol to give 5.16 g of p-methoxybenzyl 7β-[(Z)-2-(2-tritylamino-4-thiazolyl)-2-[[(R S)-)tertbutoxycarbonyl) (ethylthio)methoxy]imino]acetamido]-3-[[(4-carboxy-3-hydroxy-5-isothiazolyl)thio]methyl]-3-cephem-4-carboxylate tetra-n-butylammonium salt.

Infrared absorption spectrum $\nu_{max}^{KBr}$ (cm$^{-1}$): 1792.
Mass spectrum FAB (Neg.): 1093.
Nuclear magnetic resonance spectrum (in DMSO-d$_6$) δ (ppm) 0.92 (12H, t, N(CH$_2$CH$_2$CH$_2$CH$\underline{H}$$_3$)$_4$), 1.1–1.7 (16H, m, N(CH$_2$C$\underline{H}$$_2$C$\underline{H}$$_2$CH$_3$)$_4$), 1.15, 1.16 (3H, t each, SCH$_2$C$\underline{H}$$_3$), 1.41 (9H, s, t-Bu), 3.1–3.3 (8H, m, N(C$\underline{H}$$_2$CH$_2$CH$_2$CH$_3$)$_4$), 2.67, 2.70 (2H, q each, SC$\underline{H}$$_2$CH$_3$), 3.4–3.8 (2H, m, C$\underline{H}$$_2$ at the 2-position), 3.73 (s, 3H, OC$\underline{H}$$_3$), 4.44, 4.54 (2H, AB pattern, —C$\underline{H}$$_2$Cl), 5.1–5.3 (3H, m, C$\underline{H}$ at the 6-position, —C$\underline{H}$$_2$—⟨phenyl⟩—OCH$_3$).

5.45 (1H, m C$\underline{H}$SCH$_2$), 5.6–5.8 (1H, m C$\underline{H}$ at the 7-position), 6.73, 6.75 (1H, s each, (thiazolyl ring with H shown).

6.8–7.5 (19H,

—CH$_2$—⟨phenyl with H H⟩—OCH$_3$,

Trityl), 8.82, (1H, s, TrN$\underline{H}$), 9.59, 9.62 (1H, d each, CON$\underline{H}$).

After 5.02 g of p-methoxybenzyl 7β-[(Z)-2-(2-tritylamino-4-thiazolyl)-2-[[(R S)-(tert-butoxycarbonyl)

(ethylthio)methoxy]imino]acetamido]-3-[[(4-carboxy-3-hydroxy-5-isothiazolyl)thio]methyl]-3-cephem-4-carboxylate tetra-n-butylammonium salt obtained in (ii) was dissolved in 20 ml of methylene chloride and 1.5 ml of anisole, 20 ml of trifluoroacetic acid was dropwise added to the solution under ice cooling. The mixture was then stirred at room temperature for an hour. Trifluoroacetic acid and methylene chloride were distilled off under reduced pressure to give the anisole residue. The residue was suspended further in 10 ml of water. Under ice cooling, 20 ml of trifluoroacetic acid was added to the suspension. After stirring at room temperature for an hour, trifluoroacetic acid and water were removed by distillation under reduced pressure. Ethyl ether was added to the residue to make powders. By filtration, 2.86 g of powders were obtained. After the powders were dissolved in diluted sodium hydrogencarbonate aqueous solution, the aqueous solution was adsorbed to DIAION HP20 followed by elution with water and then methanol-water. The fractions containing the desired product were collected. After concentration, the concentrate was freeze dried to give 570 mg of 7β-[(Z)-2-(2-amino-4-thiazolyl)-2-[[(R S)-carboxy)(ethylthio)methoxy]imino]acetamido]-3-[[(4-carboxy-3-hydroxy-5-isothiazolyl)thio]methyl]-3-cephem-4-carboxylic acid trisodium salt.

Infrared absorption spectrum $\nu_{max}^{KBr}$ (cm$^{-1}$): 1776.
Mass spectrum FAB (Neg.): 743.
Nuclear magnetic resonance spectrum (in D$_2$O) δ (ppm): 1.24 (3H, t each, SCH$_2$CH$_3$), 2.70, 2.73 (2H, q each, SCH$_2$CH$_3$), 3.47, 3.79 (2H, AB pattern, CH$_2$ at the 2-position), 3.92, 4.25 (2H, AB pattern, —CH$_2$Cl), 5.20, 5.22 (1H, s each, CHSCH$_2$), 5.64 (1H, d, CH at the 6-position), 5.79, 5.82 (1H, d each, CH at the 7-position). 7.07, 7.08 (1H, s each,

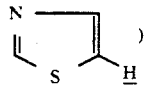
)

EXAMPLE 3

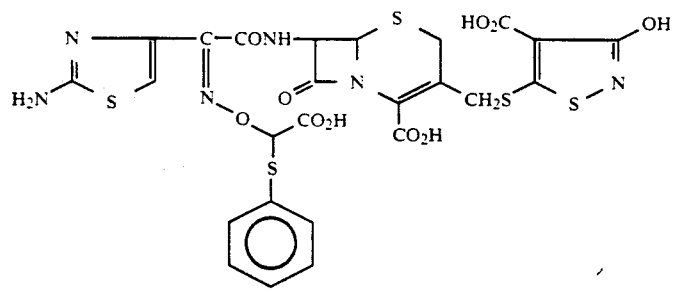

(1) After 2.05 g of sodium hydroxide was dissolved in 50 ml of water, 5.65 g of thiophenol was added to the solution under ice cooling, and the mixture was stirred for a half hour at room temperature. Under ice cooling, 10.0 g of tert-butyl bromoacetate was added to the reaction mixture and the resulting mixture was reacted at room temperature for 3 hours. After completion of the reaction, the reaction mixture was extracted 3 times with ethyl acetate and the extract was washed with saturated sodium chloride aqueous solution. After the ethyl acetate layer was dried over sodium sulfate, ethyl acetate was distilled off to give 12.8 g of crude tert-butyl (phenylthio)acetate.

Nuclear magnetic resonance spectrum (in CDCl$_3$) δ (ppm): 1.35 (9H, s), 3.40 (2H, s), 7.0-7.5 (5H, m).

(2) After 14.1 g of crude tert-butyl (phenylthio)acetate obtained in (1) was dissolved in 70 ml of carbon tetrachloride, 10.0 g of N-chlorosuccinimide was gradually added to the solution under ice cooling. The mixture was stirred at room temperature over night. After the insoluble materials were filtered off, carbon tetrachloride was removed by distillation to give 17.6 g of crude tert-butyl 2-chloro-2-(phenylthio)acetate.

Nuclear magnetic resonance spectrum (in CDCl$_3$) δ (ppm): 1.47 (9H, s), 5.28 (1H, s), 7.1-7.8 (5H, m).

(3) After 10.5 g of N-hydroxyphthalimide was dissolved in 65 ml of dimethylformamide, 9.7 ml of triethylamine was dropwise added to the solution under ice cooling. Then, 17.6 g of tert-butyl 2-chloro-2-(phenylthio)acetate obtained in (2) was dropwise added to the mixture followed by stirring at room temperature for 4 hours. After ethyl acetate was added to the reaction mixture, the resulting mixture was washed with water and then with saturated sodium chloride aqueous solution. After the organic phase was dried over magnesium sulfate, the solvent was distilled off to give 21.9 g of crude tert-butyl 2-(phenylthio)-2-phthalimidoxyacetate.

Nuclear magnetic resonance spectrum (in CDCl$_3$) δ (ppm): 1.38 (9H, s), 5.97 (1H, s), 7.1-8.0 (9H, m).

(4) After 21.9 g of crude tert-butyl 2-phenylthio-2-phthalimidoxyacetate obtained in (3) was dissolved in 200 ml of methylene chloride, 5.6 ml of hydrazine monohydrate was dropwise added to the solution. After stirring for 2 hours, 150 ml of 10% ammonia water was added to the mixture followed by extraction with methylene chloride 3 times. After washing with saturated sodium chloride aqueous solution, the methylene chloride phase was dried over anhydrous magnesium sulfate. Methylene chloride was distilled off to give 10.7 g of the crude product. The crude product was subjected to silica gel column chromatography and the column was eluted with benzene-ethyl acetate to give 3.44 g of tert-butyl 2-aminooxy-2-(phenylthio)acetate.

Nuclear magnetic resonance spectrum (in CDCl$_3$) δ (ppm): 1.41 (9H, s), 5.32 (1H, s), 5.4 (2H, brs), 7.1-7.7 (5H, m).

(5) After 3.44 g of tert-butyl 2-aminooxy-2-(phenylthio)acetate obtained in (4) was dissolved in 250 ml of methanol, 5.58 g of 2-(2-tritylaminothiazol-4-yl)-2-oxoacetic acid was added to the solution. After stirring at room temperature for an hour, the solvent was distilled off to give 8.57 g of crude (Z)-2-(2-tritylamino-4-thiazolyl)-2-[[(tert-butoxycarbonyl)(phenylthio)methoxy]imino]acetic acid.

Mass spectrum FAB (Pos.): 6.52.

Nuclear magnetic resonance spectrum (in DMSO-d$_6$) δ (ppm): 1.24 (9H, s), 5.80 (1H, s), 6.81 (1H, s), 7.0-7.5 (20H, m), 8.76 (1H, s).

(6) After 3.00 g of crude (Z)-2-(2-tritylamino-4-thiazolyl)-2-[[(tert-butoxycarbonyl)(phenylthio)methoxy]imino]acetic acid was dissolved in 15 ml of methylene chloride, 1.05 g of phosphorus pentachloride was added to the solution at −20° C. The mixture was stirred for an hour at −20° C. to give a solution of the acid chloride in methylene chloride. On the other hand, 1.70 g of p-methoxybenzyl 7-amino-3-chloromethyl-3-cephem-4-carboxylate hydrochloride was suspended in 15 ml of methylene chloride and, 1.25 ml of N,O-bis-trimethylsilylacetamide was added to the suspension. After stirring for 10 minutes under ice cooling, 1.66 ml of pyridine was further added to the mixture at −70° C. The solution of the acid chloride in methylene chloride previously prepared was added to the resulting solution at −70° C. After stirring for 10 minutes, the temperature was elevated to −20° C. and, water was added to the reaction mixture. The mixture was extracted with methylene chloride. After the organic phase was washed with saturated sodium chloride aqueous solution and dried over anhydrous sodium sulfate, the solvent was distilled off to give 4.78 g of caramel. This caramel was subjected to silica gel column chromatography and the column was eluted with benzene-ethyl acetate to give 2.03 g of p-methoxybenzyl 7β-[(Z)-2-(2-tritylamino-4-thiazolyl)-2-[[(R S)-(tert-butoxycarbonyl)(phenylthio)methoxy]imino]acetamido]-3-chloromethyl-3-cephem-4-carboxylate.

Infrared absorption spectrum $\nu_{max}^{KBr}$ (cm$^{-1}$): 1794.
Mass spectrum FAB (Pos.): 1002.

Nuclear magnetic resonance spectrum (in DMSO-d$_6$) δ (ppm): 1.25 (9H, s, t-Bu), 3.4-3.8 (2H, m, C$\underline{H}_2$ at the 2-position), 3.72 (s, 3H, OC$\underline{H}_3$), 4.44, 4.53 (2H, AB pattern, —C$\underline{H}_2$Cl) 5.1-5.3(1H. C$\underline{H}$ at the 6-position), 5.17, 5.23 (2H, AB pattern,

5.7-5.8 (1H, C$\underline{H}$ at the 7-position), 5.74, 5.77 (1H, s each,

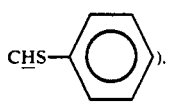

6.77 (1H, s,

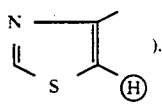

6.90, 7.25 (4H, AB pattern.

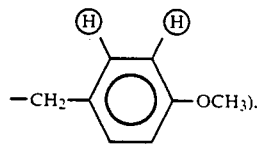

7.1-7.7 (20H, m,

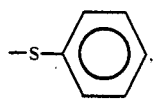

Trity), 8.88 (1H, s, N$\underline{H}$Tr), 9.70, 9.74 (1H, d each, CON$\underline{H}$).

(7) After 696 mg of 5-mercapto-4-carboxy-3-hydroxyisothiazole tripotassium salt was dissolved in 10 ml of water, 10 ml of methylene chloride, 1.62 g of tetra-n-butylammonium hydrogensulfate and 2.00 g of p-methoxybenzyl 7β-[(Z)-2-(2-tritylamino-4-thiazolyl)-2-[[(R S)-(tert-butoxycarbonyl)(phenylthio)methoxy]imino]acetamido]-3-chloromethyl-3-cephem-4-carboxylate obtained in (6) were added to the solution at room temperature. After stirring at room temperature overnight, the methylene chloride phase was separated and the aqueous phase was extracted with 10 ml of methylene chloride 3 times. The organic layers were collected and washed with 10 ml of saturated sodium chloride aqueous solution. After drying over anhydrous sodium sulfate, the solvent was distilled off to give caramel. This caramel was subjected to silica gel column chromatography and the column was eluted with chloroform-methanol to give 1.98 g of p-methoxybenzyl 7β-[(Z)-2-(2-tritylamino-4-thiazolyl)-2-[[(R S)-(tert-butoxycarbonyl)(phenylthio)methoxy]imino]acetamido]-3-[[(4-carboxy-3-hydroxy-5-isothiazolyl)thio]methyl]-3-cephem-4-carboxylate tetra-n-butylammonium salt.

Infrared absorption spectrum $\nu_{max}^{KBr}$ (cm$^{-1}$): 1790.
Mass spectrum FAB (Neg.): 1141.

Nuclear magnetic resonance spectrum (in DMSO-d$_6$) δ (ppm): 0.92 (12H, t, N(CH$_2$CH$_2$CH$_2$C$\underline{H}_3$)$_4$), 1.1-1.7 (16H, m, N(CH$_2$C$\underline{H}_2$C$\underline{H}_2$CH$_3$)$_4$), 1.25 (9H, s, t-Bu), 3.1-3.3 (10H, m, C$\underline{H}_2$ at the 2-position, N(C$\underline{H}_2$CH$_2$CH$_2$CH$_3$)$_4$), 3.72 (s, 3H, OC$\underline{H}_3$), 3.98, 4.04 (2H, AB pattern, —C$\underline{H}_2$S—), 5.1-5.3 (1H, m, C$\underline{H}$ at the 6-position), 5.27 (2H, s,

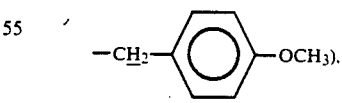

5.6-5.8 (1H, C$\underline{H}$ at the 7-position), 5.73, 5.76 (1H, s each,

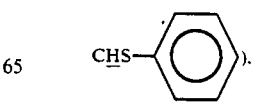

6.77 (1H, s each,

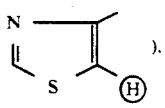

6.86, 7.21 (4H, AB pattern,

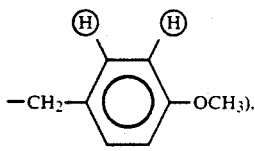

7.1–7.6 (20H, m,

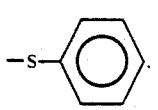

Trityl), 8.87 (1H, s, N$\underline{\text{H}}$Tr), 9.66, 9.70 (1H, d each, CON$\underline{\text{H}}$).

(8) After 2.56 g of p-methoxybenzyl 7β-[(Z)-2-(2-tritylamino-4-thiazolyl)-2-[[(R  S)-(tert-butoxycarbonyl)(phenylthio)methoxy]imino]acetamido]-3-[[(4-carboxy-3-hydroxy-5-isothiazolyl)thio]methyl]-3-cephem-4-carboxylate tetra-n-butylammonium salt obtained in (7) was dissolved in 8 ml of methylene chloride and 3 ml of anisole, 10 ml of trifluoroacetic acid was dropwise added to the solution under ice cooling. The mixture was then stirred at room temperature for an hour. Trifluoroacetic acid and methylene chloride were distilled off under reduced pressure. The resulting residue was suspended in 10 ml of water. Under ice cooling, 20 ml of trifluoroacetic acid was added to the suspension. After stirring at room temperature for an hour, trifluoroacetic acid and water were removed by distillation under reduced pressure. Ethyl ether was added to the residue to make it powders. By filtration, 1.71 g of powders were obtained. After the powders were dissolved in diluted sodium hydrogencarbonate aqueous solution, 1N-HCl aqueous solution was added to the solution to adjust pH to 3. The aqueous solution was adsorbed to DIAION HP20 followed by elution with water and then with methanol-water. The fractions containing the desired product were collected. After concentration, the concentrate was freeze dried to give 140 mg of 7β-[(Z)-2-(2-amino-4-thiazolyl)-2-[[(R  S)(carboxy)(phenylthio)methoxy]imino]acetamido]-3-[[(4-carboxy-3-hydroxy-5-isothiazolyl)thio]methyl]-3-cephem-4-carboxylic acid.

Infrared absorption spectrum $\nu_{max}^{KBr}$ (cm$^{-1}$): 1778.
Mass spectrum FAB (Pos.): 725.

Nuclear magnetic resonance spectrum (in DMSO-d$_6$) δ (ppm): 3.65 (2H, AB pattern, C$\underline{\text{H}}_2$ at the 2-position), 4.07, 4.24 (2H, AB pattern, —C$\underline{\text{H}}_2$S—), 5.18 (1H, d, C$\underline{\text{H}}$ at the 6-position), 5.7–5.9 (1H, m, C$\underline{\text{H}}$ at the 7-position), 5.81, 5.84 (1H, s each

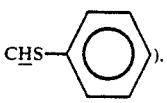

6.78, 6.80 (1H, s each,

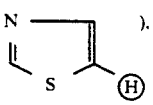

7.2–7.6 (5H, m,

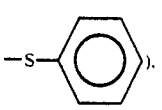

9.67, 9.71 (1H, d each, CON$\underline{\text{H}}$).

EXAMPLE 4

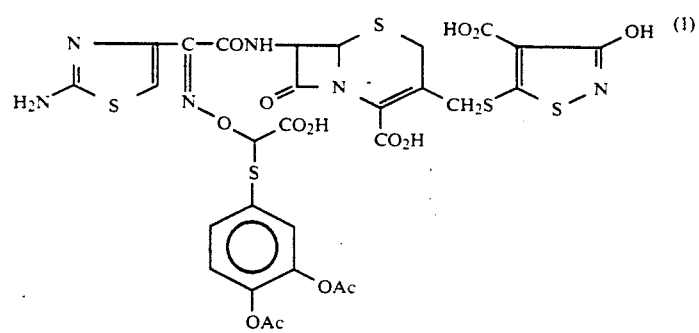

After 26.0 g of catechol was dissolved in 400 ml of water, 15.2 g of thiourea was added to the solution at room temperature to dissolve. A solution of 130 g of potassium ferricyanide and 200 g of sodium acetate in 600 ml of water was added to the solution at room temperature and, 200 g of sodium acetate was further added to the mixture. After stirring overnight at room temperature, the reaction mixture was dissolved in 1N-HCl aqueous solution and the insoluble materials were filtered off. To the aqueous solution were added 200 g of sodium acetate and 400 ml of water. The mixture was stirred to precipitate the salt. The salt was taken out by filtration and dried under reduced pressure to give 52.5 g of S-(3,4-dihydroxyphenyl)isothiourea acetate.

Nuclear magnetic resonance spectrum (in DMSO-d$_6$) δ (ppm): 1.83 (3H, s), 6.7–6.9 (3H, m), 8.3 (6H, brs).

(2) After 384 ml of 1N-NaOH aqueous solution was added to 23.4 g of S-(3,4-dihydroxyphenyl)isothiourea acetate obtained in (1) at room temperature to dissolve, the mixture was stirred for 30 minutes. To the reaction solution was added 15.5 ml of tert-butyl bromoacetate. The mixture was reacted at room temperature for 3 hours. After completion of the reaction, the reaction mixture was extracted 4 times with ethyl acetate and the extract was washed with saturated sodium chloride aqueous solution. After the ethyl acetate phase was dried over sodium sulfate, ethyl acetate was distilled off to give the crude product. The crude product was subjected to silica gel column chromatography and the column was eluted with chloroform-ethyl acetate to give 17.7 g of tert-butyl (3,4-dihydroxyphenylthio)acetate.

Infrared absorption spectrum $\nu_{max}^{KBr}$ (cm$^{-1}$): 3428, 2992, 1706, 1602, 1516, 1374, 1316, 1276, 1170, 1134, 760.

Mass spectrum EI: 256, 200, 155, 57.

Nuclear magnetic resonance spectrum (in DMSO-d$_6$) $\delta$ (ppm): 1.33 (9H, s), 3.46 (2H, s), 6.6–6.9 (3H, m), 9.08 (2H, brs).

(3) After 17.7 g of tert-butyl (3,4-dihydroxyphenylthio)acetate was dissolved in 70 ml of methylene chloride, 11.4 ml of pyridine and then 10.0 ml of acetyl chloride were added to the solution under ice cooling. After stirring for 20 minutes, water was added and the resulting mixture was extracted twice with methylene chloride. After drying over magnesium sulfate, the solvent was distilled off to give the crude product. The crude product was subjected to silica gel column chromatography and the column was eluted with hexane-ethyl acetate to give 19.7 g of tert-butyl (3,4-diacetoxyphenylthio)acetate.

Infrared absorption spectrum $\nu_{max}^{KBr}$ (cm$^{-1}$): 2992, 1780, 1734, 1494, 1208, 1172, 1014.

Nuclear magnetic resonance spectrum (in CDCl$_3$) $\delta$ (ppm): 1.37 (9H, s), 2.25 (3H, s), 2.26 (3H, s), 3.61 (2H, s), 7.0–7.4 (3H, m).

(4) After 19.7 g of tert-butyl (3,4-diacetoxyphenylthio)acetate obtained in (3) was dissolved in 100 ml of carbon tetrachloride, 9.3 g of N-chlorosuccinimide was gradually added to the solution under ice cooling. The mixture was stirred at room temperature overnight. After the insoluble materials were filtered off, carbon tetrachloride was removed by distillation to give 25.4 g of crude tert-butyl 2-chloro-2-(3,4-diacetoxyphenylthio)acetate.

Mass spectrum EI: 374.

Nuclear magnetic resonance spectrum (in CDCl$_3$) $\delta$ (ppm): 1.47 (9H, s), 2.29 (6H, s), 5.41 (1H, s), 7.1–7.6 (3H, m).

(5) After 11.1 g of N-hydroxyphthalimide was dissolved in 250 ml of dimethylformamide, 9.5 ml of triethylamine was dropwise added to the solution under ice cooling. Then, 25.4 g of crude tert-butyl 2-chloro-2-(3,4-diacetoxyphenylthio)acetate obtained in (4) was dropwise added to the mixture at −40° C. The temperature was gradually elevated to room temperature. After ethyl acetate was added to the reaction solution, the resulting mixture was washed with water and then with saturated sodium chloride aqueous solution. After the organic phase was dried over magnesium sulfate, the solvent was distilled off. Ethyl ether was added to the residue and side products precipitated were removed by filtration. Ethyl ether in the filtrate was again removed by distillation. In 100 ml of methylene chloride was dissolved 72 g of the residue. Under ice cooling, pyridine (5.5 ml) and then acetyl chloride (4.8 ml) were added to the solution. After stirring for 20 minutes, water was added to the mixture. The mixture was extracted twice with methylene chloride. After drying over magnesium sulfate, the solvent was distilled off to give 35.1 g of the crude product. The crude product was subjected to silica gel column chromatography and the column was eluted with hexaneethyl acetate to give 8.38 g of the oily product. Ethyl ether was added to the oily product to make powders. The powders were filtered to give 3.27 g of tert-butyl 2-(3,4-diacetoxyphenylthio)-2-(phthalimidoxy)acetate.

Infrared absorption spectrum $\nu_{max}^{KBr}$ (cm$^{-1}$): 3000, 1780, 1740, 1500, 1380, 1000, 700.

Nuclear magnetic resonance spectrum (in CDCl$_3$) $\delta$ (ppm): 1.35 (6H, s), 1.56 (3H, s), 2.28 (3H, s), 2.29 (3H, s), 5.94 (1H, s), 7.1–7.3 (3H, m), 7.7–7.9 (4H, m).

(6) After 3.10 g of tert-butyl 2-(3,4-diacetoxyphenylthio)-2-(phthalimidoxy)acetate obtained in (5) was dissolved in 50 ml of methylene chloride, 0.33 ml of methylhydrazine was dropwise added to the solution. After stirring for 30 minutes at −60° C., stirring was continued at 0° C. for further an hour. The temperature was elevated to room temperature and insoluble matters were filtered off. The solvent was distilled off to give 26.4 g of crude tert-butyl 2-aminooxy-2-(3,4-diacetoxyphenylthio)acetate.

Mass spectrum FAB (Pos.): 372.

Nuclear magnetic resonance spectrum (in CDCl$_3$) $\delta$ (ppm): 1.42 (9H, s), 2.28 (6H, s), 5.31 (1H, s), 5.7 (2H, brs), 6.9–7.6 (3H, m).

(7) After 2.58 g of crude tert-butyl 2-aminooxy-2-(3,4-diacetoxyphenylthio)acetate obtained in (6) was dissolved in 100 ml of methanol, 2.38 g of 2-(2-tritylamino-thiazol-4-yl)-2-oxoacetic acid was added to the solution. After stirring at room temperature for an hour, the solvent was distilled off. The residue was subjected to silica gel column chromatography and the column was eluted with chloroform-ethyl acetate to give 2.28 g of (Z)-2-(2-tritylamino-4-thiazolyl)-2-[[tertbutoxycarbonyl)(3,4-diacetoxyphenylthio)methoxy]imino]acetic acid.

Infrared absorption spectrum $\nu_{max}^{KBr}$ (cm$^{-1}$): 2992, 2948, 1778, 1740, 1494, 1374, 1208, 1170, 1014, 702.

Mass spectrum FAB (Pos.): 768.

Nuclear magnetic resonance spectrum (in DMSO-d$_6$) $\delta$ (ppm): 1.26 (9H, s), 2.26 (6H, s), 5.96 (1H, s), 6.90 (1H, s), 7.1–7.5 (18H, m), 8.86 (1H, s).

(8) After 2.75 g of (Z)-2-(2-tritylamino-4-thiazolyl)-2[[(tert-butoxycarbonyl)(3,4-diacetoxyphenylthio)methoxy]imino]acetic acid was dissolved in 30 ml of methylene chloride, 746 mg of phosphorus pentachloride was added to the solution at −20° C. The mixture was stirred for an hour at −20° C. to give a solution of the acid chloride in methylene chloride. On the other hand, 1.45 g of p-methoxybenzyl 7-amino-3-chloromethyl-3-cephem-4-carboxylate hydrochloride was suspended in 20 ml of methylene chloride and, 0.89 ml of N,O-bistrimethylsilylacetamide was added to the suspension under ice cooling. After stirring for 10 minutes under ice cooling, 1.5 ml of pyridine was further added to the mixture at −60° C. The solution of the acid chloride in methylene chloride previously prepared was added to the resulting solution at −60° C. After stirring for 10 minutes, the temperature was elevated to −20° C. and, water was added to the reaction mixture. The aqueous phase was extracted with methylene chloride. After the organic phase was washed with saturated sodium chloride aqueous solution and dried over anhydrous magnesium sulfate, the solvent was distilled off to give 4.84 g of crude p-methoxybenzyl 7$\beta$-[(Z)-2-(2-tritylamino-4-thiazolyl)-2-[[(R S)-(tertbutoxycarbonyl)(3,4-diacetoxyphenylthio)methoxy]imino]acetamido]-3-chloromethyl-3-cephem-4-carboxylate.

Infrared absorption spectrum $\nu_{max}^{KBr}$ (cm$^{-1}$): 1780.
Mass spectrum FAB (Pos.): 1118.

Nuclear magnetic resonance spectrum (in DMSO-d$_6$)
δ (ppm): 1.20 (9H, s, t-Bu), 2.26 (6H, s), 3.3–3.7 (2H, m, C$\underline{H}_2$ at the 2-position), 3.67 (s, 3H, OC$\underline{H}_3$), 4.39, 4.47 (2$\overline{H}$, AB pattern, —C$\underline{H}_2$Cl), 5.0–5.2 (1$\overline{H}$, d, C$\underline{H}$ at the 6-position), 5.10, 5.17 ($\overline{2H}$, AB pattern,

5.6–5.7 (1H, m, C$\underline{H}$ at the 7-position), 5.77, 5.79 (1H, s each,

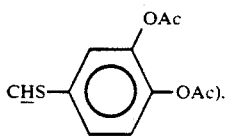

6.72 (1H, s

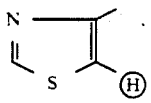

6.84, 7.29 (4H, AB pattern,

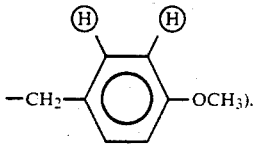

7.1–7.5 (18H, m,

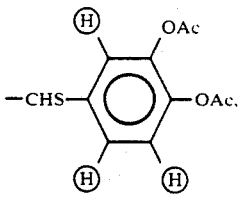

Trityl), 8.80, (1H, s, N$\underline{H}$Tr), 9.70, (1H, d, CON$\underline{H}$).

(9) After 1.24 g of 5-mercapto-4-carboxy-3-hydroxyisothiazole tripotassium salt was dissolved in 20 ml of water, 20 ml of methylene chloride, 2.88 g of tetra-n-butylammonium hydrogensulfate and 4.79 g of p-methoxybenzyl 7β-[(Z)-2-(2-tritylamino-4-thiazolyl)-2-[[(R S)-(tert-butoxycarbonyl)(3,4-diacetoxyphenylthio)methoxy]imino]acetamido]-3-chloromethyl-3-cephem-4-carboxylate obtained in (8) were added to the solution at room temperature. After stirring at room temperature overnight, the methylene chloride phase was separated and the aqueous phase was extracted with methylene chloride twice. The organic layers were collected and washed with 10 ml of saturated sodium chloride aqueous solution. After drying over anhydrous sodium sulfate, the solvent was distilled off to give caramel. This caramel was subjected to silica gel column chromatography and the column was eluted with chloroform-methanol to give 2.06 g of p-methoxybenzyl 7β-[(Z)-2-(2-tritylamino-4-thiazolyl)-2-[[(R S)-(tertbutoxycarbonyl)(3,4-diacetoxyphenylthio)methoxy]imino]acetamido]-3-[[(4-carboxy-3-hydroxy-5-isothiazolyl)thio]methyl]-3-cephem-4-carboxylate tetra-n-butylammonium salt.

Infrared absorption spectrum $\nu_{max}^{KBr}$ (cm$^{-1}$): 1780.
Mass spectrum FAB (Neg.): 1257, (Pos.); 1259.

Nuclear magnetic resonance spectrum (in DMSO-d$_6$)
δ (ppm): 0.92 (12H, t, N(CH$_2$CH$_2$CH$_2$CH$_3$)$_4$), 1.1–1.7 (16H, m, N(CH$_2$CH$_2$CH$_2$CH$_3$)$_4$), 1.25 ($\overline{9H}$, s, t-Bu), 3.1–3.3 (8H, m, N(C$\overline{H_2}$CH$_2$CH$_2$CH$_3$)$_4$), 2.26 (6H, s), 3.60 (2H, AB pattern, $\overline{CH}_2$ at the 2-position), 3.72 (s, 3H, OCH$_3$), 3.98, 4.04 (2H, $\overline{AB}$ pattern, —CH$_2$S—), 5.1–5.3 (1$\overline{H}$, m, C$\underline{H}$ at the 6-position), 5.14, 5.2$\overline{1}$ (2H, AB pattern,

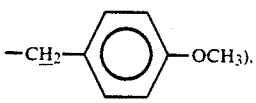

5.6–5.7 (1H, C$\underline{H}$ at the 7-position), 5.81, 5.83 (1H, s each,

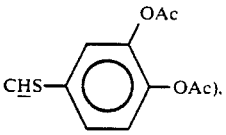

6.79 (1H, s,

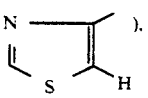

6.86, 7.21 (4H, AB pattern,

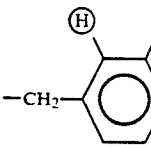

7.1–7.5 (18H, m,

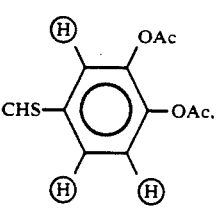

Trityl), 8.86, (1H, s, N$\underline{H}$Tr), 9.72 (1H, d, CON$\underline{H}$), 13.8 (1H, brs, CON$\underline{H}$).

(10) After 2.01 g of p-methoxybenzyl 7β-[(Z)-2-(2-tritylamino-4-thiazolyl)-2-[[(R S)-(tert-butoxycarbonyl)(3,4-diacetoxyphenylthio)methoxy]imino]acetamido]-3-[[(4-carboxy-3-hydroxy-5-isothiazolyl)thio]methyl]-3-cephem-4-carboxylate tetra-n-butylammonium salt obtained in (9) was dissolved in 10 ml of methylene chloride and 1 ml of anisole, 10 ml of trifluoroacetic acid was dropwise added to the solution under ice cooling. The mixture was then stirred at room temperature for an hour. Trifluoroacetic acid and methylene chloride were distilled off under reduced pressure. The resulting residue was suspended in 5 ml of water. Under ice cooling, 10 ml of trifluoroacetic acid was added to the suspension. After stirring at room temperature for an hour, trifluoroacetic acid and water were removed by distillation under reduced pressure. Ethyl ether was added to the residue to make powders. By filtration, 1.18 g of powders were obtained. After 250 mg of the powders were suspended in water, the mixture was adsorbed to DIAION HP20 followed by elution with water-methanol. The fractions containing the desired product were collected. After concentration, the concentrate was freeze dried to give 65 mg of 7β-[(Z)-2-(2-amino-4-thiazolyl)-2-[[(R S)-carboxy(3,4-diacetoxyphenylthio)methoxy]imino]acetamido]-3-[[(4-carboxy-3-hydroxy-5-isothiazolyl)thio]methyl]-3-cephem-4-carboxylic acid.

Infrared absorption spectrum $\nu_{max}^{KBr}$ (cm$^{-1}$):1776.
Mass spectrum FAB (Pos.): 841.
Nuclear magnetic resonance spectrum (in DMSO-$d_6$) δ (ppm): 2.26 (6H, s), 3.55, 3.74 (2H, AB pattern, $CH_2$ at the 2-position), 4.05, 4.28 (2H, AB pattern, —$CH_2S$—), 5.19, 5.20 (1H, d each, CH at the 6-position), 5.7–5.9 (1H, CH at the 7-position), 5.92, 5.94 (1H, s each,

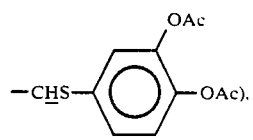

6.82, 6.84 (1H, s each,

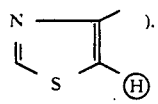

7.1–7.5 (3H, m,

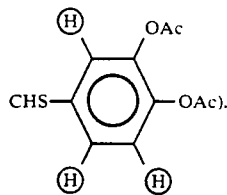

9.74, 9.77 (1H, d each, CONH).

EXAMPLE 5

After 600 mg of 7β-[(Z)-2-(2-amino-4-thiazolyl)-2-[[(R S)-(carboxy)(3,4-diacetoxyphenylthio)methoxy]imino]acetamido]-3-[[(4-carboxy-3-hydroxy-5-isothiazolyl)thio]methyl]-3-cephem-4-carboxylic acid obtained in Example 4 (10) was suspended in 20 ml of water, saturated sodium hydrogencarbonate aqueous solution was added to the suspension at room temperature to adjust pH to 8. After stirring at room temperature for 2.5 hours, the aqueous solution was adsorbed to DIAION HP20 followed by elution with water. The fractions containing the desired product were collected. After concentration, the concentrate was freeze dried to give 150 mg of trisodium 7β-[(Z)-2-(2-amino-4-thiazolyl)-2-[[(R S)-(carboxy)(3,4-dihydroxyphenylthio)methoxy]imino]acetamido]-3-[[(4-carboxy-3-hydroxy-5-isothiazolyl)thio]methyl]-3-cephem-4-carboxylate.

Infrared absorption spectrum $\nu_{max}^{KBr}$ (cm$^{-1}$): 1766.
Mass spectrum FAB (Pos.): 779, (Neg.): 777.
Nuclear magnetic resonance spectrum (in $D_2O$) δ (ppm): 3.34, 3.72 (2H, AB pattern, $CH_2$ at the 2-position), 3.86, 4.43 (2H, AB pattern, —$CH_2S$—), 5.12, 5.14 (1H, d each, CH at the 6-position), 5.69, 5.73 (1H, d each, CH at the 7-position), 5.80, 5.81 (1H, s each,

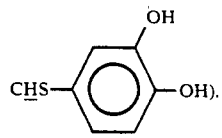

6.81, 6.84 (1H, s each,

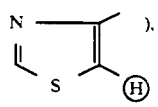

7.2–7.6 (3H, m,

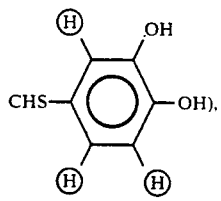

EXAMPLE 6

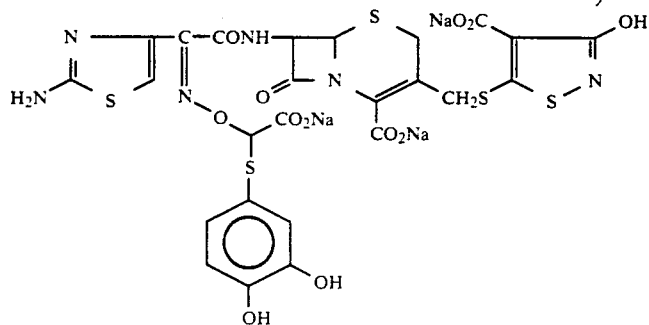

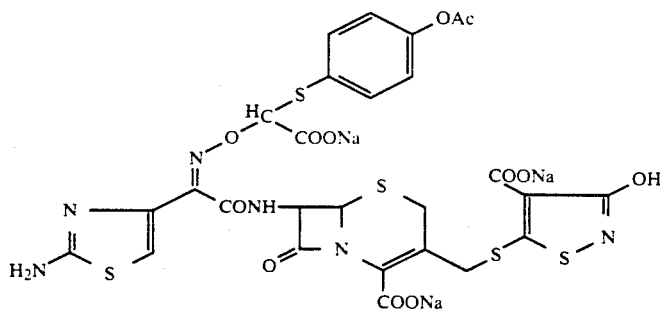

(1) After 25.42 g of p-hydroxythiophenol was dissolved in 100 ml of methylene chloride, 20.2 g of triethylamine was dropwise added to the solution under ice cooling. Then, 39.2 g of tert-butyl bromoacetate was added to the mixture followed by reacting at room temperature for an hour. After completion of the reaction, the reaction mixture was washed with 3 times with 1N-HCl and once with saturated sodium chloride aqueous solution. After the organic phase was dried over magnesium sulfate, methylene chloride was distilled off to give tert-butyl (4-hydroxyphenylthio)acetate (quantitative).

Nuclear magnetic resonance spectrum (in $CDCl_3$) δ (ppm): 1.40 (9H, s), 3.45 (2H, s), 6.8, 7.4 (4H, AB).

(2) After tert-butyl (4-hydroxyphenylthio)acetate obtained in (1) was dissolved in methylene chloride, 25.6 g of pyridine and then 25.4 g of acetyl chloride were added to the solution under ice cooling. After stirring for 2 hours at room temperature, the reaction mixture was washed twice with water, twice with 1N-HCl and once with saturated sodium chloride aqueous solution. After drying over magnesium sulfate, methylene chloride was distilled off to give the crude product. The crude product was subjected to silica gel column chromatography and the column was eluted with methylene chloride to give 54.51 g of tert-butyl (4-acetoxyphenylthio)acetate.

Nuclear magnetic resonance spectrum (in $CDCl_3$) δ (ppm): 1.50 (9H, s), 2.40 (3H, s), 3.60 (2H, s), 7.0, 7.5 (4H, AB).

(3) After 54 g of tert-butyl (4acetoxyphenylthio)acetate obtained in (2) was dissolved in 600 ml of carbon tetrachloride, 32.0 g of N-chlorosuccinimide was added to the solution under ice cooling. The mixture was stirred at room temperature overnight. After the insoluble materials were filtered off, carbon tetrachloride was removed by distillation to give crude tert-butyl 2-chloro-2-(4-acetoxyphenylthio)acetate (quantitative).

Nuclear magnetic resonance spectrum (in $CDCl_3$) δ (ppm): 1.60 (9H, s), 2.30 (3H, s), 5.40 (1H, s), 7.25, 7.65 (4H, AB).

On the other hand, 32.2 g of N-hydroxyphthalimide was dissolved in 320 ml of dimethylformamide and, 20.2 g of triethylamine was dropwise added to the solution under ice cooling. Then, a solution of the previously obtained crude tert-butyl 2-chloro-2-(4-acetoxyphenylthio)acetate (whole amount) in dimethylformamide (100 ml) was dropwise added to the mixture at −40° C. The temperature was gradually elevated at room temperature. After the mixture was reacted at room temperature for further 4 hours, dimethylformamide was distilled off at 30° to 35° C. under reduced pressure and the residue was diluted with 250 ml of ethyl acetate. The dilution was thoroughly washed once with water and then with diluted potassium carbonate aqueous solution and finally with saturated sodium chloride aqueous solution. After the organic phase was dried over magnesium sulfate, the solvent was distilled off to give the crude product. To the crude product was added 100 ml of diethyl ether. The precipitated N-acetoxyphthalimide was removed by filtration. The mother liquor was again concentrated and diethyl ether was added to the residue. By adding standard seed crystals of the desired product, 12.57 g of tert-butyl 2-(4-acetoxyphenylthio)-2-(phthalimidoxy)acetate.

Nuclear magnetic resonance spectrum (in $CDCl_3$) δ (ppm): 1.27 (9H, s), 6.08 (1H, s), 7.20, 7.85 (4H, AB).

Mass spectrum FAB (Pos.): 443.

(4) After 11.53 g of tert-butyl 2-(4-acetoxyphenylthio)-2-(phthalimidoxy)acetate obtained in (3) was dissolved in 200 ml of methylene chloride, a methylene chloride solution (15 ml) of 1.20 g of methylhydrazine was dropwise added to the solution at −70° C. The temperature was gradually elevated to room temperature and insoluble matters were filtered off. The solvent was distilled off to give crude tert-butyl 2-aminooxy-2-(4-acetoxyphenylthio)acetate. The crude product was dissolved in 200 ml of methanol and 8.29 g of 2-(2-tritylaminothiazol-4-yl)-2-oxoacetic acid was added to the solution. After stirring at room temperature for an hour and a half, the solvent was distilled off. The residue was subjected to silica gel column chromatography and the column was eluted with chloroform-methanol to give 10.52 g of (Z)-2-(2-tritylamino-4-thiazolyl)-2-[[(tert-butoxycarbonyl)(4-acetoxyphenylthio)methoxy]imino]acetic acid.

Nuclear magnetic resonance spectrum (in DMSO-$d_6$) δ (ppm): 1.22 (9H, s), 2.25 (3H, s), 6.80 (1H, s), 7.1–7.4 (15H, m), 7.03, 7.48 (4H, AB).

Mass spectrum FAB (Pos.): 710.

(5) After 5.18 g of (Z)-2-(2-tritylamino-4-thiazolyl)-2-[[(tert-butoxycarbonyl)(4-acetoxyphenylthio)methoxy]imino]acetic acid obtained in (4) was dissolved in 50 ml of methylene chloride, 1.52 g of phosphorus pentachloride was added to the solution under ice cooling. The mixture was stirred for 50 minutes under ice cooling to give a solution of the acid chloride in methylene chloride. On the other hand, 2.96 g of p-methoxybenzyl 7-amino-3-chloromethyl-3-cephem-4-carboxylate hydrochloride was suspended in 100 ml of methylene chloride and, 2.5 ml of N,O-bistrimethylsilyltrifluoroacetamide was added to the suspension. After the mixture was stirred at room temperature until it became a homogeneous solution, 3.46 g of pyridine was added to the solution at −60° C. The solution of the acid chloride in methylene chloride previously prepared was added thereto. After stirring for an hour at −70° C. to −50° C., 1N hydrochloric acid was added to the mixture. After the organic phase was washed twice with 1N hydrochloric acid and then with saturated sodium chloride aqueous solution, the organic phase was dried over anhydrous magnesium sulfate. The solvent was distilled off to give 8.8 g of crude p-methoxybenzyl 7β-[(Z)-2-(2-tritylamino-4-thiazolyl)-2-[[(R  S)-(tert-butoxycarbonyl)(4-acetoxyphenylthio)methoxy]imino]acetamido]-3-chloromethyl-3-cephem-4-carboxylate.

Infrared absorption spectrum $\nu_{max}^{KBr}$ (cm$^{-1}$): 1794.
Mass spectrum FAB (Pos.): 1060.
Nuclear magnetic resonance spectrum (in DMSO-d$_6$) δ (ppm): 1.25 (9H, s, $^t$Bu), 2.25 (3H, s,

3.51 and 3.69 (2H, AB, C$\underline{H}_2$ at the 2-position), 3.74 (3H, s, OC$\underline{H}_3$), 4.45 and 4.51 (2$\overline{H}$, AB, C$\underline{H}_2$ at the 3-position), 5.20 (1H, d, C$\underline{H}$ at the 6-position), 5.17 and 5.22 (2H, AB,

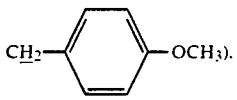

5.77 (1H, d, C$\underline{H}$ at the 6-position), 5.8 (1H, s,

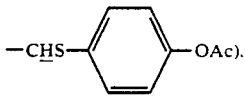

6.8 (1H, S,

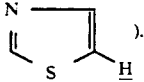

6.9–7.6 (23H, m,

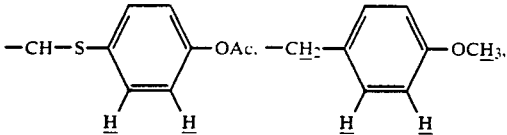

Trityl), 9.74 and 9.80 (1H, d each, CON$\underline{H}$).

(6) After 2.54 g of 5-mercapto-4-carboxy-3-hydroxyisothiazole tripotassium salt was dissolved in 100 ml of water, 50 ml of methylene chloride, 5.95 g of tetra-n-butylammonium hydrogensulfate and 8.8 g of crude p-methoxybenzyl 7β-[(Z)-2-(2-tritylamino-4-thiazolyl)-2-[[(R  S)-(tert-butoxycarbonyl)(4-acetoxyphenylthio)methoxy]imino]acetamido]-3-chloromethyl-3-cephem-4-carboxylate previously obtained were added to the solution at room temperature. After stirring at room temperature overnight, the methylene chloride phase was separated and the aqueous phase was extracted with methylene chloride twice. The organic layers were collected and washed with saturated sodium chloride aqueous solution. After drying over anhydrous magnesium sulfate, the solvent was distilled off to give caramel. This caramel was subjected to silica gel column chromatography and the column was eluted with chloroform-methanol to give 11.2 g of p-methoxybenzyl 7β-[(Z)-2-(2-tritylamino-4-thiazolyl)-2-[[(R  S)-(tert-butoxycarbonyl)(4-acetoxyphenylthio)methoxy]imino]acetamido]-3-[[(4-carboxy-3-hydroxy-5-isothiazolyl)thio]methyl]-3-cephem-4-carboxylate tetra-n-butylammonium salt.

Infrared absorption spectrum $\nu_{max}^{KBr}$ (cm$^{-1}$): 1792.
Nuclear magnetic resonance spectrum (in DMSO-d$_6$) δ (ppm): 1.3 (9H, s, $^t$Bu), 2.25 (3H, s,

3.48 and 3.74 (2H, AB, C$\underline{H}_2$ at the 2-position), 3.71 (3H, s, OC$\underline{H}_3$), 4.0 and 4.17 (2$\overline{H}$, AB, C$\underline{H}_2$ at the 3-position), 5.17 (1$\overline{H}$, d, —C$\underline{H}$— at the 6-position), 5.20 (2H, s,

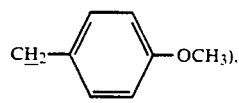

6.8–7.6 (23H, m,

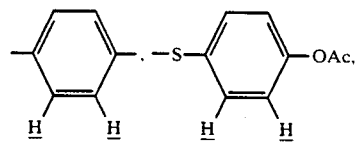

Trityl), 8.9 (1H, brs, N$\underline{H}$Tr), 9.68 and 9.77 (1H, d each, CON$\underline{H}$).

(7) After 330 mg of p-methoxybenzyl 7β-[(Z)-2-(2-tritylamino-4-thiazolyl)-2-[[(R  S)-(tert-butoxycarbonyl)(4-acetoxyphenylthio)methoxy]imino]acetamido]-3-[[(4-carboxy-3-hydroxy-5-isothiazolyl)thio]methyl]-3-cephem-4-carboxylate tetra-n-butylammonium salt obtained in (6) was dissolved in 5 ml of methylene chloride and 0.3 ml of anisole, 10 ml of trifluoroacetic acid was added to the solution under ice cooling. The mixture was then stirred at room temperature for an hour. Trifluoroacetic acid and methylene chloride were distilled off under reduced pressure. Diethyl ether was added to the residue to form powders. The solid was taken out by filtration and dissolved in 8 ml of trifluoroacetic acid and 4 ml of water under ice cooling.

After the solution was stirred at room temperature for an hour, trifluoroacetic acid and methylene chloride were distilled off under reduced pressure. Diethyl ether was added to the residue to form powders. By filtration, 187 mg of powders were obtained. After the powders were suspended in 30 ml of water, a diluted sodium hydrogencarbonate aqueous solution was added to the suspension. The resulting homogeneous solution was adsorbed to DIAION HP20 followed by elution with water and then with water-methanol. The fractions containing the desired product were collected. After concentration, the concentrate was freeze dried to give 64 mg of trisodium 7β-[(Z)-2-(2-amino-4-thiazolyl)-2-[[(R  S)-(carboxy)(4-acetoxyphenylthio)methoxy]imino]acetamido]-3-[[(4-carboxy-3-hydroxy-5-iso-thiazolyl)thio]methyl]-3-cephem-4-carboxylate.

Infrared absorption spectrum $\nu_{max}^{KBr}$ (cm$^{-1}$): 1764.

Mass spectrum FAB (Pos.): 849.

Nuclear magnetic resonance spectrum (in DMSO-d$_6$) δ (ppm): 2.22 (3H, s,

3.82 and 3.88 (2H, AB, CH$_2$ at the 2-position), 4.45 and 4.51 (2H, AB, CH$_2$ at the 3-position), 5.0 (1H, d, C$\underline{H}$ at the 6-position), 5.82 (1H, s each,

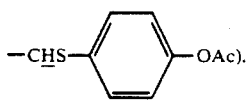

6.83 and 6.85 (1H, s each,

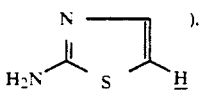

7.2 (2H, brs, N$\underline{H}_2$), 11.30 and 11.20 (1H, s each, CON$\underline{H}$).

EXAMPLE 7

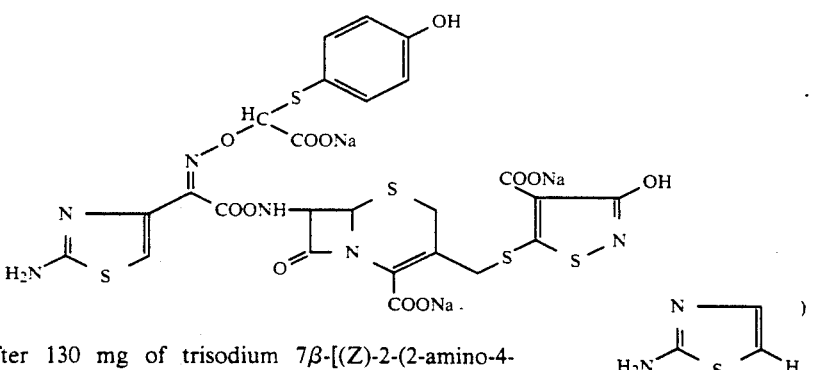

After 130 mg of trisodium 7β-[(Z)-2-(2-amino-4-thiazolyl)-2-[[(R S)-(carboxy)(4-acetoxyphenylthio)methoxy]imino]acetamido]-3-[[(4-carboxy-3-hydroxy-5-isothiazolyl)thio]methyl]-3-cephem-4-carboxylate was dissolved in 10 ml of water, 220 mg of sodium hydrogencarbonate was added to the solution. The mixture was stirred at room temperature for 9.5 hours.

The aqueous solution was adsorbed to DIAION HP20 followed by elution with water. The fractions containing the desired product were collected. After concentration, the concentrate was freeze dried to give 50 mg of trisodium 7β-[(Z)-2-(2-amino-4-thiazolyl)-2-

[[(R S)-(carboxy)(4-hydroxy-phenylthio)methoxy]imino]acetamido]-3-[[(4-carboxy-3-hydroxy-5-isothiazolyl)thio]methyl]-3-cephem-4-carboxylate.

Infrared absorption spectrum $\nu_{max}^{KBr}$ (cm$^{-1}$): 1770.

Mass spectrum FAB (Neg.): 739.

Nuclear magnetic resonance spectrum (in DMSO-d$_6$) δ (ppm): 3.28 and 3.57 (2H, AB, CH$_2$ at the 2-position), 5.00 (1H, d, C$\underline{H}$ at the 6-position), 5.40 and 5.46 (1H, s each,

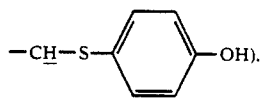

5.51 and 5.60 (1H, C$\underline{H}$ at the 7-position), 6.62 and 7.26 (4H, AB,

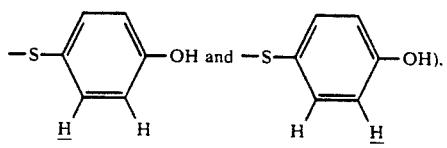

6.82 and 6.86 (1H, s each

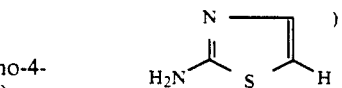

EXAMPLE 8

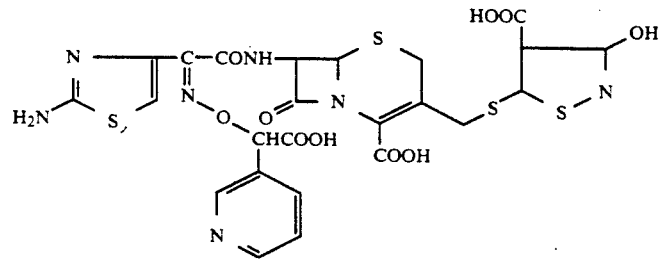

(1) After 3.7 ml (71.8 mmols) of bromine and 0.1 ml (0.1 mmol) of phosphorus tribromide were added to 10 g (57.6 mmoles) of 3-pyridylacetic acid, the resulting mixture was stirred at 80° to 90° C. for an hour. At room temperature 150 ml of dichloromethane was added to the mixture and 13.0 g (62.4 mmols) of phosphorus pentachloride was further added thereto. The mixture was stirred for an hour. The solution was dropwise added at −60° to −70° C. to a mixture of 150 ml of dichloromethane, 27 ml of tert-butanol and 23 ml of pyridine. After the temperature was elevated to room temperature, the solution was washed, in sequence, with 1N hydrochloric acid aqueous solution and saturated sodium hydrogencarbonate aqueous solution. The solution was dried over anhydrous magnesium sulfate and the solvent was distilled off. The resulting oil was subjected to silica gel column chromatography and the column was eluted with dichloromethane-methanol (10:1) to give 6.8 g (43.6%) of t-butyl 2-bromo-2-(3-pyridyl)acetate.

Nuclear magnetic resonance spectrum (CDCl$_3$-TMS) δ (ppm): 1.45 (9H, s, $^t$Bu), 5.30 (1H, s, —CHBrCO$_2$), 7.20–7.50 (1H, m, pyridine (β)), 7.90 (1H, m, pyridine (γ)), 8.50–8.80 (2H, m, pyridine (α)).

Mass spectrum FAB (Pos.): 272, 274 (M+1).

(2) To 15 ml of acetonitrile were added 0.50 g (1.8 mmol) of t-butyl 2-bromo-2-(3-pyridyl)acetate and 0.37 g (1.8 mmol) of hydroxyphthalimide potassium salt. After heating to 70° C., the mixture was stirred for an hour. The solvent was distilled off under reduced pressure and 40 ml of water was added to the residue followed by extraction with ethyl acetate. After the extract was dried over anhydrous magnesium sulfate, the solvent was distilled off under reduced pressure to give 0.72 g of the residue. The residue was subjected to silica gel column chromatography and the column was eluted with dichloromethane-ethyl acetate (10:1) to give 0.28 g (43%) of tert-butyl 2-(3-pyridyl)-2-phthalimidoxyacetate.

Nuclear magnetic resonance spectrum (CDCl$_3$-TMS) δ (ppm): 1.45 (9H, s, $^t$Bu), 5.76 (1H, s,

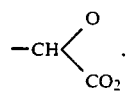

7.20–7.50 (1H, m, pyridine (β)), 7.77 (4H, s, phthalimide), 7.90–8.20 (1H, m, pyridine (γ)), 8.50–8.80 (2H, m, pyridine (α)).

Mass spectrum FAB (Pos.): 355 (M+1).

(3) After 0.22 g (0.62 mmol) g of tert-butyl 2-(3-pyridyl)-2-phthalimidoxyacetate was added to 5 ml of dichloromethane, the mixture was cooled to −70° C. to −60° C. After 0.032 ml (0.60 mmol) of methylhydrazine was added to the mixture, the temperature was elevated to 0° C. followed by stirring for 2 hours. The precipitated crystals were removed by filtration. The solvent was distilled off to give 0.17 g of the residue. The residue was subjected to silica gel column chromatography and the column was eluted with dichloromethane-ethyl acetate (2:1) to give 0.08 g (57.1%) of tert-butyl 2-(3-pyridyl)-2-aminooxyacetate.

Nuclear magnetic resonance spectrum (CDCl$_3$-TMS) δ (ppm): 1.40 (9H, s, $^t$Bu), 5.04 (1H, s, —CH), 5.65 (2H, br, NH$_2$), 7.10–7.30 (1H, m, pyridine (β)), 7.60–7.80 (1H, m, pyridine (γ)), 8.40–8.70 (2H, m, pyridine (α)).

Mass spectrum FAB (Pos.): 225 (M+1).

(7) After 0.30 g (1.34 mmol) of tert-butyl 2-(3-pyridyl)-2-aminooxyacetate and 0.55 g (1.33 mmol) of 2-(2-tritylaminothiazol-4-yl)-2-oxoacetic acid were added to 25 ml of methanol, the mixture was stirred for 3 hours. The precipitated crystals were taken out by filtration to give 0.25 g of the product. The filtrate was further distilled off under reduced pressure. After adding ether to the residue, the precipitated crystals were taken out by filtration and washed with ether to give 0.31 g of (Z)-2-(2-(tritylaminothiazol-4-yl)-[[(tert-butoxycarbonyl)(3-pyridyl)methoxy]imino]acetic acid.(total yield: 0.56 g (68.3%)).

Nuclear magnetic resonance spectrum (CDCl$_3$-TMS) δ (ppm): 1.39 (9H, s, $^t$Bu), 5.81 (1H, s,

6.79 (1H, s, 5-position at the thiazol), 7.14–7.60 (16H, m, pyridine (β), Tr), 7.91 (1H, d, 8 Hz, pyridine (γ)), 8.57 (1H, d, 4 Hz, pyridine (α)), 8.82 (1H, s, pyridine (α)).

Mass spectrum FAB (Pos.): 621 (M+1).

(5) After 1.0 g (1.6 mmol) of (Z)-2-(2-tritylaminothiazol-4-yl)-[[(tert-butoxycarbonyl)(3-pyridyl)methoxy]imino]acetic acid and 0.37 g (1.77 mmol) of phosphorus pentachloride were added to 25 ml of dichloromethane, the mixture was stirred at 5° C. for 30 minutes. The resulting solution was dropwise added to a solution containing 0.65 g (1.6 mmol) of p-methoxybenzyl 7-amino-3-chloromethyl-3-cephem-4-carboxylate hydrochloride and 1.3 ml of pyridine in 30 ml of dichloromethane. After stirring for an hour below −20° C.; the solution was cooled to −40° C. After adding 50 ml of 1N hydrochloric acid, the temperature was reverted to room temperature. The dichloromethane layer was taken out, washed with saturated sodium chloride aqueous solution and dried over anhydrous magnesium sulfate. The solvent was distilled off and the residue was subjected to silica gel column chromatography. The column was eluted with dichloromethane-methanol (10:1) to give 0.90 g (57.7%) of p-methoxybenzyl 7β-[(Z)-2-(2-tritylamino-4-thiazolyl)-2-[[(R S)-(tert-butoxycarbonyl)(3-pyridyl)methoxy]imino]acetamido]-3-chloromethyl-3-cephem-4-carboxylate.

Nuclear magnetic resonance spectrum (CDCl$_3$-TMS) δ (ppm): 1.36, 1.44 (9H, s each, $^t$Bu), 3.30–3.65 (2H, m, CH$_2$ at the 2-position), 3.82 (3H, s, OMe), 4.40–4.60 (2H, m, 3-CH$_2$Cl), 5.02 (1H, OCH<), 5.22–5.26 (1H, m, 6-position), 5.30 (2H, s,

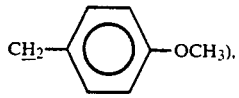

5.84–5.94 (1H, m, 7-position), 6.80, 6.82 (1H, s each, 5-position at the thiazole), 6.90 (1H, d, 8 Hz, pyridine (β)), 7.30 (19H, m, Trityl,

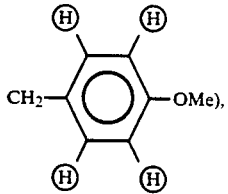

7.85 (1H, pyridine (γ)), 8.68 (2H, m, pyridine (α)).

Mass spectrum FAB (Pos.): 972 (M+1).

(6) After 0.18 g (0.62 mmol) of 4-carboxy-3-hydroxy-5-mercapto-isothiazole tripotassium salt and 0.42 g (1.24 mmol) of tetra-n-butylammonium hydrogen-sulfate were added to a mixture of 5 ml of dichloromethane and 5 ml of water at room temperature, 0.50 g (0.51 mmol)

of p-methoxybenzyl 7β-[(Z)-2-(2-tritylamino-4-thiazolyl)-2-[[(R S)-(tert-butoxycarbonyl)(3-pyridyl)methoxy]imino]acetamido]-3-chloromethyl-3-cephem-4-carboxylate was added to the mixture. After stirring at room temperature for 5 hours, the dichloromethane phase was separated and washed in sequence with water, 1N hydrochloric acid and saturated sodium chloride aqueous solution. After drying over anhydrous magnesium sulfate, the solvent was distilled off under reduced pressure. The residue was subjected to silica gel column chromatography and the column was eluted with chloroform-methanol (10:1) to give 0.30 g (52.6%) of p-methoxybenzyl 7β-[(Z)-2-(2-tritylamino-4-thiazolyl)-2-[[(R S)-(tert-butoxycarbonyl)(3-pyridyl)methoxy]imino]acetamido]-3-[[(4-carboxy-3-hydroxy-5-isothiazolyl)thio]methyl]-3-cephem-4-carboxylate.

Nuclear magnetic resonance spectrum (DMSO-$d_6$-TMS) δ (ppm): 1.40 (9H, s, $^t$Bu), 3.30–3.65 (2H, m, 2-position), 3.75 (3H, s, OMe), 5.06–5.20 (1H, m, 6-position), 5.14 (2H, s, CH$_2$S), 5.18 (2H, s,

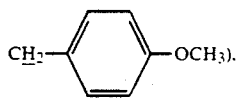

5.58 (1H, s each, OCH), 5.60–5.72 (1H, m, 7-position), 6.66, 6.70 (1H, s each, 5-position at the thiazole), 6.90 (1H, d, 8 Hz, pyridine (β)), 7.20–7.40 (18H, m, Trityl,

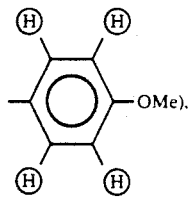

7.84 (1H, m, pyridine (γ)), 8.60 (2H, m, pyridine (α)), 8.90 (1H, s, NH), 9.52, 9.62 (1H, d each, CONH).

Mass spectrum FAB (Pos.): 1111 (M+1).

(7) After 0.30 g (0.30 mmol) of the compound obtained in (6), 2 ml of anisole and 8 ml of trifluoroacetic acid were added to 30 ml of dichloromethane under ice cooling, the mixture was stirred for an hour. The stirring was continued at room temperature for further an hour. The solvent was distilled off under reduced pressure and ether was added to the residue to make powders. The powders were filtered to give 0.23 g (82.1%) of 7β-[(Z)-2-(2-tritylamino-4-thiazolyl)-2-[[(R S)-(tert-butoxycarbonyl)(3-pyridyl)methoxy]imino]acetamido]-3-[[(4-carboxy-3-hydroxy-5-isothiazolyl)thio]methyl]-3-cephem-4-carboxylic acid.

Nuclear magnetic resonance spectrum (DMSO-$d_6$-TMS) δ (ppm): 1.40 (9H, s, $^t$Bu), 3.50–3.75 (2H, m, 2-position), 4.05–4.30 (2H, m, —CH$_2$S), 5.68 (1H, s, OCH), 5.75–5.85 (1H, m, 7-position), 6.80, 6.84 (1H, s each, 5-position at the thiazol), 7.35 (16H, m, pyridine (β), Trityl), 7.90 (1H, m, pyridine (γ)), 8.50–8.70 (2H, m, pyridine (α)), 9.60, 9.68 (1H, d each, CONH)

Mass spectrum FAB (Pos.): 749 (M+1).

(8) After 0.22 g of the compound obtained in Example 6 (7) was added to 25 ml of trifluoroacetic acid, the mixture was stirred at room temperature for an hour. The reaction mixture was cooled to 5° C. and 6 ml of water was added thereto. After stirring at 5° C., the temperature was reverted to room temperature followed by stirring for 2 hours. The solvent was distilled off under reduced pressure and ether was added to the residue to make powders. To the powders was added 100 ml of water and then 0.20 g of sodium hydrogencarbonate. The mixture was adsorbed to DIAION HP20 followed by elution with water-methanol. The fractions containing the desired product were collected. After concentration, the concentrate was freeze dried to give 90 mg (52.9%) of trisodium 7β-[(Z)-2-(2-amino-4-thiazolyl)-2-[[(R S)-(carboxy)(3-pyridyl)methoxy]imino]acetamido]-3-[[(4-carboxy-3-hydroxy-5-isothiazolyl)thio]methyl]-3-cephem-4-carboxylate.

Nuclear magnetic resonance spectrum (DMSO-$d_6$-TMS) δ (ppm): 3.36–3.80 (2H, m, 2-position), 4.24–4.32 (2H, m, —CH$_2$ at the 3-position), 5.14–5.20 (1H, m, 6-position), 5.76, 5.78 (1H, s each, OCH), 5.80–5.85 '1H, m, 7-position), 6.82, 6.86 (1H, s each, 5-position at the thiazol), 7.50–7.65 (1H, m, pyridine (β)), 8.00–8.10 (1H, m, pyridine (γ)), 8.70 (2H, d, 27 Hz, pyridine (α)), 9.62, 9.70 (1H, d each, 5 Hz, CONH).

Mass spectrum FAB (Pos.): 693 (M+1).

Infrared absorption spectrum cm$^{-1}$: 1780 (β-lactam).

EXAMPLE 9

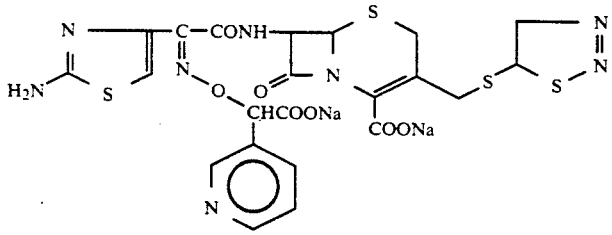

(1) After 2.3 g (2.37 mmols) of p-methoxybenzyl 7β-[(Z)-2-(2-tritylamino-4-thiazolyl)-2-[[(R S)-(tert-butoxycarbonyl)(3-pyridyl)methoxy]imino]acetamido]-3-chloromethyl-3-cephem-4-carboxylate, 0.40 g (2.67 mmols) of sodium iodide and 10 ml of acetone were added to 150 ml of carbon tetrachloride, the mixture was stirred at room temperature for an hour. After 100 ml of chloroform was added to the reaction mixture, washing was carried out in sequence with water and then with saturated sodium chloride aqueous solution. After drying over anhydrous magnesium sulfate, the solvent was distilled off under reduced pressure to give 2.25 g (89.3%) of p-methoxybenzyl 7β-[(Z)-2-(2-tritylamino-4-thiazolyl)-2-[[(R S)-(tert-butoxycarbonyl)(3-pyridyl)methoxy]imino]acetamido-3-iodomethyl]-3-cephem-4-carboxylate.

Nuclear magnetic resonance spectrum (CDCl$_3$-TMS) δ (ppm): 1.38, 1.46 (9H, s each, $^t$Bu), 3.30–3.80 (2H, m, 2-position), 3.84 (3H, s, OMe), 4.40–4.60 (2H, m, CH$_2$ at the 3-position), 5.00–5.06 (1H, m, 6-position), 5.20–5.30 (1H, m, OCH—), 5.80–6.00 (1H, m, 7-position), 6.85, 6.84 (1H, s each, 5-position at the thiazole), 6.90 (1H, d, 8 Hz, pyridine (β)), 7.10–7.60 (19H, m, Trityl,

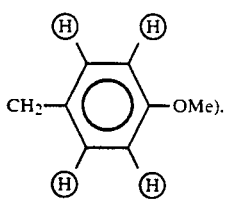

7.85 (1H, m, pyridine (γ)), 8.70 (2H, m, pyridine (λ)).
Mass spectrum FAB (Pos.): 1063 (m+1).

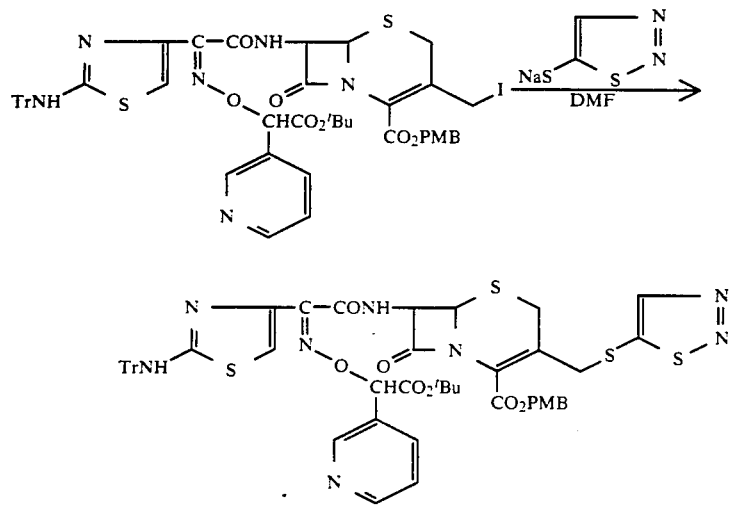

(2) After 0.75 g (0.705 mmol) of the compound obtained in (1) and 0.11 g (0.78 mmol) of 5-mercapto-1,2,3-thiadiazole trisodium salt were added to 8 ml of dimethylformamide at 5° C., the mixture was stirred at 5° C. for 30 minutes. After 50 ml of ethyl acetate was added thereto, the mixture was washed with 1N hydrochloric acid and dried over anhydrous magnesium sulfate. Thereafter, the solvent was distilled off under reduced pressure. The residue was subjected to silica gel column chromatography and the column was eluted with dichloromethane-ethyl acetate (4:1) to give 0.12 g (16.2%) of p-methoxybenzyl 7β-[(Z)-2-(2-tritylamino-4-thiazolyl)-2-[[(R S)-(tert-butoxycarbonyl)(3-pyridyl)methoxy]imino]acetamido]-3-[(1,2,3-thiadiazol-5-yl)thiomethyl]-3-cephem-4-carboxylate.

Nuclear magnetic resonance spectrum (CDCl₃-TMS) δ (ppm): 1.40, 1.45 (9H, s each, ᵗBu), 3.40–3.70 (2H, m, 2-position), 3.85 (3H, s, OMe), 4.15 (2H, s, CH₂ at the 3-position), 5.00–5.20 (1H, m, 6-position), 5.15 (1H, s, OCH—), 5.80–5.95 (1H, m, 7-position), 6.80 (1H, s, 5-position at the thiazole), 6.95 (1H, s, pyridine (β)), 7.20–7.50 (19H, m, Trityl,

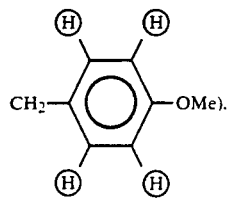

8.45 (1H, s, 4-position at the thiadiazole), 8.70 (2H, m, pyridine (α)).
Mass spectrum FAB (Pos.): 1053 (M+1).

(3) After 0.12 g (0.11 mmol) of the compound obtained in (2), 1 ml of anisole and 3 ml of trifluoroacetic acid were added to 1 ml of dichloromethane under ice cooling, the mixture was stirred for an hour. The solvent was distilled off under reduced pressure and ether was added to the residue to make powders. The powders were filtered to give 0.09 g of 7β-[(Z)-2-(2-tritylamino-4-thiazolyl)-2-[[(R S)-(tert-butoxycarbonyl)(3-pyridyl)methoxy]imino]acetamido]-3-[(1,2,3-thiadiazol-5-ylthio)methyl]-3-cephem-4-carboxylic acid.

Nuclear magnetic resonance spectrum (DMSO-d₆-TMS) δ (ppm): 1.38, 1.40 (9H, s, ᵗBu), 3.40–3.80 (2H, m, 2-position), 5.10–5.20 (1H, m, 6-position), 5.64 (1H, s, OCH—), 5.70–5.80 (1H, m, 7-position), 6.80, (1H, s, 5-position at the thiazole), 7.20, 7.40 (16H, m, Trityl, pyridine (β)), 7.96 (1H, m, pyridine (γ)), 8.60–8.70 (2H, m, pyridine (α)), 8.88 (1H, s, 4-position at the thiadiazole), 9.55, 9.65 (1H, d each, 5 Hz, CONH).
Mass spectrum FAB (Pos.): 932 (M+1).

(4) After 0.07 g of the compound obtained in (3) was added to 7 ml of trifluoroacetic acid, the mixture was stirred at room temperature for an hour. The reaction mixture was cooled to 5° C. and 1.5 ml of water was added thereto. After stirring for 40 minutes, stirring was continued at room temperature for further 3 hours. The solvent was distilled off under reduced pressure and ether was added to the residue to make powders. The powders were taken out by filtration. To the powders was added 50 ml of water and then sodium hydrogencarbonate. After adjusting pH to 7, the mixture was adsorbed to DIAION HP20 followed by elution with water and then with water-methanol. The fractions containing the desired product were collected. After concentration, the concentrate was freeze dried to give 9 mg (17.6%) of disodium 7β-[(Z)-2-(2-amino-4-thiazolyl)-2-[[(R S)-(carboxy)(3-pyridyl)methoxy]imino]acetamido]-3-[(1,2,3-thiadiazol-5-yl)thio)methyl]-3-cephem-4-carboxylate.

Nuclear magnetic resonance spectrum (DMSO-d₆-TMS) δ (ppm): 3.40–4.80 (2H, m, 2-position), 4.20–4.30 (2H, m, CH₂ at the 3-position), 5.15–5.20 (1H, m, 6-position), 5.75, 5.76 (1H, s each, OCH—), 5.70–5.85 (1H, m, 7-position), 6.80, 6.84 (1H, s each, 5-position at the thiazole), 7.50–7.60 (1H, m, pyridine (β)), 7.95–8.05 (1H, m, pyridine (β)), 8.60–8.80 (2H, m, pyridine (α)), 8.88 (1H, s, 4-position at the thiadiazole), 9.65, 9.72 (1H, s each, 5 Hz, CONH).

Mass spectrum FAB (Pos.): 679 (M+1).

EXAMPLE 10

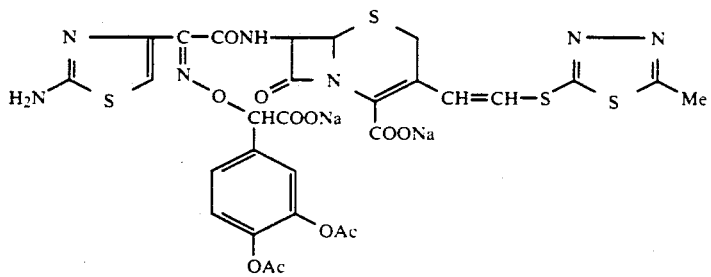

(1) After 1.88 g (2.22 mmols) of (Z)-2-(2-tritylamino-4-thiazolyl)-2-[[(diphenylmethyloxycarbonyl)(3,4-diacetoxyphenyl)methyl]oxyimino]acetic acid and 0.51 g (2.45 mmols) of phosphorus pentachloride were added at 5° C. to 35 ml of dichloromethane, the mixture was stirred for 30 minutes. The solution was added dropwise to a solution containing 1.22 g (2.22 mmols) of diphenylmethyl 7-amino-3-[(E Z)-2-(4-methylphenylsulfonyloxy)vinyl]-3-cephem-4-carboxylate and 1.8 ml (2.23 mmols) of pyridine in 30 ml of dichloromethane at a temperature below −40° C. The solution was stirred for an hour at a temperature below −20° C. Then, the solution was cooled to below −40° C. and 1N hydrochloric acid was added thereto. The temperature was elevated to room temperature and the dichloromethane phase was fractionated. After washing with saturated sodium chloride aqueous solution, the dichloromethane phase was dried over anhydrous magnesium sulfate. The solvent was distilled off under reduced pressure to give 3.2 g of the residue. The residue was subjected to silica gel column chromatography and the column was eluted with dichloromethane-ethyl acetate (10:1) to give 1.63 (52.6%) g of diphenylmethyl 7β-[(Z)-2-(2-tritylamino-4-thiazolyl)-2-[[(R S)-(diphenylmethyloxycarbonyl)(3,4-diacetoxyphenyl)methoxy]imino]acetamido]-3-[(E Z)-2-(4-methylphenylsulfonyloxy)vinyl]-3-cephem-4-carboxylate.

Nuclear magnetic resonance spectrum (CDCl$_3$-TMS) δ (ppm): 2.12, 2.24, 2.30, 2.30 (6H, s each, 2 x OAc), 2.40, 2.42 (3H, s each, tosyl CH$_3$), 3.06–3.24 (2H, m, 2-position), 4.86, 4,95 (1H, d each, 5 Hz, 6-position), 5.70–5.90 (1H, m, 7-position), 6.00, 6.15 (1H, d each, O—CHCOO—), 6.80–7.50 (45H, m, Tr, —CH=CH—, 5-position at the thiazole, CH at the benzhydryl,

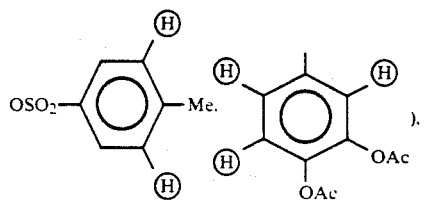

7.70–7.80 (2H, m,

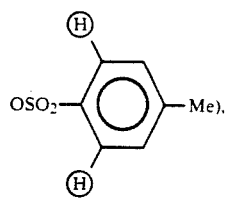

8.22 (1H, d, 8 Hz, CONH)

Mass spectrum FAB (Pos.): 1390 (M+1).

(2) After 1.50 g (1.08 mmol) of the compound obtained in (1), 0.29 g (2.19 mmols) of 2-methyl-5-mercapto-1,3,4-thiadiazole and 0.37 ml (2.17 mmols) of diisopropylethylamine were added to 50 ml of dimethylformamide at 5° C., the mixture was stirred at room temperature for 3.5 hours and then at 40° C. for an hour. The solvent was distilled off under reduced pressure and 100 ml of ethyl acetate was then added to the residue. After washing sequentially with water, 0.1N hydrochloric acid, saturated sodium hydrogencarbonate aqueous solution and then saturated sodium chloride aqueous solution, the organic phase was dried over anhydrous magnesium sulfate. The solvent was distilled off under reduced pressure to give 1.37 g of the residue. The residue was subjected to silica gel column chromatography and the column was eluted with dichloromethane-ethyl acetate (10:1) to give 0.32 g (22.0%) of diphenylmethyl 7β-[(Z)-2-(2-tritylamino-4-thiazolyl)-2-[[(R S)-diphenylmethyloxycarbonyl)(3,4-diacetoxyphenyl)methoxy]imino]acetamido]-3-[(E Z)-2-(2-methyl-1,3,4-thiadiazol-5-yl)thiovinyl]-3-cephem-4-carboxylate.

Nuclear magnetic resonance spectrum (CDCl$_3$-TMS) δ (ppm): 2.20–2.40 (6H, m, OAc x 2), 2.76 (3H, s, CH$_3$), 3.20–3.60 (2H, m, 2-position), 4.90–5.00 (1H, m, 6-position), 5.80–6.00 (1H, m, 7-position), 6.00–6.14 (1H, s each, —CH—COO), 6.80–7.80 (43H, m, Trityl, —CH=CH—, 5-position at the thiazole, benzhydryl,

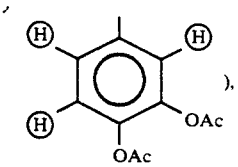

8.00–8.20 (1H, m, CONH).

Mass spectrum FAB (Pos.): 1350 (M+1).

(3) After 0.32 g (0.24 mmol) of the compound obtained in (2) was added to 4 ml of dichloromethane, 12 ml of trifluoroacetic acid and 4 ml of anisole were further added thereto followed by stirring at room temperature for 3 hours. The solvent was distilled off under reduced pressure and ether was added to the residue to make powders. The powders were filtered and washed with ether to give 0.22 g (91.3%) of 7β-[(Z)-2-(2-tritylamino-4-thiazolyl)-2-[[(R S)-(carboxy)(3,4-diacetoxyphenyl)methoxy]imino]acetamido]-3-[(E,Z)-2-(2-methyl-1,3,4-thiadiazol-5-yl)thiovinyl]-3-cephem-4-carboxylic acid.

Nuclear magnetic resonance spectrum (DMSO-d$_6$-TMS) δ (ppm): 2.22, 2.26 (6H, each s, OAc x 2), 2.72 (3H, s, CH$_3$), 3.60-3.80 (2H, m, 2-position), 5.10-5.20 (1H, m, 6-position), 5.55, 5.60 (1H, s each,

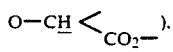

5.60-5.85 (1H, m, 7-position), 6.70-7.40 (21H, m, Trityl,

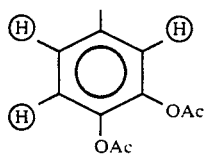

5-position at the thiazole, —C$\underline{H}$=C$\underline{H}$—), 9.40-9.80 (1H, m, CONH)

Mass spectrum FAB (Pos.): 1018.

(4) After 0.10 g of the compound obtained in (3) was added to a mixture of 4 ml of trifluoroacetic acid and 1 ml of water, the mixture was stirred at room temperature for 18 hours. The solvent was distilled off under reduced pressure and ether was added to the residue to make powders. The powders were taken out by filtration and the filtered powders were added to 70 ml of water. Sodium hydrogencarbonate was added to the mixture to dissolve the powders. The solution was adsorbed to DIAION HP20 followed by elution with water and then with methanol-water. The fractions containing the desired product were collected. After concentration, the concentrate was freeze dried to give 33 mg (43.4%) of disodium 7β-[(Z)-2-(2-amino-4-thiazolyl)-2-[[(R S)-(carboxy)(3,4-diacetoxyphenyl)methoxy]imino]acetamido]-3-[(E Z)-2-(2-methyl-1,3,4-thiadiazol-5-yl)thiovinyl]-3-cephem-4-carboxylate.

Nuclear magnetic resonance spectrum (DMSO-d$_6$-TMS) δ (ppm): 2.24 (6H, s, OAc x 2), 2.70 (3H, s, CH$_3$), 5.00-5.20 (1H, m, 6-position), 5.25 (1H, s, O—CH—), 5.60-5.75 (1H, m, 7-position), 6.80-7.40 (6H, m,

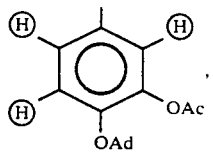

5-position at the thiazole, —C$\underline{H}$—C$\underline{H}$—).

Mass spectrum FAB (Pos.): 776, 798 (Neg.), 774, 796

EXAMPLE 11

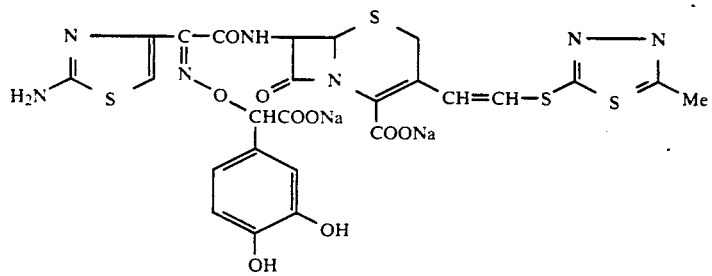

After 0.18 g of 7β-[(Z)-2-(2-amino-4-thiazolyl)-2-[[(R S)-(carboxy)(3,4-diacetoxyphenyl)methoxy]imino]acetamido]-3-[(E Z)-2-(2-methyl-1,3,4-thiadiazol-5-yl)thiovinyl]-3-cephem-4-carboxylic acid was added to 10 ml of saturated sodium hydrogencarbonate aqueous solution, the mixture was stirred at room temperature for 12 hours. To the reaction mixture was added 100 ml of water. The mixture was adsorbed to DIAION HP20 followed by elution with water and then with water-methanol. The fractions containing the desired product were collected. After concentration, the concentrate was freeze dried to give 24 mg of disodium 7β-[(Z)-2-(2-amino-4-thiazolyl)-2-[[(R S)-(carboxy)-(3,4-dihydroxyphenyl)methoxy]imino]acetamido]-3-[(E Z)-2-(2-methyl-1,3,4-thiadiazol-5-yl)thiovinyl]-3-cephem-4-carboxylate.

Nuclear magnetic resonance spectrum (D$_2$O-TMS) δ (ppm): 2.74 (3H, s, Me), 3.30-3.80 (2H, m, 2-position), 5.10 (1H, s, 6-position), 5.40 (1H, s, OCH), 5.65-5.75 (1H, m, 7-position), 6.50-7.50 (5H, m,

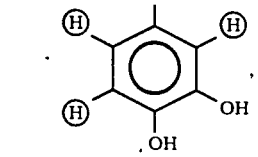

—C$\underline{H}$=C$\underline{H}$—).

Mass spectrum FAB (Neg.): 734 (M-1).

Infrared absorption spectrum cm$^{-1}$: 1772 (β-lactam).

EXAMPLE 12

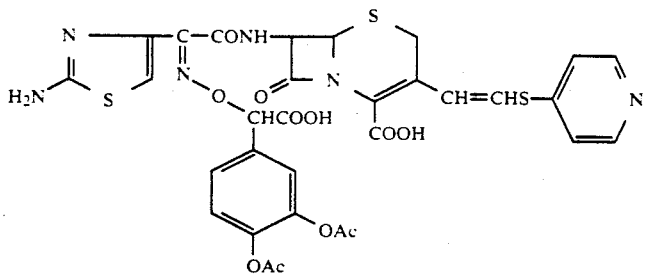

(1) After 2.5 g (1.80 mmol) of diphenylmethyl 7β-[(Z)-2-(2-tritylamino-4-thiazolyl)-2-[[(R S)-(diphenylmethyloxycarbonyl)(3,4-diacetoxyphenyl)methoxy]imino]acetamido]-3-[(E Z)-2-(p-toluenesulfonyloxy)vinyl]-3-cephem-4-carboxylate 0.40 g (3.60 mmols) of 4-mercaptopyridine and 0.62 ml (3.60 mmols) of diisopropylethylamine were added at 5° C. to 80 ml of dimethylformamide, the mixture was stirred at 5° C. for an hour and then at room temperature for 2 hours. The solvent was distilled off under reduced pressure and 200 ml of ethyl acetate was added to the residue. After washing with water and then with saturated sodium chloride aqueous solution, the mixture was dried over anhydrous magnesium sulfate and the solvent was distilled off under reduced pressure. The residue was subjected to silica gel column chromatography and the column was eluted with dichloromethane-ethyl acetate (2:1) to give 0.50 g of diphenylmethyl 7β-[(Z)-2-tritylamino-4-thiazolyl)-2-[[(R S)-(diphenylmethyloxycarbonyl)(3,4-diacetoxyphenyl)methoxy]imino]acetamido]-3-[(E Z)-2-(4-pyridyl)thiovinyl]-3-cephem-4-carboxylate.

Nuclear magnetic resonance spectrum (DMSO-d$_6$-TMS) δ (ppm): 2.24, 2.28 (6H, s each, OAc x 2), 3.16–3.40 (2H, m, 2-position), 5.10–5.25 (1H, m, 6-position), 5.74 (1H, s, OCH), 5.66–5.86 (1H, m, 7-position), 6.70–7.70 (45H, m, Trityl,

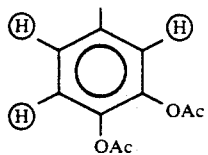

—CH=CH—, 5-position at the thiazole, CH at the benzhydryl), 8.35–8.48 (2H, m, pyridine (α)), 8.92 (1H, s, TrNH), 9.64, 9.76 (1H, s each, CONH)

Mass spectrum FAB (Pos.): 1329 (M+1).

(2) After 0.50 g (0.37 mmol) of the compound obtained in (1), 4 ml of anisole and 12 ml of trifluoroacetic acid were added to 4 ml of dichloromethane, the mixture was stirred for 4 hours. The solvent was distilled off under reduced pressure and ether was added to the residue to make powders. The powders were taken out by filtration give 0.38 g of crude 7β-[(Z)-2-(2-tritylamino-4-thiazolyl)-2-[[(R S)(carboxy)(3,4-diacetoxyphenyl)methoxy]imino]acetamido]-3-[(E Z)-2-(4-pyridylthio)vinyl]-3-cephem-4-carboxylic acid.

Nuclear magnetic resonance spectrum (DMSO-d$_6$-TMS) δ (ppm): 2.26 (6H, s, OAc x 2), 3.60–3.80 (2H, m, 2-position), 5.15–5.30 (1H, m, 6-position), 5.50–5.65 (1H, m, OCH), 5.80–5.88 (1H, m, 7-position), 6.00–6.95 (3H, m, —CH=CH—, 5-position at the thiazole), 7.05–7.50 (18H, m, Trityl,

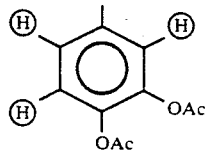

7.60–7.80 (2H, m, pyridine (β)), 8.58 (2H, d, 5 Hz, pyridine (α)), 9.60, 9.70 (1H, d each, CONH).

Mass spectrum FAB (Pos.): 996 (M+1).

(3) After 0.38 g of the compound obtained in (2), was added to 10 ml of 80% acetic acid, the mixture was stirred at 40° C. for 7 hours and then at room temperature for 3 days. The solvent was distilled off under reduced pressure and ether was added to the residue to make powders. The powders were taken out by filtration give 0.34 g of crude 7β-[(Z)-2-(2-amino-4-thiazolyl)-2-[[(R S)-(carboxy)(3,4-diacetoxyphenyl)methoxy]imino]acetamido]-3-[(E Z)-2-(4-pyridylthio)vinyl]-3-cephem-4-carboxylic acid.

Nuclear magnetic resonance spectrum (DMSO-d$_6$-TMS) δ (ppm): 2.30 (6H, s, OAc x 2), 3.60–3.80 (2H, m, 2-position), 5.20–5.30 (1H, m, 6-position), 5.50–5.65 (1H, m, OCH), 5.80–5.90 (1H, m, 7-position), 6.70–7.00 (3H, m, H at the thiazole, —CH=CH—), 7.00–7.50 (3H, m,

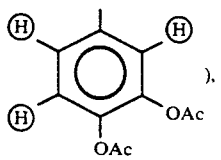

7.60–7.80 (2H, m, pyridine H (β)), 8.50–8.65 (2H, m, pyridine (α)), 9.58, 9.74 (1H, d each, 5 Hz, CONH).

Mass spectrum FAB (Pos.): 755 (M+1).

Infrared absorption spectrum cm$^{-1}$: 1762 (β-lactam)

EXAMPLE 13

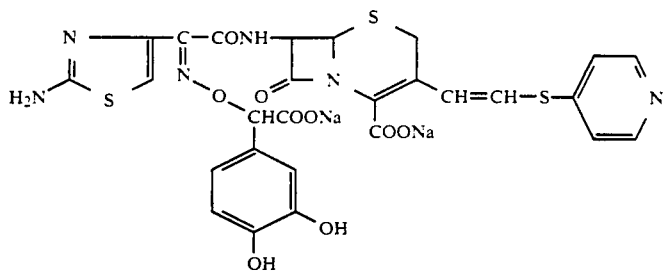

After 0.20 g of 7β-[(Z)-2-(2-amino-4-thiazolyl)-2-[[(R S)-(carboxy)(3,4-diacetoxyphenyl)methoxy]imino]acetamido]-3-[(E Z)-2-(4-pyridylthio)vinyl]-3-cephem-4-carboxylic acid was added to 30 ml of saturated sodium hydrogencarbonate aqueous solution, 0.10 g of sodium hydrogencarbonate was added to the solution. The mixture was stirred at room temperature for 4 hours. To the reaction mixture was added 30 ml of water. The mixture was adsorbed to DIAION HP20 followed by elution with water and then with water-methanol. The fractions containing the desired product were collected. After concentration, the concentrate was freeze dried to give 90 mg (50.8%) of disodium 7β-[(Z)-2-(2-amino-4-thiazolyl)-2-[[(R S)-(carboxy)(3,4-dihydroxyphenyl)methoxy]imino]acetamido]-3-[(E Z)-2-(4-pyridylthio)vinyl]-3-cephem-4-carboxylate.

Nuclear magnetic resonance spectrum (DMSO-$d_6$-TMS) δ (ppm): 3.40–3.80 (2H, m, 2-position), 5.04, 5.08 (1H, d each, 5 Hz, 6-position), 5.20, 5.26 (1H, s each, OCH), 5.30, 5.70 (1H, m, 7-position), 6.30–7.00 (5H, m,

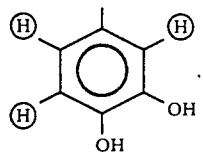

—CH=CH—), 7.20 (2H, s, OH x 2), 7.28–7.40 (2H, m, pyridine (β̄)), 8.30–8.45 (2H, m, pyridine (α)), 9.00 (2H, br, NH$_2$), 10.70 (1H, br, CONH).

Mass spectrum FAB (Pos.): 692, 761, 714.

Infrared absorption spectrum cm$^{-1}$: 1766 (β-lactam).

EXAMPLE 14

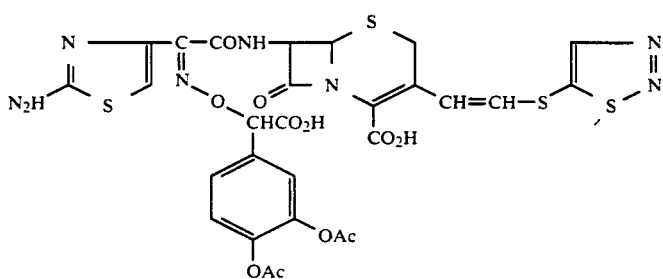

(1) To 60 ml of dimethylformamide were added at 5° C. 2.5 g (1.80 mmol) of diphenylmethyl 7-[(Z)-2-(2-tritylamino-4-thiazolyl)-2-[[(R S)-(diphenylmethyloxycarbonyl)(3,4-diacetoxyphenyl)methoxy]imino]acetamido]-3-[(E Z)-2-(p-toluenesulfonyloxy)vinyl]-3-cephem-4-carboxylate, 0.42 g (3.55 mmols) of 5-mercapto-1,2,3-thiadiazole and 0.62 ml (3.60 mmols)

of diisopropylethylamine. After the mixture was stirred at at room temperature for 3 hours, the solvent was distilled off under reduced pressure and 150 ml of ethyl acetate was added to the residue. After washing in sequence with water, 0.1N hydrochloric acid, saturated sodium hydrogencarbonate aqueous solution and then saturated sodium chloride aqueous solution, the mixture was dried over anhydrous magnesium sulfate and the solvent was distilled off under reduced pressure. The residue was subjected to silica gel column chromatography and the column was eluted with dichloromethane-ethyl acetate (10:1) to give 2.20 g (91.7%) of diphenylmethyl 7β-[(Z)-2-(2-tritylamino-4-thiazolyl)-2-[[(R˙ S)-(diphenylmethyloxycarbonyl)(3,4-diacetoxyphenyl)methoxy]imino]acetamido]-3-[E Z)-2-(1,2,3-thiadiazol-5-yl)thiovinyl]-3-cephem-4-carboxylate.

Nuclear magnetic resonance spectrum (DMSO-$d_6$-TMS) δ (ppm): 2.24, 2.28 (6H, s each, OAc x 2), 3.40–3.80 (2H, m, 2-position), 5.12–5.24 (1H, m, 6-position), 5.68–5.84 (1H, m, 7-position), 5.85, 5.88 (1H, s each, $$OCH <^{COO-}_{\phantom{x}}),$$

6.80–7.70 (45H, m, Trityl,

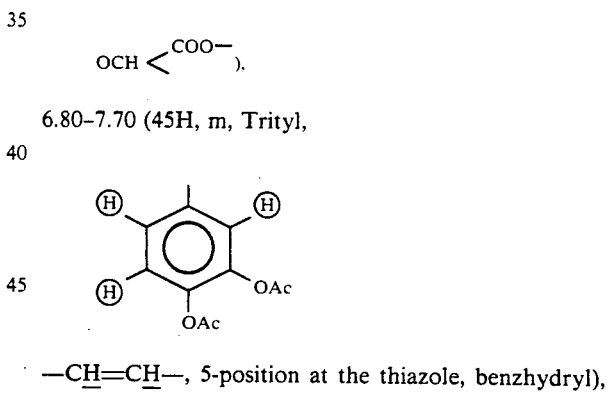

—CH=CH—, 5-position at the thiazole, benzhydryl), 8.90 (1H, s, TrNH), 8.98, 9.00 (1H, s each, 4-position at the thiadiazole), 9.65, 9.72 (1H, d each, 4 Hz, CONH).

Mass spectrum FAB (Pos.): 1336.

(2) After 2.2 g (1.65 mmol) of the compound obtained in (1), 20 ml of anisole and 80 ml of trifluoroacetic acid were added to 20 ml of dichloromethane, the mixture was stirred for 5 hours. The solvent was distilled off under reduced pressure and ether was added to the residue to make powders. The powders were taken out by filtration give 1.30 g of crude 7β-[(Z)-2-(2-tritylamino-4-thiazolyl)-2-[[(R S)-(carboxy)(3,4-diacetoxyphenyl)methoxy]imino]acetamido]-3-[(E Z)-2-(1,2,3-thiazol-5-yl)thiovinyl]-3-cephem-4-carboxylic acid.

Nuclear magnetic resonance spectrum (DMSO-$d_6$-TMS) δ (ppm): 2.22, 2.26 (6H, s each, OAc x 2), 3.40–3.80 (2H, m, 2-position), 5.13, 5.17 (1H, d each, 5 Hz, 6-position), 5.56 (1H, s, OCH), 5.65–5.74 (1H, m, 7-position), 6.70–7.10 (3H, m, —C$\underline{H}$=C$\underline{H}$—, 5-position at the thiazole), 7.30 (18H, m, Trityl

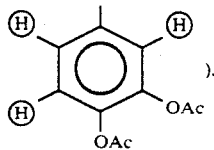

).

8.92 (1H, s, TrN$\underline{H}$), 9.00 (1H, s, 5-position at the thiadiazole), 9.50, 9.65 (1H, d each, CONH).

Mass spectrum FAB (Pos.): 1004.

(3) After 1.3 g (1.29 mmol) of the compound obtained in (2) was added to 60 ml of 80% acetic acid, the mixture was stirred at 40° C. for 8 hours and then at room temperature for 36 days. The solvent was distilled off under reduced pressure and ether was added to the residue to make powders. The powders were taken out by filtration give 0.97 g of crude 7β-[(Z)-2-(2-amino-4-thiazolyl)-2-[[(R S)-(carboxy)(3,4-diacetoxyphenyl)methoxy]imino]acetamido]-3-[(E Z)-2-(1,2,3-thiazol-5-yl)thiovinyl]-3-cephem-4-carboxylic acid.

Nuclear magnetic resonance spectrum (DMSO-$d_6$-TMS) δ (ppm): 2.24, 2.26 (6H, s each, OAc x 2), 3.56–4.00 (2H, m, 2-position), 5.18, 5.21 (1H, d each, 5 Hz, 6-position), 5.60 (1H, s,

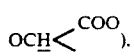

).

5.78–5.85 (1H, m, 7-position), 6.77, 6.82 (1H, s each, 5-position at the thiazole), 6.96–7.20 (2H, m, —C$\underline{H}$=C$\underline{H}$—), 7.20–7.50 (3H, m,

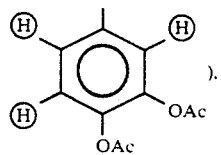

).

9.00 (1H, s each, 5-position at the thiazole), 9.56, 9.71 (1H, d each, 5 Hz, CONH).

Mass spectrum FAB (Pos.): 762 (M+1).

Infrared absorption spectrum cm$^{-1}$: 1776 (β-lactam).

EXAMPLE 15

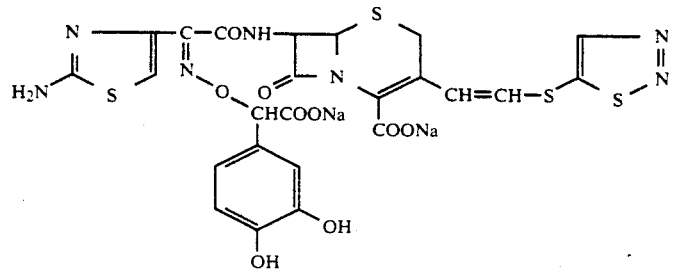

After 0.20 g (0.26 mmol) of 7β-[(Z)-2-(2-amino-4-thiazolyl)-2-[[(R S)-(carboxy)(3,4-diacetoxyphenyl)methoxy]imino]acetamido]-3-[(E Z)-2-(1,2,3-thiadiazol-5-yl)thiovinyl]-3-cephem-4-carboxylic acid was added to 30 ml of saturated sodium hydrogencarbonate aqueous solution, 0.10 g of sodium hydrogencarbonate was added to the solution followed by stirring at room temperature for 4 hours. To the reaction mixture was added 30 ml of water. The mixture was adsorbed to DIAION HP20 followed by elution with water and then with water-methanol. The fractions containing the desired product were collected. After concentration under reduced pressure, the concentrate was freeze dried to give disodium 7β-[(Z)-2-(2-amino-4-thiazolyl)-2-[[(RS)-(carboxy)(3,4-dihydroxyphenyl)methoxy]imino]acetamido]-3-[(EZ)-2-(1,2,3-thiadiazol-5-yl)thiovinyl]-3-cephem-4-carboxylate (143 mg) (yield: 79.4%).

Nuclear magnetic resonance spectrum (DMSO-$d_6$-TMS) δ (ppm): 3.40–3.70 (2H, m, 2-position), 5.00–5.10 (1H, m, 6-position), 5.08–5.12 (1H, m,

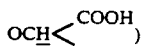

)

5.65–5.80 (1H, m, 7-position), 6.30~7.00 (5H, m,

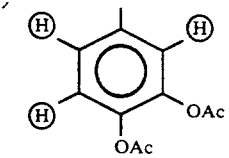

—C$\underline{H}$=C$\underline{H}$—), 8.86 (1H, s, 4-position at the thiadiazole).

Mass spectrum FAB (Pos.): 700 (1Na-salt).

Infrared absorption spectrum (KBr) (cm$^{-1}$): 1772 (β-lactam).

EXAMPLE 16

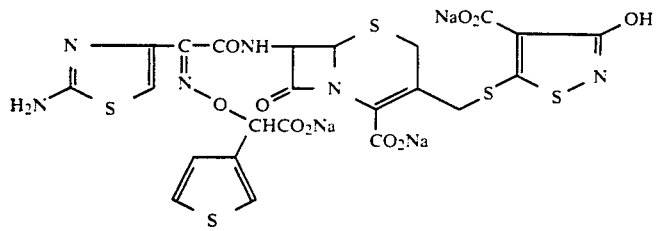

(1) Diphenylmethyl 2-(3-thienyl)-2-bromoacetate (200 mg) was dissolved in dimethylformamide (22 ml), potassium N-hydroxyphthalimidate (104 mg) was added thereto under ice-cooling, and then the resulting mixture was stirred for 1.5 hrs. Water was added to the reaction solution, the solution was extracted with ethyl acetate (×3). The organic layer was washed with saturated saline, and dried over anhydrous magnesium sulfate, and the solvent was filtered off to give an oil. The oil thus obtained was subjected to silica gel column chromatography eluting with benzene to obtain diphenylmethyl 2-(3-thienyl)-2-phthalimidoxyacetate (240 mg).

NMR spectrum (CDCl$_3$) δ(ppm); 6.08(1H, s), 6.92(1H, s), 7.04–7.38(12H, m), 7.48(1H, t), 7.62–7.74(4H, m).

Mass spectrum FAB(Pos.); 470(M+H).

(2) Diphenylmethyl 2-(3-thienyl)-2-phthalimidoxyacetate (210 mg) was dissolved in dichloromethane (4 ml). After cooling to −60° C., methyl hydrazine (0.023 ml) was added to the mixture to increase the temperature to 0° C., and stirred for 1 hr. The reaction mixture was filtered off and the solvent was evaporated to give diphenylmethyl 2-(3-thienyl)-2-aminooxyacetate (150 mg) as a caramel.

NMR spectrum (CDCl$_3$) δ(ppm); 5.38(1H, s), 5.50–6.05(2H, brs), 6.96(1H, s), 7.03–7.46(13H, m).

Mass spectrum FAB(Pos.); 340(M+H).

(3) Diphenylmethyl 2-(3-thienyl)-2-aminooxyacetate (140 mg) was dissolved in methanol (14 ml), and 2-(2-tritylaminothiazol-4-yl)-2-oxoacetic acid (171 mg) was added. After stirring the mixture for 1 hr. at the room temperature, and further stirring for 30 min. under ice-cooling to obtain a crystal, the crystal thus obtained was filtered off to give (Z)-2-(2-tritylamino-4-thiazolyl)-2-[(diphenylmethyloxycarbonyl)(3-thienyl)methyl]oxyiminoacetic acid (210 mg).

NMR spectrum (DMSO-d$_6$) δ(ppm); 2.98–3.70(1H, brs), 5.90(1H, s), 6.84(2H, s), 6.86–7.62(28H, m), 8.82(1H, s).

Mass spectrum FAB(Pos.); 736(M+H).

(4) (Z)-2-(2-tritylamino-4-thiazolyl)-2-[(diphenylmethyloxycarbonyl)(3-thienyl)methyl]oxyiminoacetic acid (1.90 g, 2.58 mmol) and phosphorus pentoxide (0.564 g, 2.71 mmol) were added to dichloromethane (11 ml) under ice-cooling, and then the resulting mixture was stirred for 30 min. Thus obtained solution was added at −60° C. to the solution of 4-methoxybenzyl 7-amino-3-chloromethyl-3-cephem-4-carboxylate (1.046 g, 2.58 mmol) and pyridine (1.04 ml, 12.9 mmol) in dichloromethane (30 ml) at −40° C. The reaction solution was allowed to −20° C. over 40 min. The reaction solution was cooled to −40° C., and 1N hydrochloric acid (12.9 ml) was added thereto. Water was added to the reaction solution, the solution was extracted with dichloromethane (×3), the organic layer was washed with a saturated saline and dried over anhydrous magnesium sulfate, and then the solvent was evaporated to give a caramel (3.50 g). The caramel was subjected to silica gel column chromatography eluting with hexane-ethyl acetate to obtain (4-methoxybenzyl) 7β-[(Z)-2-(2-tritylamino-4-thiazolyl)-2-[[(R S)-(diphenylmethyloxycarbonyl)(3-thienyl)methoxy]imino]acetamido]-3-cloromethyl-3-cephem-4-carboxylate (2.62 g).

NMR spectrum (CDCl$_3$) δ(ppm); 3.21, 3.46(2H,

3.84(3H, s, CH$_3$), 4.44, 4.50(2H, each of q, —CH$_2$Cl), 4.89, 4.94(1H, each of d, CH at 6-position), 5.22, 5.24(2H, each of s, CO$_2$—CH$_2$), 5.85, 5.86(1H, each of dd, CH at 7-position), 6.14, 6.18(1H, each of s, N—O—CH), 6.75(1H, s, —CO$_2$ —CHφ$_2$), 6.82–7.04(3H, br), 7.06–7.54(31H, br), 8.10, 8.31(1H, each of d, CONH)$_6$)

Mass spectrum FAB(Pos.); 1086(M+H).

(5) Tetrabutylammonium hydrogen sulfate (375 mg) and tripotassium 3-hydroxy-5-mercaptoisothiazolyl-4-carboxylate (161 mg) were dissolved in water (5 ml) and dichloromethane (5 ml), to the mixture thus formed 7β-[(Z)-2-tritylamino-4-thiazolyl)-2-[[(R S)-(diphenylmethyloxycarbonyl)(3-thienyl)methoxy]imino]acetamido]-3-chloromethyl-3-cephem-4-carboxylate (500 mg) and potassium iodide (7.6 mg) were added at the room temperature, and then the resulting mixture was stirred for 23 hrs. The mixture was separated into organic layer and aqueous layer, the organic layer was washed with water and a saturated saline, dried over magnesium sulfate, and then the solvent was evaporated to give tetrabutylammonium (4-methoxybenzyl) 7β-(Z)-2-(2-tritylamino-4-thiazolyl)-2-[[(R S)-diphenylmethyl-oxycarbonyl)(3-thienyl)methoxy]imino]acetamido]-3-[[(4-carboxy-3-hydroxy-5-iso-thiazolyl)thio]methyl-3-cephem-4carboxylate (800 mg) as a crude crystal.

(6) (4-Methoxybenzyl) 7β-[(Z)-2-(2-tritylamino-4-thiazolyl)-2-[[R,S)-diphenylmethyloxycarbonyl)(3-thienyl)methoxy]imino]acetamido]-3-[[(4-carboxy-3-hydroxy-5-isothiazolyl)thio]methyl]-3-cephem-4-carboxylate (500 mg) was dissolved in dichloromethane (5 ml) and anisole (2 ml), trifluoroacetic acid (8 ml) was added to the resulting mixture under ice-cooling, and then the mixture was stirred for 1 hr. and 45 min. The trifluoroacetic acid was evaporated under the reduced pressure to obtain residue. Thus obtained residue was triturated with ethyl ether, and then filtered off to give powder. The powder was added to trifluoroacetic acid (16 ml) under ice-cooling. To this water (4 ml) was added dropwise, stirred for 30 min., and then stirred for 90 min. at the room temperature. Trifluoroacetic acid and the solvent were evaporated under the reduced pressure. To the residue thus obtained ethyl ether was added to triturate. The residue was filtered off to obtain powder (129 mg). To this powder water (100 ml) and sodium hydrogen carbonate were added to dissolve, the solution was absorbed on Diaion HP-20, and then dissolved into water-methanol. The fraction containing the disired compound was collected to concentrate, and then lyophilized to give trisodium 7β-[(Z)-2-(2-amino-4-thiazolyl)-2-[[(R S)-(carboxylate)(3-thienyl)methoxy]imino]acetamido]-3-[[(4-carboxylate-3-hydroxy-5-isothiazolyl)thio]methyl]-3-cephem-4-carboxylate (142 mg).

IR spectrum $\nu_{max}^{KBr}$(cm$^{-1}$); 3456, 1770, 1682, 1618, 1506, 1388, 1362, 1206, 700.

NMR spectrum (D$_2$O) δ(ppm); 3.45(2H, dd, —CH$_2$S—), 3.78-4.36(2H, m,

5.07(1H, d, CH at 6-position), 5.63(1H, s, —CH—), 5.67, 5.71(1H, each of d, CH at 7-position), 7.03(1H, s,

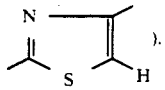

7.19(1H, d,

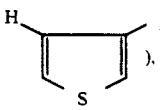

7.41(1H, dd,

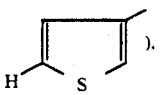

7.52(1H, d,

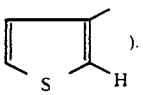

EXAMPLE 17

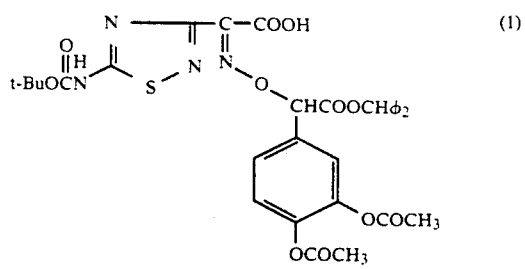

2-(5-Tert-butyloxycarbonylamino-1,2,4-thiadiazol-3-yl)-2-oxoacetic acid (1.49 g) was dissolved in methanol (60 ml), and to this solution a solution of diphenylmethyl (3,4-diacetoxyphenyl)-2-aminooxyacetate (2.45 g) in methanol (25 ml) was added dropwise. The mixture was stirred for 3 hrs. at the room temperature, and the solvent was evaporated to obtain (Z)-2-(5-tert-butyloxycarbonylamino-1,2,4-thiadiazol-3-yl)-2-[[(diphenylmethyloxycarbonyl)(3,4-diacetoxyphenyl)methoxy]imino]acetic acid (3.84 g).

NMR spectrum (DMSO-d$_6$) δ(ppm); 1.50(9H, s, t-Bu), 2.30(6H, s, CH$_3$COX2), 6.18(1H, s, OCHCOO), 6.87(1H, s, COOCH$\phi_2$), 7.1-7.5(13H, m, Ar—H).

Mass spectrum FAB(Pos.); 705(M+1)$^+$.

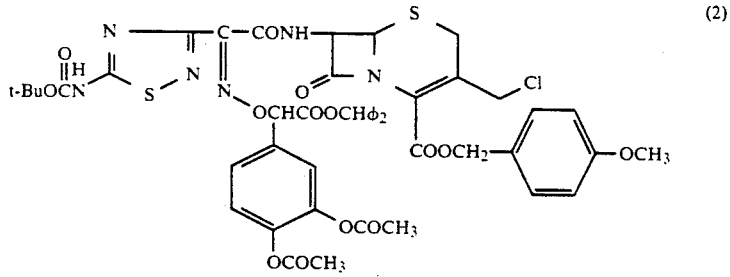

p-Methoxybenzyl 7β-amino-3-chloromethyl-3-cephem-4-carboxylic acid hydrochloride (2.19 g) was suspended in methylene chloride (22 ml). To this mixture N,O-bis (trimethylsilyl)acetamide (1.33 ml) was added at about 10° C. After the solution became clear, the solution was cooled to −60° C. below. To this solution a solution obtained by dissolving pyridine (2.62 ml) and (Z)-2-(5-tert-butyloxycarbonylamino-1,2,4-thiadiazol-3-yl)-2-[[(diphenylmethyloxycarbonyl)(3,4-diacetoxypheny)methoxy]imino]acetic acid (3.80 g) obtained from the above (1) in methylene chloride (38 ml), adding phosphorus pentachloride (1.12 g) with ice-cooling to −20° C. below and stirring for 1 hr. at −20° C. was added. This reaction solution was stirred for 2 hrs. at −20° C., and then poured into the mixture of a saturated solution of potassium dihydrogen phosphate and ice. The organic layer was separated, and the aqueous layer was extracted with methylene chloride for two times. The combined organic layer was washed with a saturated saline, and dried over anhydrous magnesium sulfate. The solvent was evaporated under the reduced pressure, the residue was applied to silica gel column chromatography, and 40-20% n-hexane-chloroform eluate was concentrated to give p-methoxybenzyl 7β-[(Z)-2-(5-tert-butyloxycarbonyl-1,2,4-thiadiazol-3-yl)-2-[[(R S)-(diphenylmethyloxycarbonyl)(3,4-diacetoxyphenyl)methoxy]imino]acetamido]-3-chloromethyl-3-cephem-4-carboxylate (3.15 g).

NMR spectrum (DMSO-d₆): δ(ppm): 1.50(9H, s, t-Bu), 2.28(6H, s, C$\underline{H}_3$COX2), 3.3–3.7(2H, m, —SCH₂— at 2-position), 3.74, 3.76(3H, each of s, —OCH₃), 4.48(2H, m, —CH₂Cl), 5.18(1H, m, —CH— at 6-position), 5.20(2H, br, s, COOC$\underline{H}_2$—), 5.90(1H, m, —CH— at 7-position), 6.16(1H, s, O$\underline{CH}$COO), 6.8–7.0(3H, m, COOC$\underline{H}$φ₂,

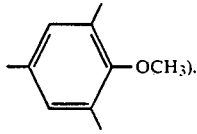

7.1–7.5(15H, m, Ar—H), 9.80, 9.86(1H, each of d, —CON$\underline{H}$—) Mass spectrum FAB(Neg.)m/z: 1053(M-1).

thoxy]imino]acetamido]-3-[[4-carboxy-3-hydroxy-5-isothiazolyl)thio]methyl]-3-cephem-4-carboxylate (0.88 g).

NMR spectrum (DMSO-d₆): δ(ppm); 1.50(9H, s, t-Bu), 2.26, 2.28(each of 3H, s, CH₃COX2), 3.3–3.7(2H, m, —SCH₂— at 2-position), 3.72, 3.73(3H, each of s,—OCH₃), 4.15(2H, br dd, —CH₂S—), 5.1–5.3(3H, m, —CH— at 6-position, COOC$\underline{H}_2$—), 5.88(1H, m, —CH— at 7-position), 6.06(1H, s, O$\underline{CH}$COO), 6.86(1H, br s, COOC$\underline{H}$φ₂), 6.87(2H, dd,

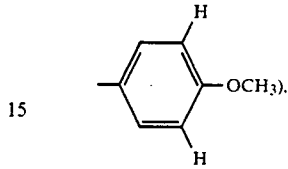

7.1–7.5(15H, m, Ar—H), 9.78, 9.86(1H, each of d, —CON$\underline{H}$—).

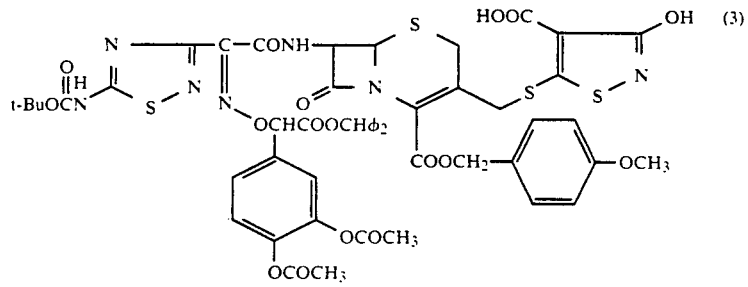

Tripotassium 5-mercapto-4-carboxy-3-hydroxyisothiazole (0.32 g) was dissolved in water (7 ml). To this solution methylene chloride (7 ml) and tetra-n-butylammonium hydrogen sulfate (0.77 g) were added. To the resultant solution p-methoxybenzyl 7-β[[(Z)-2-(5-tert-butyloxycarbonyl-1,2,4-thiadiazol-3-yl)-2[[(R S)-(diphenylmethyloxycarbonyl)(3,4-diacetoxyphenyl)methoxy]imino]acetamido]-3-chloromethyl-3-cephem-4-carboxylate (1.0 g) obtained from Example 2 was added, and stirred at the room temperature over night. The reaction solution was extracted with methylene chloride. The organic layer was washed with water and a saturated saline, and dried over magnesium sulfate anhydride. The solvent was evaporated under the reduced pressure. The residue was subjected to silica gel column chromatography, and the 2-5% methanol-chloroform eluate was concentrated to obtain tetra-n-butylammonium p-methoxybenzyl 7β-[[(Z)-2-(5-tert-butyloxycarbonyl-1,2,4-thiadiazol-3-yl)-2-[[(R S)-(diphenylmethyloxycarbonyl)(3,4-diacetoxydiphenyl)me- Mass spectrum FAB(Neg.)m/z: 1195(M-1)⁻.

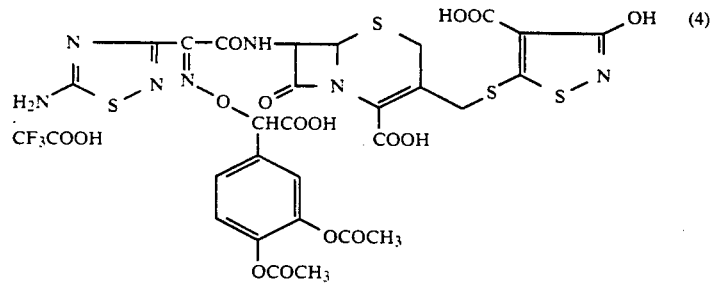

Tetra-n-butylammonium p-methoxybenzyl 7β-[(Z)-2-(5-tertbutyloxycarbonyl-1,2,4-thiadiazol-3-yl)-2-[[(R S)-(diphenylmethyloxycarbonyl)(3,4-diacetoxyphenyl)-methoxy]imino]acetamido]-3-[[(4-carboxy-3-hydroxy-5-isothiazolyl)thio]methy]-3-cephem-4-carboxylate (0.85 g) obtained from the above (3) was dissolved in methylene chloride (1.7 ml) and anisole (0.5 ml). To this mixture trifluoroacetic acid (8.5 ml) was added under ice-cooling, and reacted for 2 hrs. at the room temperature. The solvent was evaporated under the reduced pressure. The residue was triturated with ether to give 7β-[(Z)-2-(5-amino-1,2,4-thiadiazol-3-yl)-2-[[(R S)-(carboxy)(3,4-diacetoxyphenyl)methoxy]imino]acetamido]-3-[[(4-carboxy-3-hydroxy-5-isothiazolyl)thio]methyl]-3-cephem-4-carboxylic acid trifluoroacetate (0.60 g).

NMR spectrum (d⁶-DMSO): δ(ppm); 2.16(6H, s, CH₃COX2), 3.3–3.8(2H, m, —SCH₂— at 2-position), 4.06, 4.24(each of 1H, m, —CH₂S—), 5.11, 5.15(1H, each of d, —CH— at 6-position), 5.67(1H, s, —C$\underline{H}$COO), 5.82(1H, m, —CH— at 7-position), 6.4–6.6(3$\underline{H}$, m, Ar—H), 9.55, 9.67(1H, each of d, —CON$\underline{H}$—).

Mass spectrum FAB(Neg.)m/z: 808(M-1)⁻.
IR spectrum $\nu_{max}^{KBr}$ (cm⁻¹): 1774.

EXAMPLE 18

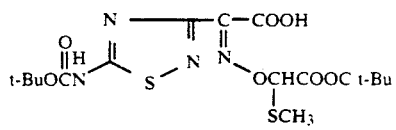 (1)

2-(5-Tert-butyloxycarbonylamino-1,2,4-thiadiazol-3-yl)-2-oxoacetic acid (3.0 g) was dissolved in methanol (30 ml). To this solution a solution of tert-butyl 2-aminooxy-2-(methylthio)acetate (2.12 g) in methanol (20 ml) was added dropwise. The resultant mixture was stirred for 1 hr. at the room temperature, and then the solvent was evaporated to give (Z)-2-(5-tert-butyloxycarbonylamino-1,2,4-thiadiazol-3-yl)-2-[[(tert-butoxycarbonyl)(methylthio)methoxy]imino]acetic acid (2.42 g).

NMR spectrum (DMSO-d₆); δ(ppm); 1.44(9H, s, t-Bu), 1.51(9H, s, t-Bu), 2.15(3H, s, SCH₃), 5.80(1H, s, OCHCOO), 12.60(1H, br s, —NHCO).

Mass spectrum FAB(Pos.)m/z: 449(M+1)⁺.

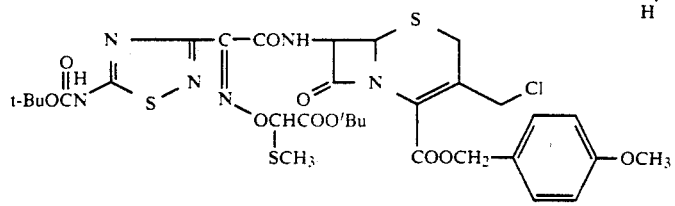

p-Methoxybenzyl 7β-amino-3-chloromethyl-3-cephem-4-carboxylic acid hydrochloride (2.12 g) was suspended in methylene chloride (21 ml), and N,O-bis(trimethylsilyl)acetamide (1.30 ml) was added at about 10° C. After the solution became clear, the solution was cooled to −60° C. below. To this solution was added a solution obtained by dissolving pyridine (2.62 ml) and (Z)-2-(5-tert-butyloxycarbonylamino-1,2,4-thiadiazol-3-yl)-2-[[(tertbutoxycarbonyl)(methylthio)methoxy]imino]acetic acid (2.35 g) obtained from Example 5 into methylene chloride (23 ml), adding phosphorous pentachloride (1.09 g) with ice-cooling to −20° C. below and stirring for 1 hr. at −20° C., and then poured into a mixture of a saturated solution of potassium dihydrogen phosphate and ice. The organic layer was separated, and the aqueous layer was extracted with methylene chloride. The combined organic layer was washed with a saturated saline, and dried over magnesium sulfate anhydrate. The solvent was evaporated under the reduced pressure, the residue was subjected to silica gel column chromatography, and chloroform eluate was concentrated to obtain p-methoxybenzyl 7β-[(Z)-2-(5-tert-butyloxycarbonyl-1,2,4-thiadiazol-3-yl)-2-[[(R S)-(tert-butoxycarbonyl)(methyloxy)methoxy]imino]acetamido]-3-chloromethyl-3-cephem-4-carboxylate (3.20 g).

NMR spectrum (DMSO-d₆): δ(ppm); 1.44(9H, s, t-Bu), 1.52(9H, s, t-Bu), 2.20(3H, s, —SCH₃), 3.52, 3.73(2H, each of br d, —SCH₂— at 2-position), 3.75(3H, s, —OCH₃), 4.46, 4.54(2H, each of br d, —CH₂S—), 5.1–5.3(3H, m, —CH— at 6-position, COOCH₂—), 5.72(1H, s, OCHCOO), 5.93(1H, m, —CH— at 7-position), 6.92(2H, d,

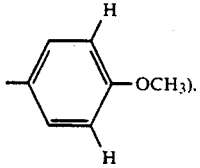

7.35(2H, d,

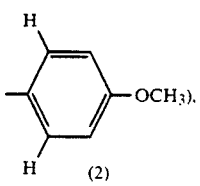

9.75(1H, d, —CONH—).
Mass spectrum FAB(Neg.)m/z: 797(M-1)⁻.

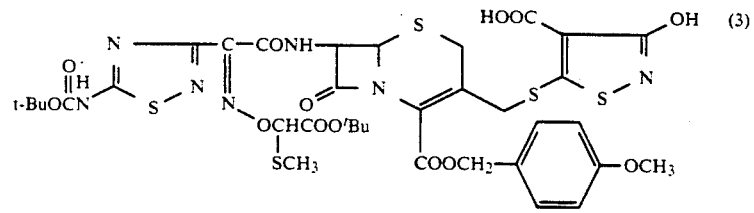 (3)

Tripotassium 5-mercapto-4-carboxy-3-hydroxyisothiazole (1.36 g) was dissolved in water (30 ml), and methylene chloride (30 ml) and tetra-n-butylammonium hydrogen sulfate (3.16 g) were added thereto. To this solution a solution of p-methoxybenzyl 7β-[(Z)-2-(5-tert-butyloxycarbonyl-1,2,4-thiadiazol-3-yl)-2-[[(R S)-(tert-butoxycarbonyl)(methylthio)methoxy]imino]acetamido]-3-chloromethyl-3-cephem-4-carboxylate (3.1 g) obtained from Example 6 in methylene chloride (20 ml) was added, and the mixture was stirred at the room temperature over night. The reaction solution was extracted with methylene chloride, the organic layer was washed with water, 10% citric acid solution (×2) and a saturated saline (×1) and dried over anhydrous magnesium sulfate, and the solvent was evaporated under the reduced pressure. The residue was subjected to silica gel column chromatography, and 5% acetone-chloroform-3% methanol-chloroform eluate was concentrated to obtain p-methoxybenzyl 7β-[(Z)-2-(5-tert-butyloxycarbonyl-1,2,4-thiadiazol-3-yl)-2-[[(R S)-(tert-butoxycarbonyl)(methylthio)methoxy]imino]acetamido]-3-[(4-carboxy-3-hydroxy-5-isothiazolyl)thiomethyl]-3-cephem-4-carboxylate (1.40 g).

NMR spectrum (DMSO-d₆): (ppm); 1.43(9H, s, t-Bu), 1.56(9H, s, t-Bu), 2.19(3H, s, —SCH₃), 3.55, 3.77(2H, each of br d, —SCH₂— at 2-position), 3.76(3H, s, —OCH₃), 4.04, 4.15(2H, each of br d, —CH₂S—), 5.20(1H, m, —CH— at 6-position), 5.22(2H, br s, COOCH₂—), 5.71(1H, s, OCHCOO), 5.91(1H, m, —CH— at 7-position), 6.88(2H, d,

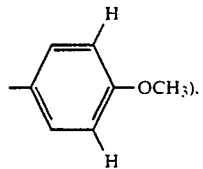

7.32(2H,

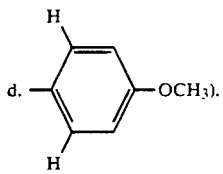

9.73(1H, d, —CONH—).
Mass spectrum FAB(pos.)m/z: 940(M+1)⁺.

thiazolyl)thiomethyl]-3-cephem-4-carboxylic acid trifluoroacetate (0.85 g).

NMR spectrum (DMSO-d₆): δ(ppm); 2.18(3H, s, —SCH₃), 3.53, 3.75(2H, each of br d, —SCH₂ at 2-position), 4.08, 4.27(2H, each of br d, —CH₂S—), 5.20(1H, m, —CH— at 6-position), 5.68(1H, s, OCHCOO), 5.85(1H, m, —CH— at 7-position), 9.63, 9.66(1H, each of d, —CONH—).

Mass spectrum FAB(Pos.)m/z: 664(M+1)⁺.
IR spectrum; $\nu_{max}^{KBr}$ (cm⁻¹): 1780.

EXAMPLE 19

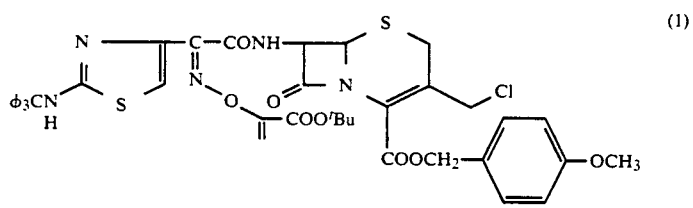

p-Methoxybenzyl 7β-amino-3-chloromethyl-3-cephem-4-carboxylic acid hydrochloride (2.06 g) was suspended in methylene chloride (20 ml), and N,O-bis(trimethylsilyl)acetamide (1.26 ml) was added at about 10° C. After the solution became clear, the solution was cooled to −60° C. below, and to this solution a solution obtained by dissolving pyridine (2.47 ml) and (Z)-2-(1-tert-butoxycarbonylvinyloxyimino)-2-(2-tritylamino-4-thiazolyl)acetic acid (2.95 g) in methylene chloride (30 ml), adding phosphorus pentachloride (1.09 g) under cooling to −20° C. below and stirring for 1 hr. at −20° C. was added. The reaction solution was stirred for 1 hr. at −20° C., and then poured into the mixture of a saturated potassium dihydrogen phosphate solution and ice. The organic layer was separated, and the aqueous layer was extracted with methylene chloride (2×). The combined organic layer was washed with a saturated saline, and dried over anhydrous magnesium sulfate. The solvent was evaporated under the reduced pressure, the residue was subjected to silica gel column chromatography, and 0.5% acetone-chloroform eluate was concentrated to give p-methoxybenzyl 7β-[(Z)-2-(2-

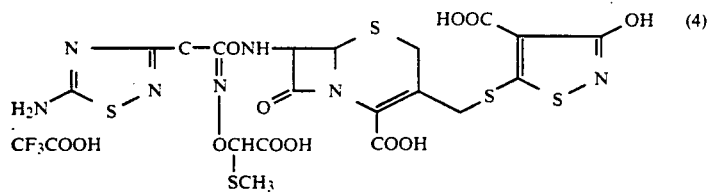

p-Methoxybenzyl 7β-[[(Z)-2-(5-tert-butyloxycarbonyl-1,2,4-thiadiazol-3-yl)-2-[[(R S)-tert-butoxycarbonyl)(methylthio)methoxy]imino]acetamido]-3-[(4-carboxy-3-hydroxy-5-isothiazolyl)thiomethyl]-3-cephem-4-carboxylate (1.30 g) obtained from the above (3) was dissolved in methylene chloride (3 ml) and anisole (0.6 ml). To this solution trifluoroacetic acid (13 ml) was added under ice-cool stirring, and reacted for 1 hr. at the room temperature. The solvent was evaporated under the reduced pressure, and the residue was triturated to obtain 7β-[(Z)-2-(5-amino-1,2,4-thiadiazol-3-yl)-2-[[(R S)-(carboxy)(methylthio)methoxy]imino]acetamido]-3-[(4-carboxy-3-hydroxy-5-isothiazolyl)thiomethyl]-3-cephem-4-carboxylic acid trifluoroacetate (0.85 g).

tritylamino-4-thiazolyl)-2-(1-tert-butoxycarbonylvinyloxyimino)acetamido]-3-chloromethyl-3-cephem-4-carboxylate (3.55 g).

NMR spectrum (DMSO-d₆): δ(ppm); 1.45(9H, s, t-Bu), 3.48, 3.69(2H, each of d, —SCH₂— at 2-position), 3.74(3H, s, —OCH₃), 4.44, 4.53 (2H, each of d, —CH₂Cl), 5.1–5.3(4H, m, —CH— at 6-position, vinyl-H, COOCH₂—), 5.32(1H, s, vinyl-H), 5.70(1H, dd, —CH— at 7-position), 6.90(2H, d, 6.91(1H, s,

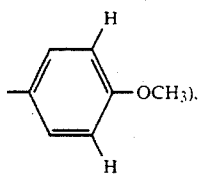

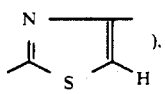

7.1–7.3 (17H, m, Ar —H,

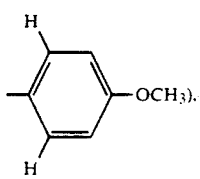

8.92(1H, s, —NH$\phi_3$), 9.79(1H, d, —CONH—)
Mass spectrum FAB(Pog.)m/z: 906($\overline{M+1}$)

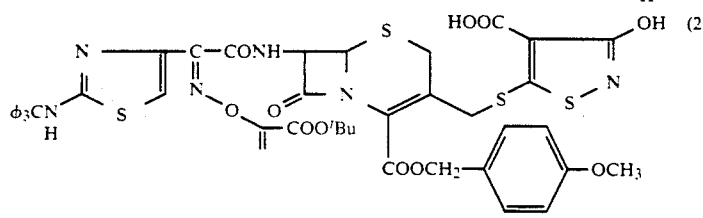

Tripotassium 5-mercapto-4-carboxy-3-hydroxyisothiazole (1.32 g) was dissolved in water (30 ml), and methylene chloride (30 ml) and tetra-n-butylammonium hydrogen sulfate (3.07 g) were added. To this solution, a solution of p-methoxybenzyl 7β-[(Z)-2-(2-tritylamino-4-thiazolyl)-2-(1-tert-butoxy carbonylvinyloxyimino)acetamido]-3-chloromethyl-3-cephem-4-carboxylate (3.50 g) obtained from the above (1) in methylene chloride (20 ml) was added, and stirred at the room temperature over night. The reaction solution was extracted with methylene chloride, and the organic layer was washed with water, 10% citric acid solution (×2) and a saturated saline (1×) and dried over anhydrous magnesium sulfate. The solvent was evaporated under the reduced pressure. The residue was subjected to silica gel column chromatography, and chloroform-10% acetone-chloroform eluate was concentrated to obtain p-methoxybenzyl 7β-[(Z)-2-(2-tritylamino-4-thiazolyl)-2-(1-tert-butoxycarbonylvinyloxyimino)acetamido]-3-[(4-carboxy-3-hydroxy-5-isothiazolyl)thiomethyl]-3-cephem-4-carboxylate (2.10 g).

NMR spectrum (DMSO-d$_6$): δ(ppm); 1.44(9H, s, t-Bu), 3.51, 3.74(2H, each of d, —SCH$_2$— at 2-position), 3.72(3H, s, —OCH$_3$), 4.04, 4.15 (2H, each of d, —CH$_2$Cl), 5.1–5.2(4H, m, —CH— at 6-position, vinyl-H, COO$\underline{CH_2}$—), 5.32(1H, s, vinyl-H), 5.69(1H, dd, —CH— at 7-position), 6.84(2H, d,

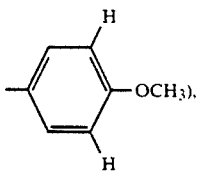

6.93(1H, s,

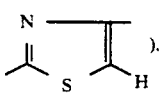

7.1–7.3(7H, m, Ar—H,

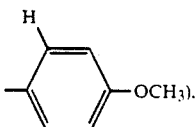

8.91(1H, s, —NHφ$_3$), 9.77(1H, d, —CONH—).
Mass spectrum FAB(Pog.)m/z: 1047($\overline{M+1}$).

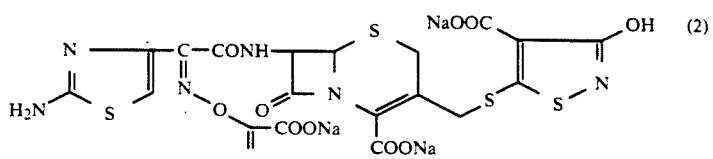

p-Methoxybenzyl 7β-[(Z)-2-(2-tritylamino-4-thiazolyl)-2-(1-tert-butoxycarbonylvinyloxyimino)acetamido]-3-[(4-carboxy-3-hydroxy-5-isothiazolyl)thiomethyl]-3-cephem-4-carboxylate (1.0 g) obtained from the above (2) was dissolved in methylene chloride (3 ml) and anisole (1 ml), trifluoroacetic acid (10 ml) was added under ice-cool stirring, and the mixture was reacted for 1 hr. at the room temperature. The solvent was evaporated under the reduced pressure, and the residue was triturated with ether. Thus obtained powder was dissolved in an aqueous solution of sodium hydrogen carbonate, adsorbed on Diaion HP-20, and then eluted with water and methanol. The fraction containing the desired compound was collected, concentrated and lyophilized to obtain trisodium 7β-[(Z)-2-(2-amino-4-thiazolyl)-2-(1carboxylatevinyloxyimino)acetamido]-3-[(4-carboxylate-3-hydroxy-5-isothiazolyl)thiomethyl]-3-cephem-4-carboxylate (0.39 g).

NMR spectrum (DMSO-d₆): δ(ppm); 3.50, 3.68(2H, each of d, —SCH₂— at 2-position), 3.95, 4.38(2H, each of d, —CH₂S—), 4.88, 5.17(2H, each of s, vinyl-H), 5.03(1H, d, —CH— at 6-position), 5.62(1H, br -d, —CH— at 7-position), 6.90(1H, s,

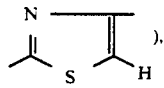), 10.50(1H, br-s, —CONH—).
Mass spectrum FAB(Pog.)m/z: 629(M+1)⁺.
IR spectrum; $\nu_{max}^{KBr}$ (cm⁻¹): 1770.

EXAMPLE 20

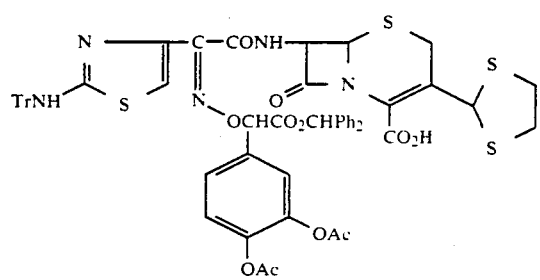

(Z)-2-(2-tritylamino-4-thiazolyl)-2-[[(diphenylmethoxycarbonyl)(3,4-diacetoxyphenyl)methoxy]imino]acetic acid (1.70 g, 2.01 mmol) was dissolved in methylene chloride (15 ml) under argon atmosphere, and phosphorus pentachloride (0.42 g, 2.02 mmol) was added at −25° C. The mixture was stirred for 2 hrs. at −20° to −15° C. to obtain methylene chloride solution of acid chloride. Meanwhile, 7-amino-3-(1,3-dithiolan-2-yl)-3-cephem-4-carboxylic acid trifluoroacetate (0.84 g, 2.01 mmol) was dissolved in methylene chloride (15 ml) under argon atmosphere, and N,O-bis(trimethylsilyl)acetamide (1.0 ml, 4.09 mmol) was added at 10° C. below. Until the solution became homogenous, the solution was stirred and cooled to −65° C., and then pyridine (0.90 ml, 11.13 mmol) was added at the same temperature. To this solution, acid chloride solution obtained from the above was added. The solution was stirred for 2 hrs. at −40° to −35° C., and a saturated solution of potassium dihydrogen phosphate (100 ml) was added and stirred. The organic layer was washed with water and a saturated saline, and dried over magnesium sulfate. The solvent was evaporated to give a caramel (2.17 g). This was subjected to silica gel column chromatography eluting with chloroform-methanol-formic acid (volume ratio 90:10:2) to obtain 7β-[(Z)-2-(2-tritylamino-4-thiazolyl)-2-[[(R S)-(diphenylmethoxycarbonyl)(3,4-diacethoxyphenyl)methoxy]imino]acetamido]-3-(1,3-dithiolan-2-yl)-3-cephem-4-carboxylic acid (1.371 g).

IR spectrum $\nu_{max}^{KBr}$ (cm⁻¹): 1774.

NMR spectrum (DMSO-d₆): (ppm); 2.29(6H, s, —OAc). 3.34–3.72(6H, m, —CH₂— at 2-position, —S(CH₂)₂S—), 5.09–5.17(1H, dX2, —CH— at 6-position), 5.58–5.72(1H, ddX2, CH at 7-position), 5.87(1H, s,

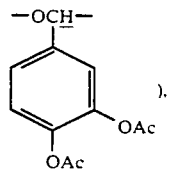), 6.00, 6.02(1H, each of s,

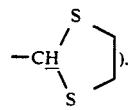), 6.76, 6.79(1H, each of s,

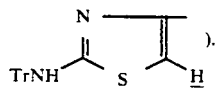), 6.83, 6.86 (1H, each of s, —CHPh₂), 7.17–7.42(28H, m, —CHPh₂Tr—,

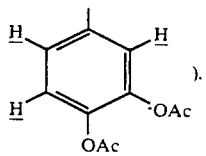), 8.88, 8.93(1H, each of s, TrNH—), 9.55–9.73(1H, dX2, —CONH—).
Mass spectrum FAB(Pos.): 1132(M+H)⁺.

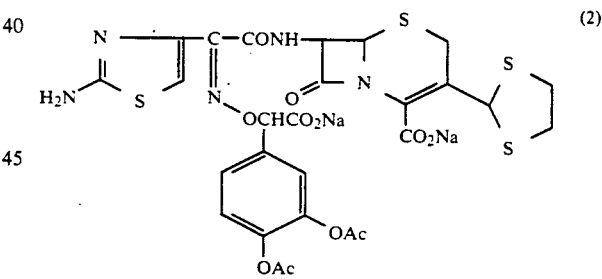

7β-[(Z)-2-(2-tritylamino-4-thiazolyl)-2-[[(R   S)-(diphenylmethoxycarbonyl)(3,4-diacetoxyphenyl)methoxy]imino]acetamido]-3-(1,3-dithiolan-2-yl)-3-cephem-4-carboxylic acid (1.33 g, 1.17 mmol) obtained from the above (1) was dissolved in methylene chloride (25 ml). To this solution, anisole (5 ml) was added, trifluoroacetic acid (50 ml) was added under ice-cooling, and then the mixture was stirred for 90 min. at the room temperature. The volatile component was evaporated under the reduced pressure to give a residue, diethyl ether and n-hexane were added thereto to triturate, and then the mixture was filtered off. The filtration was dissolved in ice-cooled trifluoroacetic acid (50 ml), and to this solution water (25 ml) was added dropwise at 15° C. below and stirred for 90 min. at the room temperature. The solvent was evaporated to give a residue, and to this diethyl ether and n-hexane were added to triturate to obtain a crude product (736 mg). The crude product (186 ml) was suspended in water, sodium hydrogen carbonate was added until the solution become homogeneous, and the product was absorbed on Diaion HP-20 and then eluted with water and methanol. The fraction containing the desired compound was concentrated, and lyophilized to obtain disodium 7β-[(Z)-2-(2-amino-4-thiazolyl)-2-[[(R S)-(carboxylate)(3,4-diacetoxyphenyl)methoxy]imino]acetamido]-3-(1,3-dithiolan-2-yl)-3-cephem-4-carboxylate (74 mg).

IR spectrum $v_{max}^{KBr}$ (cm$^{-1}$): 1772.

NMR spectrum (D$_2$O): δ(ppm); 2.37(6H, s, —OAC), 3.36–3.57(6H, m, —CH$_2$— at 2-position, —S(CH$_2$)$_2$S—), 5.05–5.10(1H, m, CH at 6-position), 5.57(1H, s,

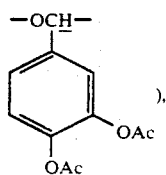

5.66–5.69(1H, m, CH at 7-position), 5.86, 5.89(1H, each of s,

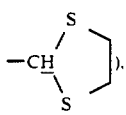

6.94–7.05(4H, m,

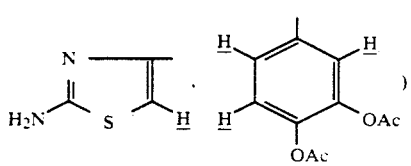

Mass spectrum FAB(Pos.): 724(M+H)+.

EXAMPLE 21

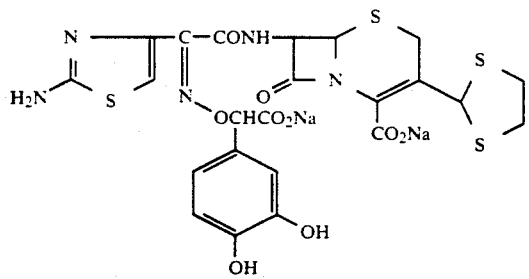

Crud product of 7β-[(Z)-2-(2-amino-4-thiazolyl)-2-[[(R S)-(carboxy)(3,4-diacetoxyphenyl)methoxy]imino]acetamido]-3-(1,3-dithiolan-2-yl)-3-cephem-4-carboxylic acid (550 mg) was dissolved in a saturated solution (30 ml) of sodium hydrogen carbonate. The solution was stirred for 45 min., adsorbed on Diaion HP-20, and eluted with water and methanol. The fraction containing the desired compound was concentrated, and lyophilized to obtain disodium 7β-[(Z)-2-(2-amino-4-thiazolyl)-2-[[(R S)-carboxylate)(3,4-hydroxyphenyl)methoxy]imino]acetamido]-3-(1,3-dithiolan-2-yl)-3-cephem-4-carboxylate (190 mg).

IR spectrum $v_{max}^{KBr}$ (cm$^{-1}$): 1772.

NMR spectrum (D$_2$O): (ppm); 3.30–3.67(6H, m, —CH$_2$— at 2-position, —S(CH$_2$)$_2$S—), 4.99–5.10(1H, m, CH at 6-position), 5.41, 5.43(1H, each of s,

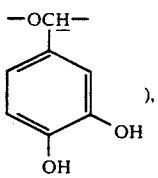

5.65–5.67(1H, m, CH at 7-position), 5.83, 5.86(1H, each of s,

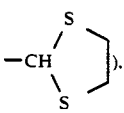

6.87–7.04(4H, m,

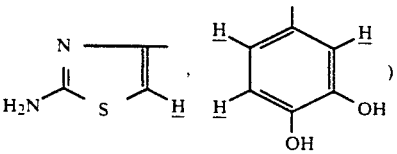

Mass spectrum FAB(Pos.): 684(M+H)+.

EXAMPLE 22

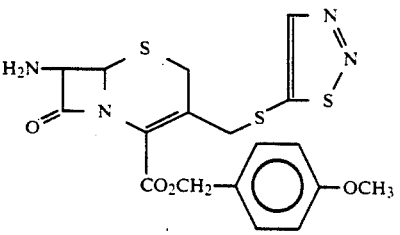

Sodium 5-mercapto-1,2,3-thiadiazole (2.45 g) was suspended in methanol (20 ml), and a solution of p-methoxybenzyl 7-amino-3-chloromethyl-3-cephem-4-carboxylate (5.60 g) in methylene chloride (20 ml) was added dropwise. The mixture was stirred for 30 min. under ice-cooling, an insoluble material was filtered off, and the solvent was evaporated to obtain a crude material (6.38 g). The crude material was subjected to silica gel chromatography eluting with chloroform-ethyl acetate to obtain p-methoxybenzyl 7-amino-3-(1,2,3-thiadiazol-5-yl)thiomethyl-3-cephem-4-carboxylate (4.90 g).

IR spectrum $v_{max}^{KBr}$ (cm$^{-1}$): 1776.

Mass spectrum FAB(Pos.): 451.

NMR spectrum (DMSO-d$_6$): δ(ppm); 3.52, 3.71(2H, AB pattern, CH$_2$ at 2-position), 3.73(3H, s, OCH$_3$), 4.13, 4.19(2H, AB pattern,

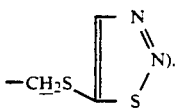

4.79(1H, d, C<u>H</u> at 6-position), 5.00(1H, d, C<u>H</u> at 7-position), 5.08(2<u>H</u>, s,

6.88, 7.29(4H, AB pattern,

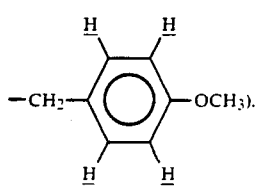

8.83(1H, s,

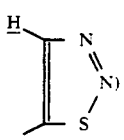

to obtain p-methoxybenzyl 7β-[(Z)-2-(2-tritylamino-4-thiazolyl)-2-[[(R S)-(tert-butoxycarbonyl)(3,4-diacetoxyphenylthio) methoxy]imino]acetamido]-3-(1,2,3-thiadiazol-5-yl)thiomethyl-3-cephem-4-carboxylate (1.92 g).

IR spectrum $\nu_{max}^{KBr}$ (cm$^{-1}$): 1780.
Mass spectrum FAB (Pos.): 1200.
NMR spectrum (DMSO-d$_6$): (ppm); 1.26(9H, s, t-Bu), 3.4–3.8(2H, m, CH$_2$ at 2-position), 3.72(3H, s, OCH$_3$), 4.1–4.3(2H, m,

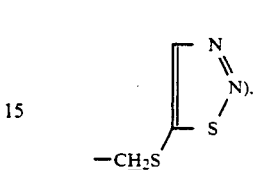

5.09(2H, s,

5.18, 5.20(1H, each of d, C<u>H</u> at 6-position), 5.68(1H, q, C<u>H</u> at 7-position), 5.82, 5.84(1H, each of s,

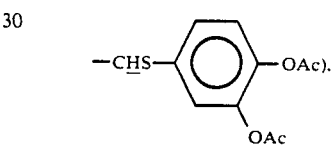

(2)

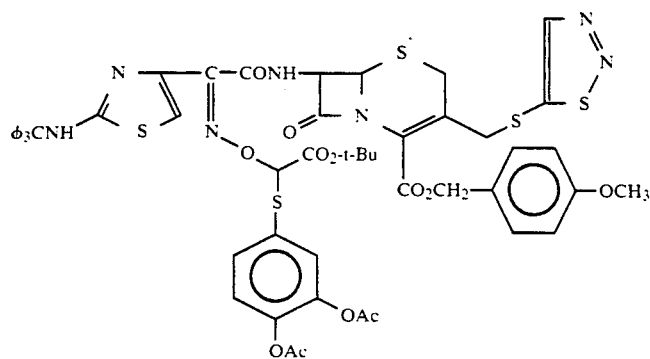

(Z)-2-(2-tritylamino-4-thiazolyl)-2-[[(tert-butoxycarbonyl)(3,4-diacetoxyphenylthio)methoxy]imino]acetic acid (2.00 g) was dissolved in methylene chloride (30 ml), and phosphorus pentachloride (540 mg) was added at −20° C. The mixture was stirred for 1 hr. at −20° C. to obtain a methylene chloride solution of acid chloride. Meanwhile, p-methoxybenzyl 7-amino-3-(1,2,3-thiadiazol-5-yl)thiomethyl-3-cephem-4-carboxylate (1.17 g) obtained from the above (1) was dissolved in methylene chloride (30 ml), and pyridine (1.06 ml) was added at −70° C. To the solution thus obtained the said methylene chloride solution of acid chloride was added at −70° C. The mixture was stirred for 10 min. and warmed to −20° C., and excessive amounts of ethyl acetate were added. The organic layer was washed with a saturated saline and dried over anhydrous sodium sulfate, and the solvent was removed to obtain a caramel (3.08 g). The caramel was subjected to silica gel chromatography eluting with chloroform-ethyl acetate 6.80(1H, s,

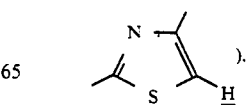

6.87, 7.22(4H, AB pattern, 7.1-7.6(18H, m,

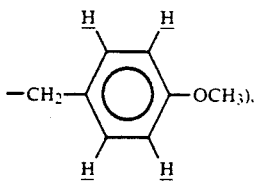

Tr), 8.81, 8.83(1H, each of s,

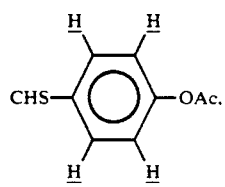

8.88, 8.89(1H, each of s, NHTr), 9.75(1H, d, CONH)

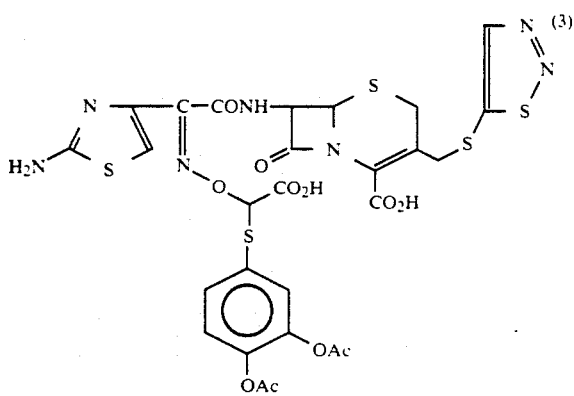

p-Methoxybenzyl 7β-[(Z)-2-(2-tritylamino-4-thiazolyl)-2-[[(R S)-(tert-butoxycarbonyl)(3,4-diacetoxyphenylthio)methoxy]imino]acetamido]-3-(1,2,3-thiadiazol-5-yl)thiomethyl-3-cephem-4-carboxylate (1.92 g) obtain from the above (2) was dissolved in methylene chloride (10 ml) and anisole (1 ml), trifluoroacetic acid (10 ml) was added dropwise under ince-cooling, and the mixture was stirred for 1 hr. at the room temperature. The residue obtained by evaporating the trifluoroacetic acid and methylene chloride under the reduced pressure was suspended in water (10 ml), and the trifluoroacetic acid (20 ml) was added under ice-cooling. After stirring for 1 hr. at the room temperature, trifluoroacetic acid and water were evaporated under the reduced pressure to obtain a residue. To the residue ethyl ether was added to triturate, and the residue was filtered off to give a powder (1.18 g). The powder (250 mg) was suspended in water, absorbed on Diaion HP-20, and eluted with water-methanol. The fraction containing the desired compound was collected, concentrated and lyophilized to obtain 7β-[(Z)-2-(2-amino-4-thiazolyl)-2-[[(R S)-(carboxy) (3,4-diacetoxyphenylthi-o)methoxy]imino]acetamido]-3-(1,2,3-thiadiazol-5-yl)thiomethyl-3-cephem-4-carboxylic acid (540 mg).

IR spectrum $\nu_{max}^{KBr}$(cm$^{-1}$): 1776.

Mass spectrum FAB (Pos.): 782.

NMR spectrum (DMSO-d$_6$): δ(ppm); 2.26(6H, s, OAc), 3.4–3.8(2H, m, CH$_2$ at 2-position), 4.1–4.4 (2H, m, —CH$_2$S—), 5.19, 5.21(1H, each of d, CH at 6-position), 5.7–5.9(1H, m, CH at 7-position), 5.90, 5.92 (1H, each of s,

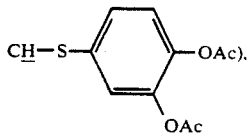

6.81, 6.82 (1H, each of s,

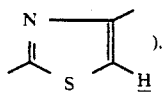

7.1–7.5 (3H, m,

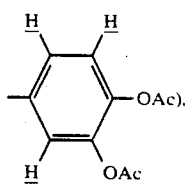

9.88, 9.87(1H, each of s,

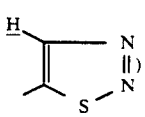

EXAMPLE 23

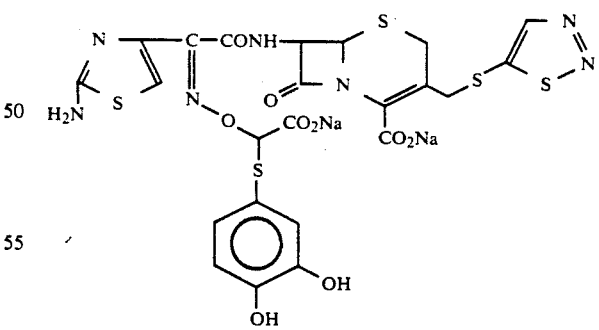

950 mg of 7β-[(Z)-2-(2-amino-4-thiazolyl)-2-[[(R S)-(tert-butoxycarbonyl)(3,4-diacetoxyphenylthio)methoxy]imino]acetamido]-3-(1,2,3-thiadiazol-5-yl)thiomethyl-3-cephem-4-carboxylate obtained from Example 22 was suspended in 30 ml of water, and saturated sodium hydrogen carbonate aqueous solution was added therein at the room temperature in order to make pH 8. After stirring for 2.5 hrs. at the room temperature, the aqueous solution was adsorbed on Diaion HP-20 and was eluted with water-methanol. The fraction containing the desired product was collected, concentrated and then, lyophilized to give 419 mg of disodium 7β-[(Z)-2-(2-amino-4-thiazolyl)-2-[[(R  S)-(carboxy)(3,4-dihydroxyphenylthio)methoxy]imino]acetamido]-3-(1,2,3-thiadiazol-5-yl)thiomethyl-3-cephem-4-carboxylate.

IR spectrum $\nu_{max}^{KBr}$ (cm$^{-1}$): 1768.
Mass spectrum FAB (Pos.): 742.
NMR spectrum (in D$_2$O): δ(ppm): 3.31,3.66(2H,AB pattern CH$_2$ at 2 position), 3.92, 4.39(2H,AB pattern, —CH$_2$S—), 5.11, 5.12(1H, each d, C$\underline{H}$ at 6 position), 5.67,5.70(1H,each d, C$\underline{H}$ at 7 position), 5.82,5.84(1H,each s,

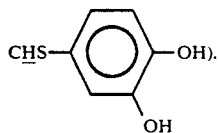

6.83,6.85(1H, each s,

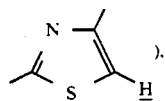

6.9-7.1(3H, m,

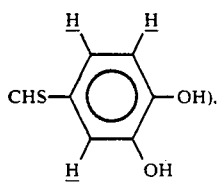

8.69(S, 1H,

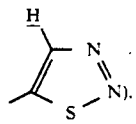

EXAMPLE 24

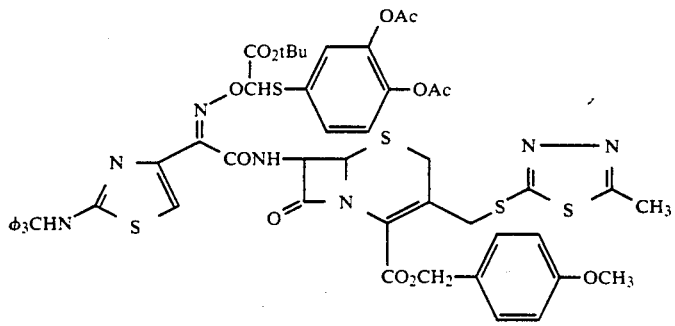

In 8 ml of methylene chloride was dissolved 920 mg of (Z)-2-(2-tritylamino-4-thiazolyl)-2-[[(tert-butoxycarbonyl)(3,4-diacetoxyphenylthio)methoxy]imino]acetate and was added 250 mg of phosphorus pentachloride at —20° C. Methylene chloride solution of acid chloride was obtained by stirring the reaction solution for 1 hr. at —20° C. Meanwhile, in 10 ml of methylene chloride was suspended 464 mg of p-methoxybenzyl-7amino-3-(5-methyl-1,3,4-thiadiazol-2-yl)thiomethyl-3-cephem-4-carboxylate, and was added 0.4 ml of pyridine at —60° C. The previous acid chloride-methylene chloride solution was added to the obtained solution at —60° C. After stirring for 10 min., the temperature was raised to —20° C., and 5 ml of 1N hydrochloric acid was added, and the aqueous layer was extracted with methylene chloride. The organic layer was washed with saturated saline solution and dried over anhydrous magnesium sulphate. Under the reduced pressure, the solvent was removed to obtain a crude product, which was column chromatographed by eluting with ethyl acetate-chloroform to give p-methoxybenzyl 7β-[(Z)-2-(2-tritylamino-4-thiazolyl)-2-[[(R  S)-(tert-butoxycarbonyl)(3,4-diacetoxyphenylthio)methoxy]imino]acetamido]-3-(5-methyl-1,3,4-thiadiazol-2-yl)thiomethyl-3-cephem-4-carboxylate.

IR spectrum $\nu_{max}^{KBr}$ (cm$^{-1}$): 1780.
Mass spectrum FAB (Pos.): 1213.
NMR spectrum (in DMSO-d$_6$): δ(ppm): 1.24(9H,s,t-Bu), 2.24(6H, s, OAc), 2.64(3H,s,

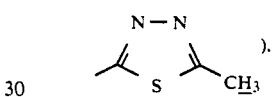

3.50,3.74(2H,AB pattern, CH$_2$ at 2 position), 3.74(s,3H,OCH$_3$), 4.10,4.57(2H,$\overline{AB}$ pattern, —CH$_2$S at 3 position), 5.$\overline{10}$-5.19(3H,m,CH at 6 position and $\overline{CH}_2$ at benzyl position), 5.60-5.68($\overline{1H}$,m,CH at 7 position), 5.78,5.79(1H,each s, C$\underline{H}$S—), 6.78,(1H, s,

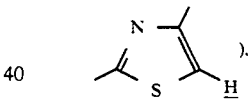

6.88,7.20-7.48(22H, Tr

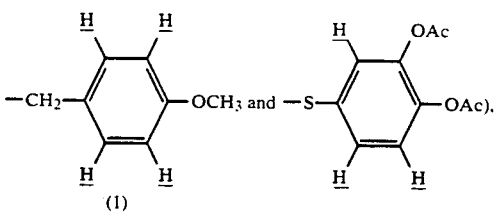

(1)

8.86(1H,s, N$\underline{H}$Tr), 9.70(1H, d,CON$\underline{H}$).

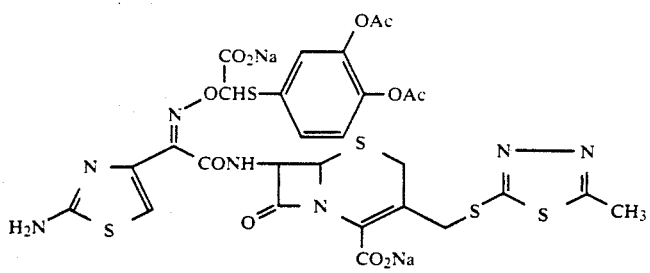

(2)

468 mg of p-Methoxybenzyl 7β-[(Z)-2-(2-tritylamino-4-thiazolyl)-2-[[(R S)-(tert-butoxycarbonyl)(3,4-diacetoxyphenylthio)methoxy]imino]acetamido]-3-(5methyl-1,3,4-thiadiazol-2-yl)thiomethyl-3-cephem-4-carboxylate obtained from (1) was dissolved in 2 ml of methylene chloride and 0.4 ml of anisole, and stirred for 1 hr. at the room temperature after adding dropwise 6 ml of trifluoroacetate under ice-cooling. Under the reduced pressure, the residue obtained by evaporating off trifluoroacetate and methylene chloride was powdered by adding ether and filtered off. After this powder was dissolved by adding 5 ml of trifluoroacetate and 2.5 ml of water, and stirred for 2 hrs. at the room temperature, trifluoroacetate and water were evaporated off under the reduced pressure. The residue was powdered by adding ethyl ether and filtered off to give 297 mg of powder. After this powder was dissolved in diluted sodium hydrogen carbonate aqueous solution, the aqueous solution was adsorbed on Diaion HP-20 and eluted with water, followed by 10% methanol. The fraction containing the desired product was collected, concentrated and lyophilized to give 80 mg of disodium 7β-[(Z)-2-(2-amino-4-thiazolyl)-2-[[(R S)-(carboxy)(3,4-diacetoxyphenylthio)methoxy]imino]acetamido]-3-(5methyl-1,3,4-thiadiazol-2-yl)thiomethyl-3-cephem-4-carboxylate.

IR spectrum $\nu_{max}^{KBr}$ (cm$^{-1}$): 1770.
Mass spectrum FAB (Pos.): 840 (2Na salt).
NMR spectrum (in DMSO-d$_6$) δ(ppm): 2.24(6H, s, OAc), 2.65(3H,s,

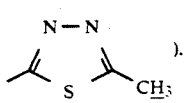

3.52,3.70(2H,AB pattern, C$\underline{H}_2$ at 2 position), 3.70(s,3H,OC$\underline{H}_3$), 4.10,4.57(2H,AB pattern, —C$\underline{H}_2$S at 3 position), 5.13–5.16(1H,m,C$\underline{H}$ at 6 position), 5.70–5.80(1H,m,CH at 7 position), 5.92,5.94(1H,each s, C$\underline{H}$S—), 6.82,(1H, s,

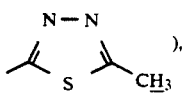

7.10–7.30(1H,m), 7.42–4.50(1H,m), 7.52–7.60(1H,m), 9.75(1H, d,CON$\underline{H}$).

EXAMPLE 25

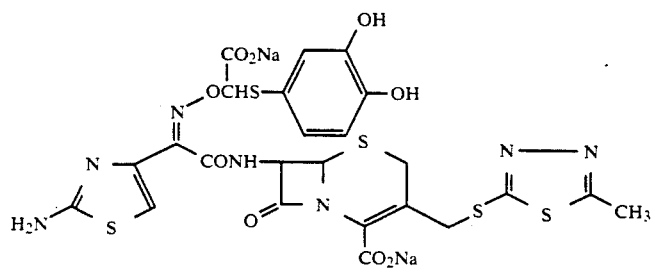

76 mg of the compound obtained from Example 24 was dissolved in 1 ml of saturated sodium bicarbonate aqueous solution and stirred for 1.5 hrs. The reaction solution was adsorbed on Diaion HP-20, and eluted with water, and the fraction containing the desired product was collected. The collected fraction was concentrated and lyophilized to give 22 mg of disodium 7β-[(Z)-2-(2-amino-4-thiazolyl)-2-[[(R S)-(carboxy)(3,4-dihydroxyphenylthio)methoxy]imino]acetamido]-3-(5-methyl-1,3,4-thiadiazol-2-yl)thiomethyl-3-cephem-4-carboxylate.

IR spectrum $\nu_{max}^{KBr}$ (cm$^{-1}$): 1766.
Mass spectrum FAB (Pos.): 756 (2Na salt).
NMR spectrum (in DMSO-d$_6$) δ(ppm): 2.85(3H, s,

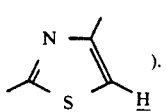

3.30,3.55(2H,AB pattern, C$\underline{H}_2$ at 2 position), 4.27,4.60(2H,AB pattern, —C$\underline{H}_2$S at 3 position), 4.94–5.00(1H,m,C$\underline{H}$ at 6 position), 5.42–5.48(1H,m, CH at 7 position), 5.56(1H,s, C$\underline{H}$S—), 6.50–6.70(1H,m), 6.82,(1H, s, 7.36–7.44(1H,m), 7.46–4.56(1H,m), 9.75(1H, d,CON$\underline{H}$).

EXAMPLE 26

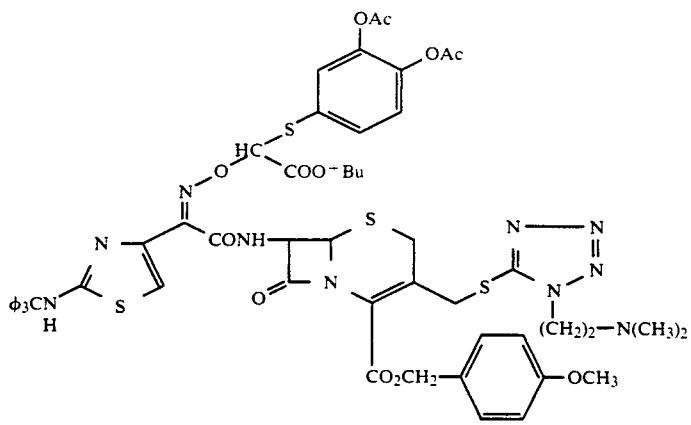
(1)

To 1.21 g of p-methoxybenzyl 7β-[(Z)-2-(2-tritylamino-4-thiazolyl)-2-[[(R S)-(tert-butoxycarbonyl)(3,4-diacetoxyphenylthio) methoxy]imino]acetamido]-3-chloromethyl-3-cephem-4-carboxylate were added 40 ml of carbon tetrachloride and 16 ml of acetone, and then dissolved. 178 mg of sodium iodide was added therein and stirred for 1 hr. at the room temperature. The reaction solution was washed two times with cold 5% sodium thiosulfate aqueous solution, followed by saturated saline solution, and the solvent was evaporated off under the reduced pressure after drying over anhydrous magnesium sulfate.

The residue was dissolved by adding 30 ml of acetone and acetone (8 ml) solution of 252 ml of sodium 1-(2-dimethylaminoethyl)-5-mercaptotetrazole was added to the residue under ice-cooling and stirred for 2 hrs. at 0°-4° C. The reaction solution to which ethyl acetate was added was washed repeatedly with water, and then dried over anhydrous magnesium sulfate. Under the reduced pressure, the solvent was evaporated off to obtain a crude product, which was column chromatographed by eluting with ethyl acetate to give 478 mg of p-methoxybenzyl 7β-[(Z)-2-(2-tritylamino-4-thiazolyl)-2-[[(R S)-(tert-butoxycarbonyl)(3,4-diacetoxyphenylthio)methoxy]imino]acetamido]-3-[1-(2-dimethylaminoethyl)-5-tetrazolyl]thio-methyl-3-cephem-4-carboxylate.

IR spectrum $\nu_{max}^{KBr}$ (cm$^{-1}$): 1784.
Mass spectrum FAB (Pos.): 1255.
NMR spectrum (in CDCl$_3$) δ(ppm): 1.34, 1.40(9H,s,t-Bu), 2.23,2.29(12H, each s, NCH$_3$ and OAc), 2.7–2.85(4H,m,CH$_2$CH$_2$NCH$_3$), 3.6(2H,AB,CH$_2$ at 2 position), 3.77(s,3H,S,OCH$_3$), 4.17–4.4(2H,m, CH$_2$S— at 3 position), 4.94(1H,d,CH at 6 position), 5.11–5.34(2H,AB pattern,

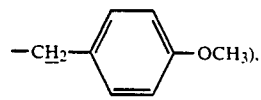

5.74,5.77(1H,each dd, CH at 7 position), 5.97,6.0(1H,each s, —OCH,COO—Bu), 6.82(1H, s,

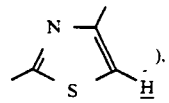

6.8–7.6(22H,m,Tr,

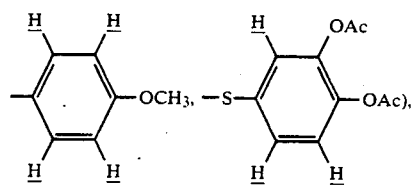

8.02,8.09(1H,each d, CONH).

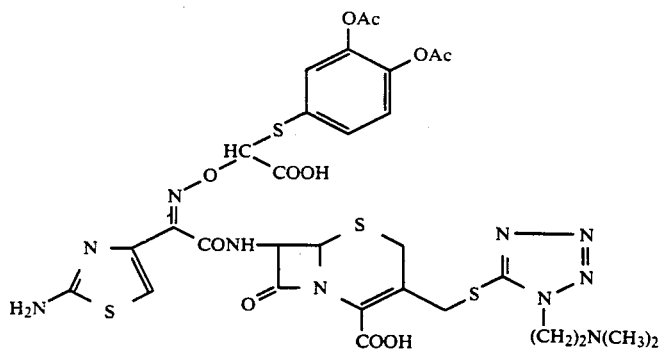
(2)

To 2 ml of methylene chloride was dissolved 467 mg of the compound obtained from (1) and added 50 ml of 80% acetic acid solution, and the stirring was effected for 3 hrs. at 37° C. Under the reduced pressure, the solvent was evaporated off and the residue was powdered by adding ether and filtered off. This powder was dissolved by adding 2 ml of methylene chloride, 0.5 ml of anisole and 5 ml of trifluoroacetate and stirred for 1 hr. at the room temperature. The solvent was evaporated off under the reduced pressure and the residue was powdered by adding ether, filtered up, and then, dried under the reduced pressure to give 264 mg of a crude product.

210 mg of the crude product was suspended in 50 ml of water and dissolved by adding 1N hydrochloric acid. This solution was adsorbed on Diaion HP-20 and eluted with water, followed by methanol solution with sequentially increasing their proportion. The fraction containing the desired product was collected, concentrated, and then lyophilized to give 120 mg of 7β-[(Z)-2-(2-amino-4-thiazolyl)-2-[[(R S)-(carboxy)(3,4-diacetoxyphenylthio)methoxy]imino]acetamido]-3-[[(2-dimethylaminoethyl)-5-tetrazolyl]thiomethyl-3-cephem-4-carboxylate.

IR spectrum $\nu_{max}^{KBr}$ (cm$^{-1}$): 1772.
Mass spectrum FAB (Pos.): 837.
NMR spectrum (in DMSO-d$_6$) δ(ppm): 2.26(6H,s,OAc), 2.57,2.6(6H, each s, NCH$_3$), 3.14-3.94(6H,m,CH$_2$CH$_2$NCH$_2$ and —CH$_2$ at 2 position), 4.29-4.6(2H,m, —CH$_2$S at 3 position), 5.14(1H,d,—CH at 6 position), 5.77,5.89(1H,each dd, —CH at 7 position), 5.94,5.97(1H,each s, —OCH COOH), 6.89(1H, s,

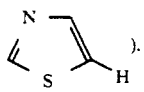

7.2-7.46(3H,m,

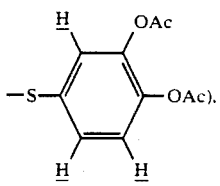

10.71,10.69(1H,each d, CONH).

EXAMPLE 27

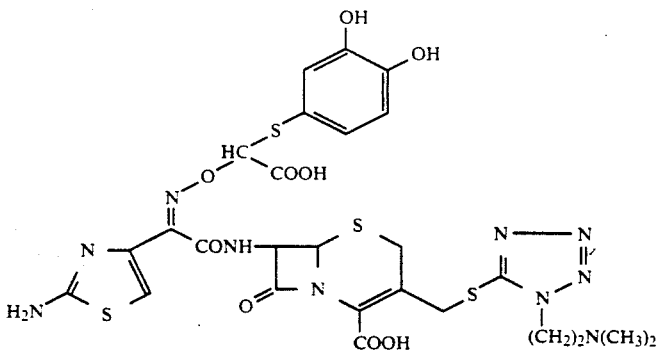

100 ml of the compound obtained from Example 26 was suspended in 10 ml of water, and 5 ml of saturated sodium hydrogen carbonate aqueous solution was added therein and dissolved, and the stirring was effected for 2 hrs. and 20 min. The reaction solution was made to be acidic (pH=2) by adding 1N hydrochloric acid, and adsorbed on Diaion HP-20, and eluted with water, followed by methanol solution with sequentially increasing their proportion. The fraction containing the desired product was collected, concentrated, and then lyophilized to give 53 mg of 7β-[(Z)-2-(2-amino-4-thiazolyl)-2-[[(R S)-(carboxy)(3,4-hydroxyphenylthio)methoxy]imino]acetamido]-3-[1-(2-dimethylaminoethyl)-5-tetrazolyl]thiomethyl-3-cephem-4-carboxylate.

IR spectrum $\nu_{max}^{KBr}$ (cm$^{-1}$): 1772.
Mass spectrum FAB (Pos.): 753.
NMR spectrum (in DMSO-d$_6$). δ(ppm): 2.57,2.6(6H,each S, NCH$_3$), 3.1-4.1(6H,m,CH$_2$CH$_2$N and CH$_2$ at 2 position), 4.28-4.68(2H,m, CH$_2$S— at 3 position), 5.13,5.14 (1H,each d,CH at 6 position), 5.62,5.65(1H,each s, —OCHCOOH), 5.77,5.91(1H,each dd, CH at 7 position), 6.70,6.71(1H,each s,

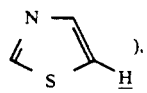

6.6-7.0(3H,m,

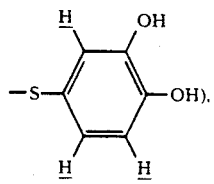

10.6 (1H, d, CONH).

EXAMPLE 28

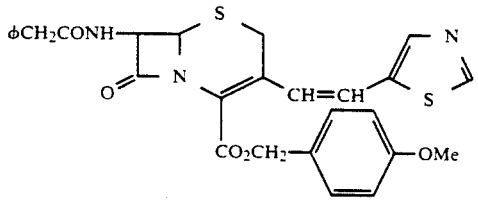

To 12 ml of dimethyl formamide were dissolved 2.0 g (3.46 mmol) of p-methoxybenzyl 7β-phenylacetamido-3-iodomethyl-3-cephem-4-carboxylate and 0.95 g (3.62 mmol) of triphenylphosphine, and the reaction was effected for 1 hr. at the room temperature. The reaction solution was concentrated under the reduced pressure, and powdered with isopropyl ether. The powder was filtered off and dissolved by adding 5 ml of methylene chloride, and 0.39 g (3.46 mmol) of 5-formylthiazol, and further 5 ml of saturated sodium hydrogen carbonate aqueous solution were added therein, and the stirring was effected for 24 hrs. at the room temperature. The layer of methylene chloride was separated and the aqueous layer were extracted with methylene chloride. The layers of methylene chloride were combined, washed with saturated saline solution, dried over anhydrous magnesium sulfate, and then the solvent was evaporated off to give 3.4 g of a caramel.

The caramel was column chromatographed on silica gel by eluting with chloroform to give 1.45 g of p-methoxybenzyl 7β-phenylacetamido-3-[2-(5-thiazolyl)-vinyl]-3-cephem-4-carboxylate.

NMR spectrum (in CDCl$_3$—CD$_3$OD) δ(ppm): 3.20-3.56(2H,m,

).

3.68-3.84(5H,m,—COC$\underline{H}_2$—+—OMe),
5.00,5.08(1H,each d,$\underline{C}H$ at 6 position),
5.10,5.24(2H,each s, COOC$\underline{H}_2$—), 5.76,5.83(1H,each dd, C$\underline{H}$ at 7 position), 6.31,6.62(each d,

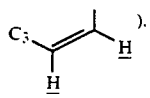
).

6.81,6.89(2H,each d,

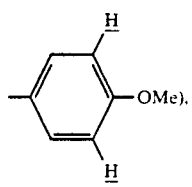
).

7.16-7.90(9H,m,

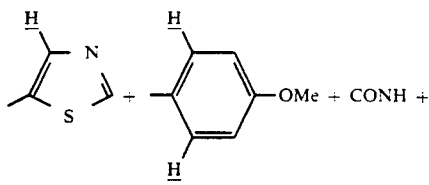

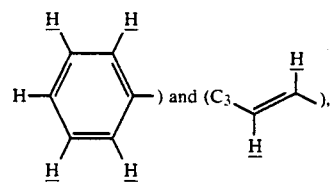

8.67,8.69(1H,each s,

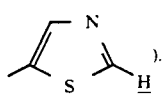
).

Mass spectrum FAB (Pos.): 548 (M+H)$^+$.

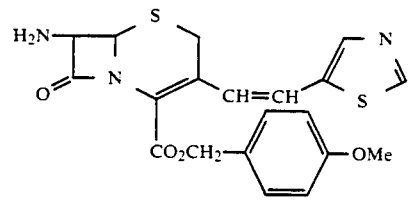

To 20 ml of methylene chloride were dissolved 1.37 g (6.58 mmol) of phosphorus pentachloride and 1.77 ml (21.9 mmol) of pyridine, and 1.20 g (2.19 mmol) of p-methoxybenzyl 7β-phenylacetamido-3-[2-(5-thiazolyl)-vinyl]-3-cephem-4-carboxylate with 7 ml of methylene chloride were added therein at −30° C. After stirring for 3 hrs. under ice-cooling, 20 ml of methanol was added at −50° C. After reacting for 1 hr. under ice-cooling, the reaction solution was added to 45 ml of saturated saline solution and 45 ml of methylene chloride under ice-cooling, and stirred for 1 hr. as it was. The reaction solution was separated, and the aqueous layer was extracted with methylene chloride. The layers of methylene chloride were combined, washed with saturated sodium hydrogen carbonate aqueous solution, and dried over anhydrous magnesium sulfate, and then, the solvent was evaporated off to give 1.51 g gel by eluting with chloroform-ethyl acetate to give 430 mg of p-methoxybenzyl 7β-amino-3-[2-(5-thiazolyl)vinyl]-3-cephem-4-carboxylate.

NMR spectrum (in CDCl$_3$): δ(ppm): 2.05 (2H,brs, —N$\underline{H}_2$), 3.26-3.66(2H,m,

).

3.80,3.82(3H,each s,—OC$\underline{H}_3$), 4.76,4.82(1H,each d, C$\underline{H}$ at 6 position), 5.01,5.08(1$\underline{H}$,each d, C$\underline{H}$ at 7 position), 5.27,5.28(2H,each s, COOC$\underline{H}_2$—), 6.32,6.63(each d,

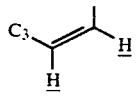

12Hz), 6.83,6.91,7.21,7.39(4H,each d,

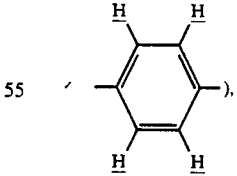

6.98,7.38(each d,

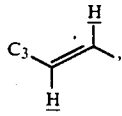

16Hz), 7.72,7.80(1H,each s,

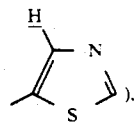

8.69, 8.71(1H,each s, y)imino]acetamido]-3-[-2-(5-thiazolyl)vinyl]-3-cephem-4-carboxylate.

NMR spectrum (in CDCl$_3$) δ(ppm): 1.63(1H,brs), 2.16-2.30(6H,m), 2.96-3.60(2H,m), 3.76-3.80(3H,m), 4.93,4.98,5.03,5.10(1H,each d), 5.08,5.25(2H,each s), 5.72-5.95(1H,m), 5.98-6.63(2H,m), 6.74-7.51(35H,m), 7.69,7.70,7.80,7.82 (1H,each s), 7.98,8.05,8.11,8.27 (1H,each d), 8.46,8.56,8.66,8.67(1H,each s).

Mass spectrum FAB (Pos.): 1257 (M+H)$^+$.

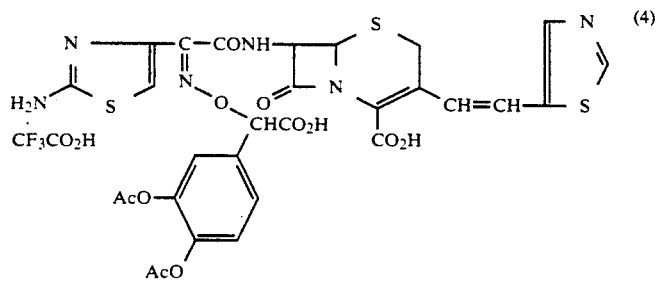

(4)

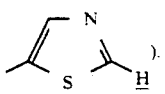

Mass spectrum FAB (Pos.): 430 (M+H)$^+$.

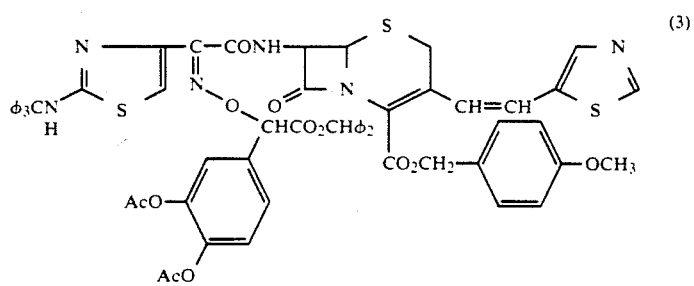

(3)

To 1 ml of methylene chloride were dissolved 199 mg (0.235 mmol) of (Z)-2-(tritylamino-4-thiazolyl)-2-[di-phenylmethoxycarbonyl(3,4-diacetoxyphenyl)methox-y]imino]acetate and 51.4 mg (0.247 mmol) of phosphorus pentachloride under ice-cooling, and the solution was reacted for 30 min. as it was. After this solution was added to a solution of 101 mg (0.235 mmol) of p-methoxybenzyl 7β-amino-3-[2-(5-thiazolyl)vinyl]-3-cephem-4-carboxylate and 0.095 ml (1.17 mmol) of pyridine dissolved in 3 ml of methylene chloride at −60° C., the reaction was effected for 1 hr. while increasing the temperature to −30° C. Then, 1.18 ml of 1N hydrochloric acid was added at −30° C.

The reaction solution to which water was added was extracted three times with methylene chloride, and the organic layer was washed with saturated saline solution and dried over anhydrous magnesium sulfate, and then the solvent was evaporated off to give 330 mg of a caramel. The caramel was column chromatographed on silica gel by eluting with chloroform-ethyl acetate to give 220 mg of p-methoxybenzyl 7β-[(Z)-2-(2-tritylamino-4-thiazolyl)-2-[[(R S)-(diphenylmethoxycarbonyl)(3,4-diacetoxyphenyl)methox-y]imino]acetamido]-3-[-2-(5-thiazolyl)vinyl]-3-cephem-4-carboxylate.

NMR spectrum (in CDCl$_3$) δ(ppm): 1.63(1H,brs), 2.16-2.30(6H,m), 2.96-3.60(2H,m), 3.76-3.80(3H,m), 4.93,4.98,5.03,5.10(1H,each d), 5.08,5.25(2H,each s), 5.72-5.95(1H,m), 5.98-6.63(2H,m), 6.74-7.51(35H,m), 7.69,7.70,7.80,7.82 (1H,each s), 7.98,8.05,8.11,8.27 (1H,each d), 8.46,8.56,8.66,8.67(1H,each s).

Mass spectrum FAB (Pos.): 1257 (M+H)$^+$.

After 870 mg (0.69 mmol) of p-methoxybenzyl 7β-[(Z)-2-(2-tritylamino-4-thiazolyl)-2-[[(R S)-(diphenylmethoxycarbonyl)(3,4-diacetoxyphenyl)methox-y]imino]acetamido]-3-[-2-(5-thiazolyl)vinyl]-3-cephem-4-carboxylate was dissolved in 9 ml of methylene chloride and 4 ml of anisole, 16 ml of trifluoroacetic acid was added therein under ice-cooling and the reaction solution was reacted for 90 min. as it was. The residue obtained by evaporating off trifluoroacetate under the reduced pressure was powdered with ethyl ether-hexane (1:1). The powder obtained by filtering off was further dissolved in 45 ml of trifluoroacetic acid under ice-cooling, and then, 11 ml of water was added therein, and the reaction was effected for 3 hrs. at the room temperature. The residue obtained by evaporating off trifluoroacetic acid and water under the reduced pressure was powdered by adding ethyl ether, and filtered off to give 404 mg of 7β-[(Z)-2-(2-amino-4-thiazolyl)-2-[[(R S)-(carboxy) (3,4-diacetoxyphenyl)methox-y]imino]acetamido]-3-[-2-(5-thiazolyl)vinyl]-3-cephem-4-carboxylic acid.trifluoroacetate, a crude product.

NMR spectrum (in DMSO-d$_6$): δ(ppm); 2.18-2.30(6H,m), 3.23-4.30(4H, brm), 5.18, 5.22, 5.24, 5.27(1H, each d), 5.60(1H, s), 5.75-5.86(1H, m), 6.28-6.84(2H,m), 7.14-7.50(4H, m), 7.86-7.93(1H, m), 9.00(1H, s), 9.54-9.77(1H, m), 13.0-13.8(2H, br).

Mass spectrum FAB (Pos.): 728 (M$^+$).

IR spectrum $\nu_{max}^{KBr}$ (cm$^{-1}$): 1780.

EXAMPLE 29

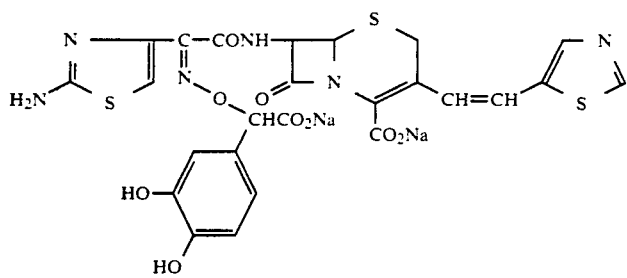

EXAMPLE 30

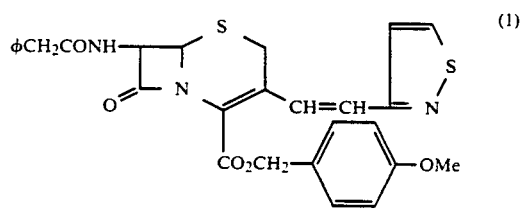

200 mg of 7β-[(Z)-2-(2-amino-4-thiazolyl)-2-[[(R S)-(carboxy)(3,4-diacetoxyphenyl)methoxy]imino]acetamido]-3-[-2-(5-thiazolyl)vinyl]-3-cephem-4-carboxylic acid.trifluoroacetate obtained from Example 28 was dissolved in 20 ml of saturated sodium hydrogen carbonate aqueous solution at the room temperature and the reaction solution was reacted for 4 hrs. as it was. The reaction solution was adsorbed on Diaion HP-20, and eluted with water-methanol, and the fraction containing the desired product was collected, concentrated, and then lyophilized to give 139 mg of disodium 7β-[(Z)-2-(2-amino-4-thiazolyl)-2-[[(R S)-(carboxylate) (3,4-dihydroxyphenyl)methoxy]imino]acetamido]-3-[(EZ)-2-(5-thiazolyl)vinyl]-3-cephem-4-carboxylate.

NMR spectrum (in $D_2O$): δ(ppm); 3.01–3.68(2H,m), 5.07, 5.10, 5.20, 5.22(1H, each d), 5.32–5.42 (1H, m), 5.68–5.78(1H, m), 6.25–7.15 (6H, m), 7.78–7.88(1H, m), 8.76–8.86(1H, m).

Mass spectrum FAB (Pos.): 689 $(M+H)^+$.

IR spectrum $\nu_{max}^{KBr}$ $(cm^{-1})$: 1764.

Disodium 7β-[(Z)-2-(2-amino-4-thiazoyl)-2-[[(RS)-carboxylate)(3,4-dihydroxyphenyl)methoxy]imino]acetamido]-3-[(EZ)-2-(5-thiazolyl)vinyl]-3-cephem-4-carboxylate thus obtained was proved to be a mixture of 4 kinds of isomer, as follows: The product was subjected to high performance liquid chromatography (YMC-PACK A-302 ODS 4.6×150 mm) and was eluted with aqueous 50 mM $KH_2PO_4/CH_3CN$ (9:1) to give isomers A, B, C and D (retention time: about 10.5 min., 12 min., 13.5 min. and 16.5 min. respectively). 100 mg of isomer A, 35 mg of isomer B, 109 mg of isomer C and 45.7 mg of isomer D were obtained from 500 mg of the product of the 4 kinds of isomer mixed, after concentrating each fraction separated, adding thereto an excess amount sodium hydrogen carbonate, desalting with Diaion HP-20 and freeze-drying.

NMR

Isomer A (DMSO-$D_6$) (ppm); 3.14, 3.47 (2H, each d), 5.18–5.21 (2H, m), 5.75 (1H, dd), 6.48, 6.60 (2H, each d), 6.64 (1H, d), 6.78–6.86 (4H, m), 7.23 (2H, s), 7.82 (1H, s), 8.98 (1H, s).

Isomer B; 3.55, 3.64 (2H, each d), 5.32 (1H, s), 5.71 (1H, s), 6.71–6.91 (4H, m), 6.99, 7.35 (2H, each d), 7.86 (1H, s), 8.91 (1H, s).

Isomer C; 3.20, 3.45 (2H, each d), 5.18 (1H, d), 5.28 (1H, s), 5.69 (1H, dd), 6.44, 6.67 (2H, each d), 6.63–6.88 (5H, m), 7.25 (2H, s), 7.84 (1H, s), 8.98 (1H, s).

Isomer D; 3.64, 3.83 (2H, each d), 5.17 (1H, d), 5.36 (1H, s), 5.72 (1H, d), 6.73–6.93 (4H, m), 7.17, 7.33 (2H, each d), 7.92 (1H, s), 8.96 (1H, s).

To 20 ml of dimethylformamide were dissolved 3.0 g (6.16 mmol) of p-methoxybenzyl 7β-phenylacetamido-3-chloromethyl-3-cephem-4carboxylate and 1.70 g (6.48 mmol) of triphenylphosphine, and 0.97 g (6.47 mmol) of sodium iodide was added therein, and the stirring was effected for 2 hrs. at the room temperature. The reaction solution was concentrated and dried under the reduced pressure and 10 ml of methylene chloride was added therein. To this solution were added 767 mg (6.78 mmol) of 3-formylisothiazole and 10 ml of saturated sodium hydrogen carbonate aqueous solution, and the stirring was effected for 5.5 hrs. at the room temperature. The layer of methylene chloride was separated, and the aqueous layer was extracted with methylene chloride. The layers of methylene chloride were combined, washed with saturated saline solution; and dried over anhydrous magnesium sulfate, and then, the solvent was evaporated off to give 6.8 g of a caramel. This caramel was column chromatographed on silica gel by eluting with chloroform-ethyl acetate to give 2.48 g of p-methoxybenzyl 7β-phenylacetamido-3-[2-(isothiazol-3-yl)vinyl]-3-cephem-4-carboxylate.

NMR spectrum (in DMSO-$d_6$): δ(ppm); 3.36–3.68(2H, m), 3.76 (3H, s), 5.08(2H, s), 5.24 (1H, d), 5.72(1H, dd), 6.70–6.90(3H, m), 7.06–7.38(6H, m), 7.40–7.68(5H, m), 8.73(1H, d), 9.04(1H, d).

Mass spectrum FAB (Pos.): 548 $(M+H)^+$.

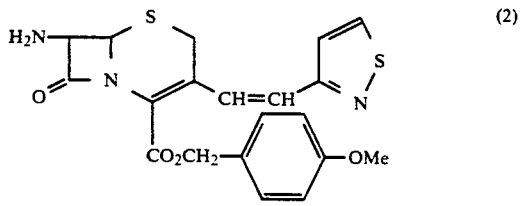

In 13 ml of methylene chloride were dissolved 913 mg of phosphorus pentachloride and 1.18 ml of pyridine, and 800 mg (1.46 mmol) of p-methoxybenzyl 7β-phenylacetamido-3-[2-(isothiazol-3-yl)vinyl]-3-cephem-4-carboxylate with 3.2 ml of methylene chloride were added therein at −30° C. After stirring for 3 hrs. under ice-cooling, the reaction solution was added to 13 ml of methanol at −30° C. After stirring for 1 hr. at the room temperature, the reaction solution was added to 30 ml of saturated saline solution and 30 ml of methylene chloride under ice-cooling, and stirred for 1 hr. as it was. The reaction solution was separated, and the aqueous layer was further extracted with 20 ml of methylene chloride. The layers of methylene chloride were combined, washed with saturated sodium hydrogen carbonate aqueous solution, and dried over anhydrous magnesium sulfate, and then, the solvent was evaporated off to give 1.15 g of a caramel. The caramel was column chromatographed on silica gel by eluting with chloroform-ethyl acetate to give 600 mg of p-methoxybenzyl 7β-amino-3-[2-(isothiazol-3yl)vinyl]-3-cephem-4-carboxylate.

NMR spectrum (in DMSO-d$_6$): δ(ppm); 2.25–2.55(2H, br s), 3.53 (2H, dd), 3.75(3H, s), 4.83 (1H, d), 4.98(2H, s), 5.09 (1H, d), 6.58(4H, dd), 6.88 (1H, d), 7.24(1H, d), 7.31 (1H, d), 9.01(1H, d).

Mass spectrum FAB (Pos.): 430 (M+H)$^+$.

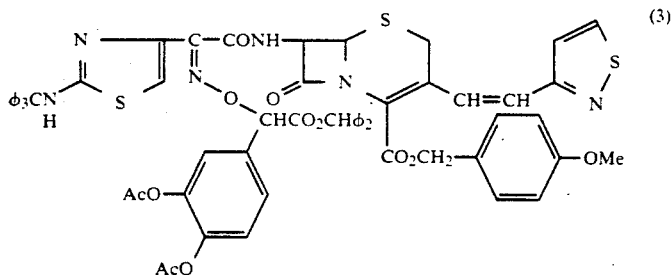
(3)

To 3.5 ml of methylene chloride were added 788 mg (0.931 mmol) of (Z)-2-(2-tritylamino-4-thiazolyl)-2-[diphenylmethoxycarbonyl(3,4-diacetoxyphenyl)methoxy]iminoacetate and 204 mg (0.980 mmol) of phosphorus pentachloride under ice-cooling, and the stirring was effected for 30 min. This solution was added to a solution of 400 mg (0.931 mmol) of p-methoxybenzyl 7β-amino-3-[2-(isothiazol-3-yl)vinyl]-3-cephem-4-carboxylate and 0.376 ml of pyridine dissolved in 12 ml of methylene chloride at −60° C. The temperature of the reaction solution was increased to −30° C. for 1 hr. The reaction solution was cooled to −40° C. and 4.66 ml of 1N hydrochloric acid were added to the solution. The reaction solution to which water was added was extracted three times with methylene chloride, and the organic layer was washed with saturated saline solution and dried over anhydrous magnesium sulfate, and then, the solvent was evaporated off to give 1.0 g of a caramel. The caramel was column chromatographed on silica gel by eluting with chloroform-ethyl acetate to give 76 g of p-methoxybenzyl 7β-[(Z)-2-(tritylamino-4-thiazolyl)-2-[[(R S)-diphenylmethoxycarbonyl)(3,4-diacetoxyphenyl)methoxy]imino]acetamido]-3-[2-(isothiazol-3-yl)vinyl]-3-cephem-4-carboxylate.

NMR spectrum (in CDCl$_3$): δ(ppm); 2.24(6H, br), 3.17, 3.35(2H, each dd), 3.76(3H, s), 4.99, 5.03(1H, each d), 5.11, 5.13(1H, each s), 5.85, 5.87(1H, each dd), 6.60, 6.62(2H, each s), 6.74, 6.78(1H, each s), 6.80–7.80(35H, m), 7.88, 8.05(1H, each d), 7.21(1H, d), 7.44(1H, d), 7.54(1H, d).

Mass spectrum FAB (Pos.): 1256 (M+).

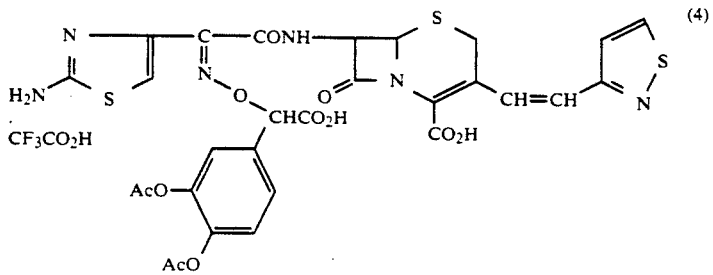
(4)

After 400 mg of p-methoxybenzyl 7β-[(Z)-2-(2-tritylamino-4-thiazolyl)-2-[[(R S)-(diphenylmethoxycarbonyl)(3,4-diacetoxyphenyl)methoxy]imino]acetamido]-3-[2-(isothiazol-3-yl)vinyl]-3-cephem-4-carboxylate were dissolved in 4 ml of methylene chloride and 2 ml of anisole, 8 ml of trifluoroacetate was added therein under ice-cooling, and the reaction solution was reacted for 90 min. as it was. The residue obtained by evaporating off methylene chloride and trifluoroacetate was powdered by using ethyl ether. The powder obtained by filtering off was further added to 24 ml of trifluoroacetate under ice-cooling, and then 6 ml of water was added therein, and the reactants were reacted for 30 min. as they were, and further reacted for 2 hrs. at the room temperature. The residue obtained by evaporating off trifluoroacetate and water under the reduced pressure was powdered by adding ethyl ether and filtered off to give 190 mg of 7β-[(Z)-2-(2-amino-4-thiazolyl)-2-[ [(R S)-(carboxy)(3,4-diacetoxyphenyl)methoxy]imino]acetamido]-3-[2-(isothiazol-3-yl)vinyl]-3-cephem-4-carboxylic acid.trifluoroacetate.

NMR spectrum (in DMSO-d$_6$): δ(ppm); 2.16–2.34 (6H, m), 3.52–3.84(2H, m), 3.90–4.10(2H, br), 5.23, 5.25(1H, each d), 5.61 (1H, s), 5.81, 5.84(1H, each dd), 6.63, 6.65(1H, each s), 6.79(1H, d), 6.83(1H, d), 7.02–7.76(11H, m), 9.04(1H, d), 9.55, 9.73(1H, each d).

Mass spectrum FAB(Pos.): 729 (M+H)$^+$.

IR spectrum $\nu_{max}^{KBr}$(cm$^{-1}$): 1766.

EXAMPLE 31

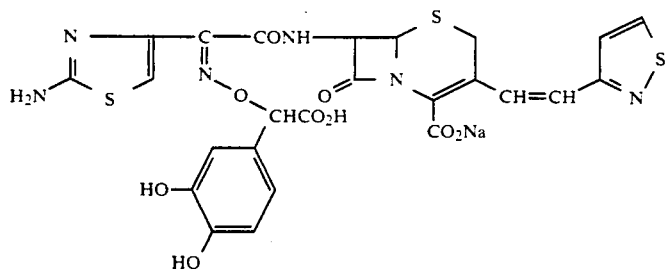

50 mg of 7β-[(Z)-2-(2-amino-4-thiazolyl)-2-[[(R S)-(carboxy)(3,4-diacetoxyphenyl)methox-y]imino]acetamido]-3-[2-(isothiazol-3-yl)vinyl]-3-cephem-4-carboxylic acid·trifluoroacetate obtained from Example 30 were dissolved in 5 ml of saturated sodium hydrogen carbonate aqueous solution at the room temperature, and the reaction solution was reacted for 5 hrs. as it was. The reaction solution was adsorbed on Diaion HP-20, and eluted with water-methanol, and the fraction containing the desired product was collected, concentrated and lyophilized to give 20 mg of disodium 7β-[(Z)-2-(2-amino-4-thiazolyl)-2-[[(R S)-(carboxylate)(3,4-dihydroxyphenyl)methox-y]imino]acetamido]-3-[2-(isothiazol-3-yl)vinyl]-3-cephem-4-carboxylate.

NMR spectrum (in D$_2$O): δ(ppm); 3.00-3.68 (2H, m), 5.13, 5.15(1H, each d), 5.39, 5.40(1H, each s), 5.67, 5.72(1H, each d), 6.48-7.16(4H,m), 7.24-7.60(2H, m), 8.77(1H, d), 8.85(1H, d).

IR spectrum $\nu_{max}^{KBr}$ (cm$^{-1}$): 1758.

EXAMPLE 32

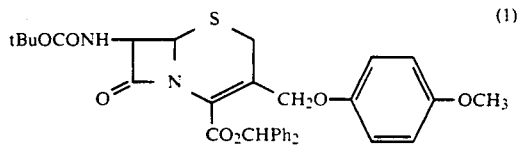 (1)

5.00 g (10.1 mmol) of Diphenylmethyl 7-tert-butoxycarbonylamino-3-hydroxymethyl-3-cephem-4-carboxylate, 7.93 g (30.2 mmol) of triphenylphosphine, and 7.28 g (60.2 mmol) of p-methoxyphenol were dissolved in 25 ml of tetrahydrofuran under argon atmosphere, and the reaction solution was cooled to −40°-35° C., and 4.76 ml (30.2 mmol) of diethyl azodicarboxylate were added dropwise, and then the stirring was effected for 6 hrs. at the same temperature. This solution was added to a suspension of 300 ml of ice cold 1N hydrochloric acid and 300 ml of ethyl acetate, and stirred, and then separated, and the layer of ethyl acetate was washed with water and saturated saline solution, and dried over anhydrous magnesium sulfate. Benzene was added to a caramel obtained by evaporating off the solvent so that the insoluble material was removed by filtering off, and the residue obtained by evaporating off the benzene filtrate was dissolved in diethyl ether. This ether solution was washed with 20% potassium carbonate aqueous solution until unreacted p-methoxyphenol was removed, and further washed with saturated potassium dihydrogen phosphate aqueous solution, water, and saturated saline solution. The layer of ether was dried over anhydrous magnesium sulfate, and then, ether was evaporated off to give 2.80 g of a caramel. The caramel was column chromatographed on silica gel by eluting with benzene-acetone (V:V;100:1), and then, powdered with ether-hexane to give 1.29 g of diphenylmethyl 7-tert-butoxycarbonylamino-3-(4-methoxyphenoxymethyl)-3cephem-4-carboxylate.

IR spectrum $\nu_{max}^{KBr}$ (cm$^{-1}$): 1790.

NMR spectrum (in DMSO-d$_6$): δ(ppm); 1.39 (9H, s, t-Bu) 3.63(2H, s, —CH$_2$— at 2 position), 3.68(3H, s, —OCH$_3$), 4.66(2H, s, —CH$_2$O— at 3 position), 5.11(1H,d,CH at 6 position), 5.55(1H,dd,CH at 7 position), 6.74(4H, AB pattern),

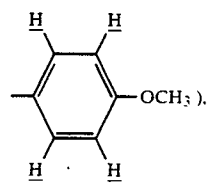

6.94(1H, s, CHPh$_2$), 7.26-7.44(10H, m,—CHPh$_2$), 8.03(1H, d, —NH—).

Mass spectrum FAB(Pos.): 603(M+H)$^+$.

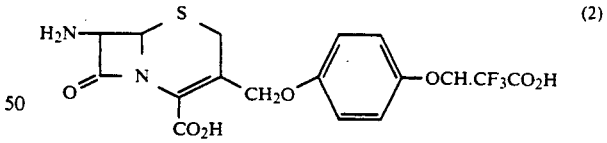 (2)

1.20 g (1.99 mmol) of Diphenylmethyl 7-tert-butoxycarbonylamino-3-(4-methoxyphenoxymethyl)-3-cephem-4-carboxylate obtained from (1) was dissolved in 10 ml of methylene chloride, and 2.2 ml of anisole was added therein, and further 7.7 ml of trifluoroacetate was added under ice-cooling and the reaction solution was stirred for 45 min. at the room temperature. The volatile component was evaporated off under the reduced pressure and the residue was powdered by adding diethyl ether to give 654 mg of 7-amino-3-(4-methoxyphenoxymethyl)-3-cephem-4-carboxylic acid.trifluoroacetate.

IR spectrum $\nu_{max}$ KBr (cm$^{-1}$): 1808.

NMR spectrum (in D$_2$O): δ(ppm); 3.54 (2H, AB pattern, —CH$_2$— at 2 position), 3.80(3H, s, —OCH$_3$), 4.68-4.96(3H, m, —CH$_2$O— at 3 position, CH at 6 position), 5.00(1H, d, CH at 7 position), 6.97(4H, brs

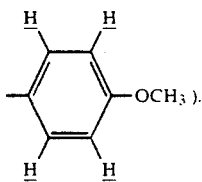

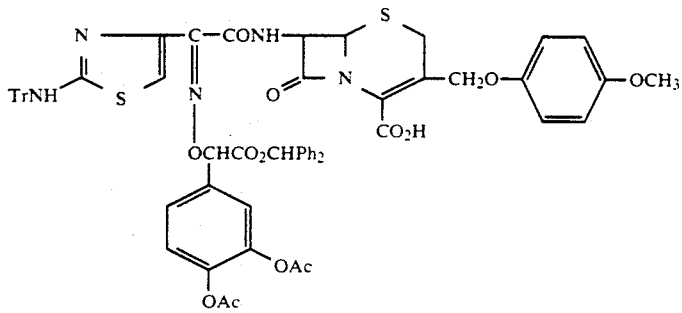

Under argon atmosphere in 10 ml of methylene chloride was dissolved 1.235 g (1.46 mmol) of (Z)-2-(2-tritylamino-4-thiazolyl)-2-[[(diphenylmethoxycarbonyl)(3,4-diacetoxyphenyl)methoxy]imino]acetate, and 0.304 g (1.46 mmol of phosphorus pentachloride was added therein at −25° C. The methylene chloride solution of acid chloride was obtained by stirring the reaction solution for 1 hr. at −20°-15 ° C. Meanwhile, 654 mg (1.46 mmol) of 7-amino-3-(4-methoxyphenoxymethyl)-3-cephem-4-carboxylic acid.trifluoroacetate obtained from (2) was dissolved in 10 ml of methylene chloride under argon atmosphere, and 0.72 ml (2.94 mmol) of N,O-bis(trimethylsilyl) acetamide was added therein at the temperature below 10° C. and the solution was stirred until the homogeneous solution was formed, and then cooled to −65° C., and 0.71 ml (8.78 mmol) of pyridine was added and further the solution of acid chloride prepared previously was added at the same temperature. This solution was stirred for 2 hrs. at −40°-35° C., and then, added to 50 ml of ice cold saturated potassium dihydrogen phosphate aqueous solution. The organic layer was further washed with saturated potassium dihydrogen phosphate aqueous solution, water, and saturated saline solution, and dried over magnesium sulfate, and then the solvent was evaporated off to give 1.74 g of a caramel. The caramel was column chromatographed on silica gel by eluting with chloroform-methanol (V:V;90:10) to give 1.075 g of 7-[(Z)-2-(2-tritylamino-4-thiazolyl)-2-[[(R S)-(diphenylmethoxycarbonyl)(3,4-diacetoxyphenyl)methoxy]imino]acetamido]-3-(4-methoxyphenoxymethyl)-3-cephem-4-carboxylate.

IR spectrum $\nu_{max}^{KBr}$ (cm$^{-1}$): 1774.

NMR spectrum (in DMSO-d$_6$): δ(ppm); 2.26 (6H, s, —OAc), 3.28-3.41(2H, m, —CH$_2$— at 2 position), 3.67(3H, s,—OCH$_3$), 4.78-4.87(3H, m, —CH$_2$O— at 3 position, CH at 6 position), 5.47-5.57(1H, m, CH at 7 position), 5.84, 5.85(1H, each s,

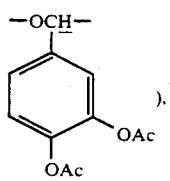

6.72-6.94(6H, m, —C$\underline{H}$Ph$_2$,

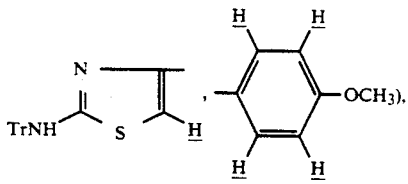

7.14-7.44(28H, m, —CHP$\underline{h}_2$, Tr-,

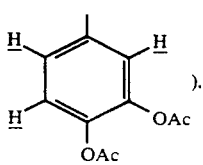

8.64, 8.90(1H, each s, TrN$\underline{H}$—), 9.46, 9.60(1H, each d, —CON$\underline{H}$—).

Mass spectrum FAB(Neg): 1162(M-H)$^-$.

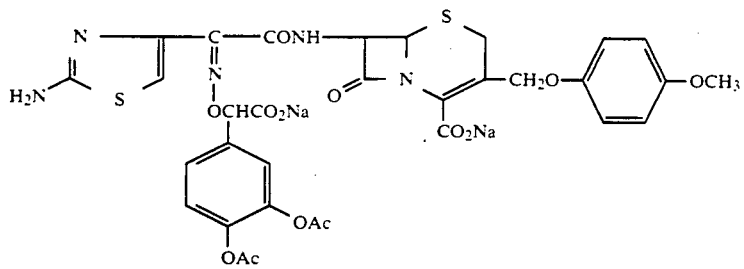

(4)

1.00 g (0.859 mmol) of 7β-[(Z)-2-(2-tritylamino-4-thiazolyl)-2-[[(R S)-(diphenylmethoxycarbonyl)(3,4-diacetoxyphenyl)methoxy]imino]acetamido]-3-(4-methoxyphenoxymethyl)-3-cephem-4-carboxylate obtained from (3) was dissolved in 15 ml of methylene chloride, and 0.94 ml of anisole was added therein, and further 3.3 ml of trifluoroacetate was added under ice-cooling, and the reaction solution was stirred for 1 hr. at the room temperature. The volatile component was evaporated off under the reduced pressure and the residue was powdered by adding diethyl ether and filtered off. Then, the filtrate was dissolved in 15 ml of ice cold trifluoro acetate, and 5 ml of water was added dropwise to this solution at the temperature below 15° C., and the solution was stirred for 3 hrs. at the room temperature. The residue obtained by evaporating off the solvent was powdered by adding diethyl ether to give 627 mg of a crude product. The crude produce was dissolved in 5% sodium hydrogen carbonate aqueous solution, and then, adsorbed on Diaion HP-20 and eluted with water, followed by methanol solution. The fraction containing the desired product was concentrated and lyophilized to give 171 mg of disodium 7β-[(Z)-2-(2-amino-4-thiazolyl)-2-[[(R S)-(carboxylate)(3,4-diacetoxyphenyl)methoxy]imino]acetamido]-3-(4-methoxyphenoxymethyl)-3-cephem-4-carboxylate.

IR spectrum $\nu_{max}^{KBr}$ (cm$^{-1}$): 1768.

NMR spectrum (in D$_2$O): δ(ppm); 2.27, 2.28, 2.31, 2.32(6H, each s, —OAc), 3.23–3.48(2H, m, —CH$_2$— at 2 position), 3.82(3H, s, —OCH$_3$), 4.71–5.06(3H, m, —CH$_2$O— at 3 position, CH at 6 position), 5.57, 5.57(1H, each s,

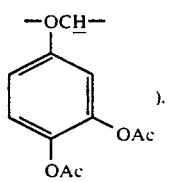

).

5.67–5.73(1H, each d, CH at 7 position), 6.89–7.06(8H, m

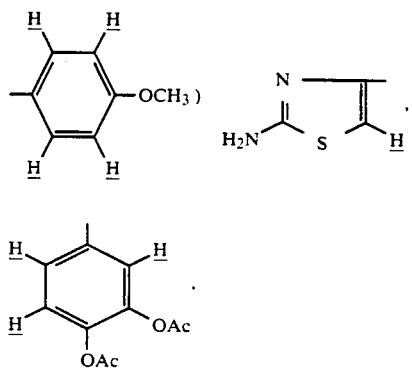

EXAMPLE 33

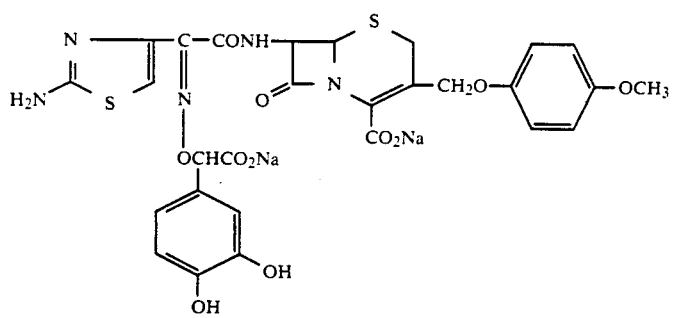

100 mg (0.125 mmol) of Disodium 7β-[(Z)-2-(2-amino-4-thiazolyl)-2-[[(R S)-(carboxylate)(3,4-diacetoxyphenyl)methoxy]imino]acetamido]-3-(4-methoxyphenoxymethyl)-3-cephem-4-carboxylate obtained from Example 32 was dissolved in saturated sodium hydrogen carbonate aqueous solution and then the solution was stirred for 1 hr. and adsorbed on Diaion HP-20 as it was. The solution was eluted with water, followed by methanol solution and the fraction containing the desired product was concentrated and lyophilized to give 77 mg of disodium 7β-[(Z)-2-(2-amino-4-thiazolyl)-2-[[(R S)-(carboxylate)(3,4-dihydroxyphenyl)methoxy]imino]acetamido]-3-(4-methoxyphenoxymethyl)-3-cephem-4-carboxylate.

IR spectrum $\nu_{max}^{KBr}$ (cm$^{-1}$): 1768.

NMR spectrum (in D$_2$O): δ(ppm); 3.22–3.52 (2H, m, —CH$_2$— at 2 position), 3.81(3H, s, —OCH$_3$), 4.70–5.02(3H,m, —CH$_2$O— at 3 position, CH at 6 position), 5.41(1H, s,

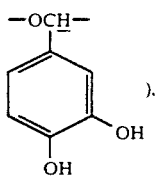

5.60–5.71(1H, each d, CH at 7 position), 6.82–7.02(8H, m,

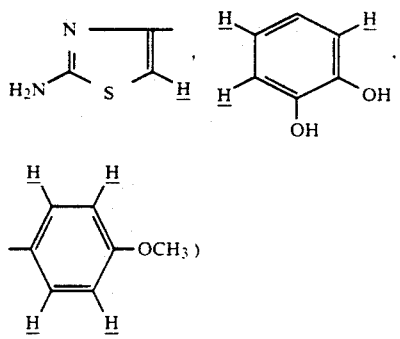

Mass spectrum FAB (Pos.): 716(M+H)+.

EXAMPLE 34

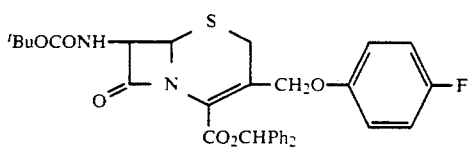

By using the same procedure as described in Example 32(1), except that 6.78 g (60.5 mmol) of p-fluorophenol was substituted for p-methoxyphenol, 1.68 g of phenylmethyl 7-tert-butoxycarbonylamino-3-(4-fluorophenoxymethyl)-3-cephem-4-carboxylate was obtained.

NMR spectrum (DMSO-$d_6$): δ(ppm); 1.41(9H, s, -$^t$Bu) 3.65(2H, ABpattern, —CH$_2$— at 2 position) 4.65(2H, s, —CH$_2$O— at 3 position) 5.13(1H, d, CH at 6 position) 5.57(1H, dd, CH at 7 position) 6.68–7.09(4H, m,

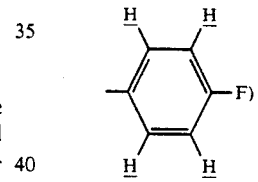

6.92(1H, s, —CHPh$_2$) 7.24–7.44(10H, m, —CHPh$_2$) 8.04(1H, d, —NH—).

Mass spectrum FAB(Pos.): 591(M+H)+.

(2)

By using the same procedure as described in Example 32(2), but substituting 1.60 g (2.71 mmol) of diphenylmethyl 7-tert-butoxycarbonylamino-3-(4-fluorophenoxymethyl)-3-cephem-4-carboxylate for diphenylmethyl 7-tert-butoxycarbonylamino-3-(4-methoxyphenoxymethyl)-3-cephem-4-carboxylate, 944 mg of 7-amino-3-(4-fluorophenoxymethyl)-3-cephem-4-carboxylic acid trifluoroacetate was obtained.

NMR spectrum (D$_2$O): δ(ppm): 3.55(2H, AB pattern, —CH$_2$— at 2 position) 4.73–4.94(3H, m, —CH$_2$O— at 3 position, CH at 6 position) 5.01(1H, d, CH at 7 position) 6.96–7.13(4H, m, Mass Spectrum FAB(Pos.): 325(M+H)+.

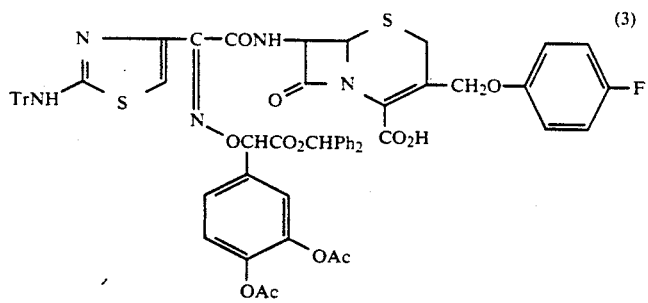

By using the same procedure as described in Example 32(3), but substituting 1.820 g (2.15 mmol) of 7-amino-3-(4-fluorophenoxymethyl)-3-cephem-4-carboxylic acid trifluoroacetate for 7-amino-3-(4-methoxyphenoxymethyl)-3-cephem-4-carboxylic acid trifluoroacetate, 1.823 g of 7β-[(Z)-2-(2-tritylamino-4-thiazolyl)-2-[[(R S)-(diphenylmethoxycarbonyl)(3,4-diacetoxyphenyl)methoxy]imino]acetamido]-3-(4-fluorophenoxymethyl)-3-cephem-4-carboxylic acid was obtained.

NMR spetrum (DMSO-$a_6$): δ(ppm); 2.27(6H, s, —OAc) 3.28–3.44(2H, s, —CH$_2$— at 2 position) 4.87–4.97(3H, m, —CH$_2$O— at 3 position, CH at 6 position). 5.46–5.56(1H, m, CH at 7 position) 5.83, 5.84(1H, each s, 6.63–7.09(6H, m, —CHPh₂,

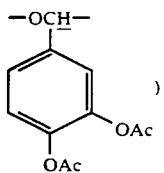

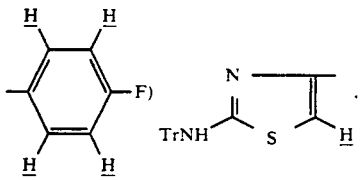

7.16–7.40(28H, m, —CHPh₂, Tr—,

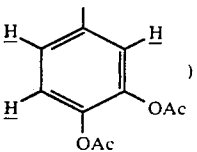

8.63, 8.89(1H, each s, TrNH—) 9.46. 9.59(1H, each d, —CONH—).
Mass spectrum FAB(Neg.):1150(M—H)⁻

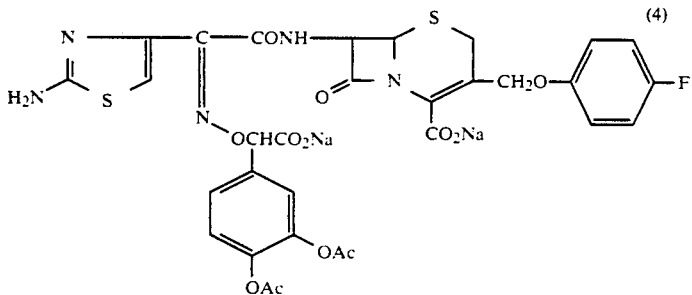

By using the same procedure as described in Example 32(4), but substituting 500 mg (0.434 mmol) of 7β-[(Z)-2-(2-tritylamino-4-thiazolyl)-2-[[(R    S)-(diphenylmethoxy carbonyl)(3,4-diacetoxyphenyl)methoxy]imino]acetamido]-3-(4-fluorophenoxymethyl)-3-cephem-4-carboxylic acid for 7β-[(Z)-2-(2-tritylamino-4-thiazolyl)-2-[[(R    S)-(diphenylmethoxycarbonyl)(3,4-diacetoxyphenyl)methoxy]imino]acetamido]-3-(4-methoxyphenoxymethyl)-3-cephem-4-carboxylic acid, 101 mg of 7β-[(Z)-2-(2-amino-4-thiazolyl)-2-[[(R,S)-(carboxylate)    (3,4-diacetoxyphenyl)methoxy]imino]acetamido]-3-(4-fluorophenoxymethyl)-3-cephem-4-carboxylate was obtained.

IR spectrum $\nu_{max}^{Kbr}$ (cm⁻¹):1766.

NMR spectrum (D₂O); δ(ppm); 2.26, 2.30, 2.31, 2.34(3H, each s, —OAc) 3.23–3.48(2H, m, —CH₂— at 2 position) 4.55–5.05(3H, m, —CH₂O— at 3 position, CH at 6 position) 5.57(1H, s,

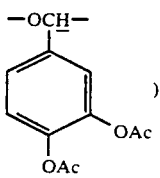

5.66–5.73(1H, each d, CH at 7 position) 6.84–7.13(8H, m,

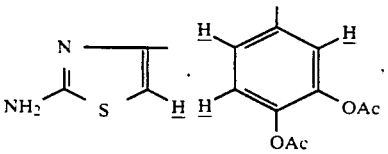

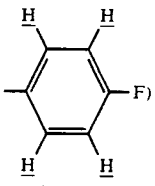

(4)

Mass spectrum FAB (Neg.):742(M—H)⁻

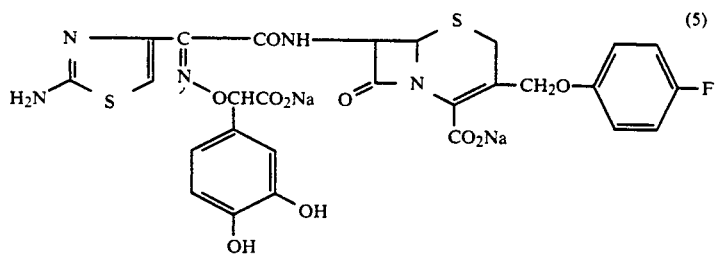

(5)

By using the same procedure as described in Example 33, except that 74 mg(0.094 mmol) of disodium 7β-[(Z)-2-(2-amino-4-thiazolyl)-2-[[(R    S)-(carboxylate)(3,4-diacetoxyphenyl)methoxy]imino]acetamido]-3-(4-fluorophenoxymethyl)-3-cephem-4-carboxylate was substituted for disodium 7β-[(Z)-2-(2-amino-4- thiazolyl)-2-[[(R S)-(carboxylate)-(3,4-diacetoxyphenyl)methoxy]imino]acetamido]-3-(4-methoxyphenoxymethyl)-3-cephem-4-carboxylate, 32 mg of disodium 7β-[(Z)-2-(2-amino-4-thiazolyl)-2-[(R,S)-(carboxylate)(3,4-dihydroxyphenyl)methoxyl-]imino]acetamido]-3-(4-fluorophenoxymethyl)-3-cephem-4-carboxylate was obtained.

IR spectrum $\nu_{max}^{KBr}$ (cm$^{-1}$):1768.

NMR spectrum (D$_2$O): δ(ppm); 324–3.55(2H, m, —CH$_2$— at 2 position) 4.55–5.02(3H, m, —CH$_2$O— at 3 positions. CH at 6 position) 5.38(1H, s,

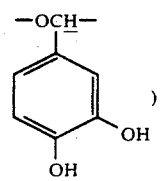
)

5.65–5.70(1H, each d, CH at 7 position) 6.77–7.12(3H, m,

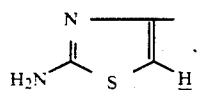

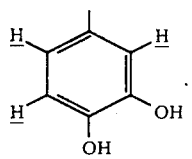

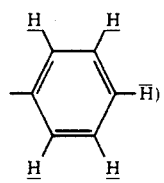

Mass spectrum FAB(Pos.):704(M+H).

EXAMPLE 35

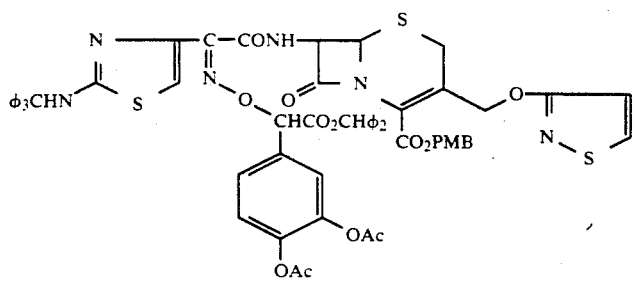
(1)

1.41 g of p-methoxybenzyl 7β-[(Z)-2-(2-tritylamino-4-thiazolyl)-2-[[(RS)-(dipheylmethoxycarbonyl)(3,4-diacetoxyphenyl)methoxyimino]acetamido]-3-chloromethyl-3-cephem-4-carboxylate was dissolved in a mixed solvent of 40 ml of carbon tetrachloride and 16 ml of acetone, and 213 mg of sodium iodide was added and this mixture was stirred for 1 hr. at the room temperature.

The reaction solution was washed with 40 ml of 5% aqueous thiosodium sulfate solution and then with 50 ml of saline solution, and thereafter dried over magnesium sulfate.

The solvent was evaporated and to the resultant residue was added 20 ml of acetone to dissolve it and 240 mg of 3-hydroxyisothiazole was added. And then, under ice-cooling, after adding 261 mg of potassium carbonate, the reactant was stirred for 4 hrs. at the same temperature. After completion of the reaction, the solvent was evaporated under the reduced pressure and the resultant solid material is subjected to silica gel column chromatography eluting with benzene-ethyl acetate (volume ratio 3:1) to give 226 mg of p-methoxybenzyl 7β-[(Z)-2-(2-tritylamino-4-thizolyl)-2-[[(R S)-(diphenylmethoxycarbonyl)(3,4-diacetoxyphenyl)methoxyimino]acetamido]-3-(isothiazol-3-yl)oxymethyl-3-cephem-4-carboxylate.

NMR spectrum (CDCl$_3$): δ(ppm); 2.26 and 2.28(each s, 3H,

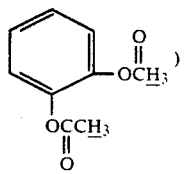
)

3.28–3.50(broad, 2H,

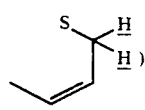
)

3.80(S, 3H,

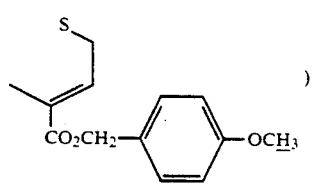
)

4.60(s, 2H,

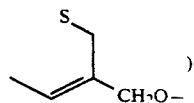
)

4.85–4.96(d×2, 1H, at 6 position) 5.10 and 5.16(s×2, 1H,

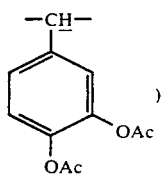

5.24(s,2H,

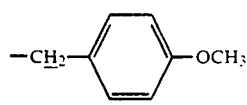

5.6–5.9(m, 1H, at 7 position) 6.5–8.1(m, 37H,

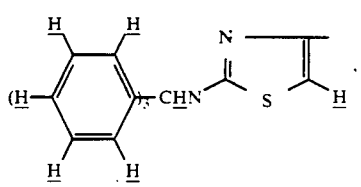

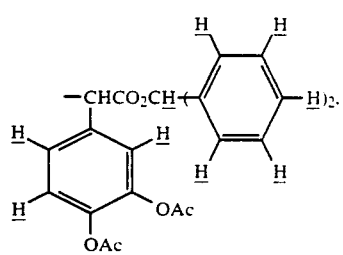

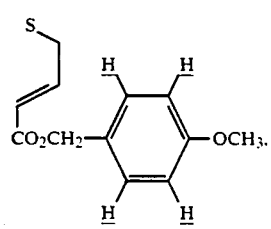

—CONH— and

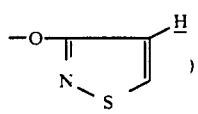

8.40(d, 1H,

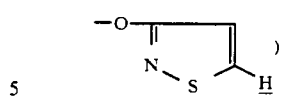

Mass spectrum (FAD Pos.): 1261(M+1)
IR spectrum $\nu_{max}^{KBr}$ (cm$^{-1}$):1784, 1696, 1520.

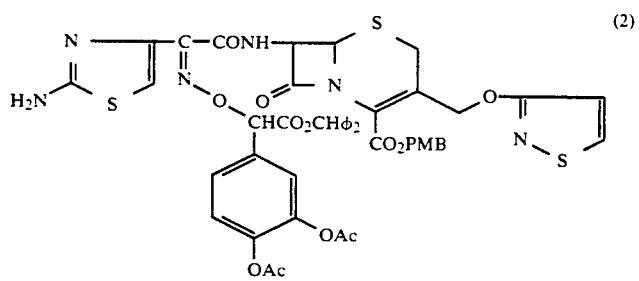 (2)

216 mg of p-methoxybenzyl 7β-[(Z)-2-(tritylamino-4-thiazolyl)-2[[(R  S)-(diphenylmethoxycarbonyl)(3,4-diacetoxyphenyl)methoxyimino]acetamido]-3-(isothiazol-3-yl)oxymethyl-3-cephem-4-carboxylate was dissolved in 8 ml of methylene chloride and 24 ml of 80% acetic acid was added, and then stirred for 3 hrs. at 35° C.

After completion of the reaction, the solvent was evaporated under the reduced pressure and to the resultant residue was added 25 ml of ether, then 50 ml of n-hexane and stirred for 10 min.

The extracted precipitate was collected by filtration and dried over phosphorus pentoxide under the reduced pressure to give 140 mg of p-methoxybenzyl 7β[(Z)-2-[2-amino-4-thiazolyl)-2-[[(R  S)-diphenylmethoxycarbonyl)(3,4-diacetoxyphenyl)methoxyimino]acetamido]-3-(isothiazol-3-yl)oxymethyl-3-cephem-carboxylate.

NMR spectrum (CDCl$_3$): δ(ppm); 2.24(s, 6H,

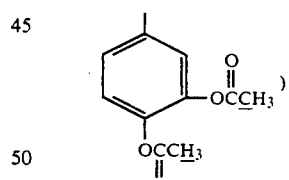

3.30–3.65(broad, 2H,

3.78(s, 3H,

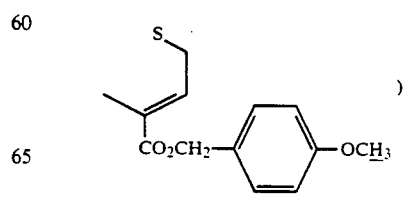

4.84–5.9(m, 7H,

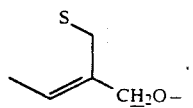

at 6 position,

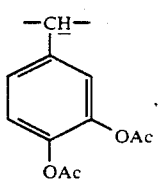

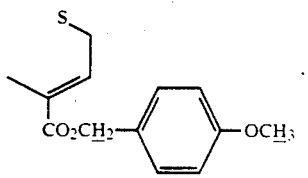

at 7 position) 6.5-7.8(m, 23H,

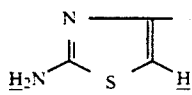

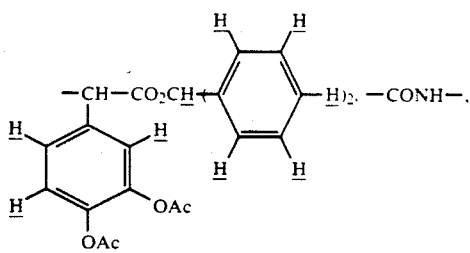

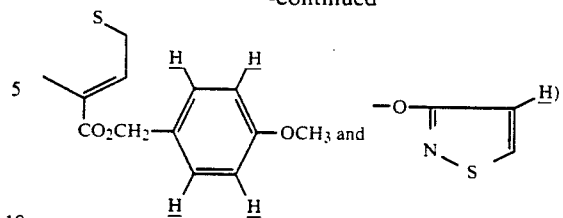 and 8.40(d, 1H,

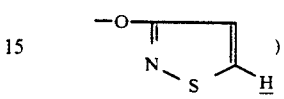)

Mass spectrum FAB (Pos.):1019(M+1).
IR spectrum $\nu_{max}^{KBr}$ (cm$^{-1}$):1780. 1692, 1618, 1522.

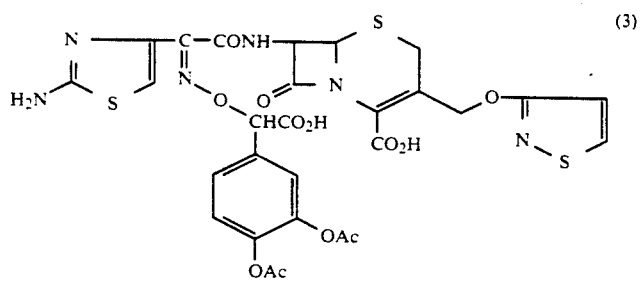

135 mg of p-methoxybenzyl 7β-[(Z)-2-(2-amino-4-thiazolyl)-2-[[(R S)-(diphenylmethoxycarbonyl)(3,4-diacetoxyphenyl)methoxyimino]acetamido]-3-(isothiazol-3-yl)oxymethyl-3-cephem-4-carboxylate was dissolved in 8 ml of methylene chloride and 1 ml of anisole, and to this solution was added dropwise 2.5 ml of trifluoroacetic acid under ice-cooling and then stirred for 25 min. at the same temperature.

After completion of the reaction, the mixture was cooled to 31 50° C. and 10 ml of ether and then 40 ml of n-hexane were added and stirred for 15 min. at −20° C. to −10° C.

The resultant precipitate was collected by filtration and dried over phosphorus pentoxide under the reduced pressure to give 104 mg of 7β-[(Z)-2-(2-amino-4-thiazolyl)-2-[[(R S)-(carboxy)(3,4-diacetoxyphenyl)methoxyimino]acetamido]-3-(isothiazol-3-yl)oxymethyl-3-cephem-4-carboxylic acid.

IR spectrum $\nu_{max}^{KBr}$ (cm$^{-1}$); 1778, 1684, 1644.

EXAMPLE 36

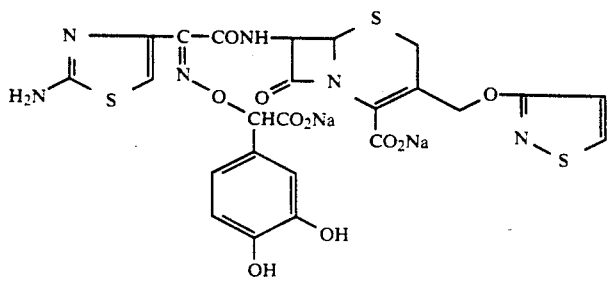

To 83 mg of 7β-[(Z)-2-(2-amino-4-thiazolyl)-2-[[(R S)-(carboxy)(3,4-diacetoxyphenyl)methoxyimino]acetamido]-3-(isothiazol-3-yl)oxymethyl-3-cephem-4-carboxylic acid was added 30 ml of water and 2.4 g of sodium hydrogen carbonate and the mixture was stirred for 4.5 hrs. at the room temperature.

After completion of the reaction, the solution was subjected to column chromatography on Diaion HP-20 and eluted with 20% methanolic aqueous solution and the fractions containing the desired product were combined, concentrated and lyophilized to give 43 mg of disodium 7β-[(Z)-2-(2-amino-4-thiazolyl)-2-[[(R S)-carboxy)(3,4-dihydroxyphenyl)methoxyimino]acetamido]-3-(isothiazol-3-yl)oxymethyl-3-cephem-4-carboxylate.

NMR spectrum (DMSO-d$_6$):δ(ppm); 3.4–3.8(broad, 2H,

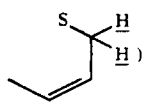

4.94–5.68(m, 5H,

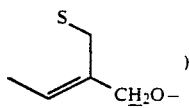

at 6 position,

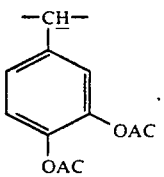

at 7 position) 6.54–6.90(m, 5H,

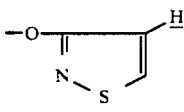

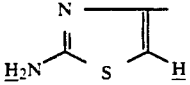

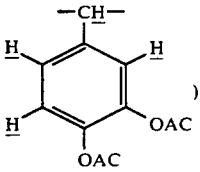

7.12(s, 2H,

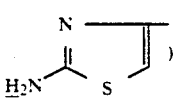

8.84(d, 1H,

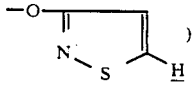

IR spectrum $\nu_{max}^{KBr}$(cm$^{-1}$): 1764, 1670, 1606, 1534.

EXAMPLE 37

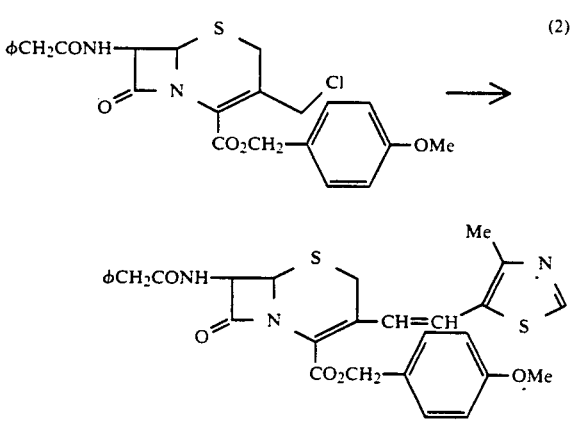

In 35 ml of dimethylformamide 5.0 g (10.3 mmol) of 4-methoxybenzyl 7β-phenylacetamido-3-chloromethyl-3-cephem-4-carboxylate and 2.84 g (10.8 mmol) of triphenylphosphine was dissolved, and 1.62 g (10.8 mmol) of sodium iodide was further added at the room temperature and stirred for 2 hrs. The reaction solution was filtrated and the solvent was evaporated and then to the residue was added isopropylether to powder. Among 9.84 g of the powder obtained from the collection by filtration, 7.31 g of the powder was dissolved in 73 ml of methylene chloride and 30.5 ml of 1N aqueous sodium hydroxide solution under ice-cooling. After stirring for 15 min. at the room temperature, the methylene chloride layer was separated. The aqueous layer was further extracted with 37 ml of methylene chloride. The methylene chloride layers were combined and a solution of 20 ml of methylene chloride of 0.97 g (7.63 mmol) of 5-formyl-4-methylthiazole was added under ice-cooling and the reaction was performed for 15 hrs. at the room temperature. The reaction solution was washed with water and saturated saline solution, dried over anhydrous magnesium sulfate and then the solvent was evaporated to give 6.3 g of caramel. This was subjected to silica gel column chromatography and eluted with chloroform to give 4.23 g of 4-methoxybenzyl 7β-phenylacetamido-3-[2-(4-methyl-5-thiazolyl)vinyl]-3-cephem-4-carboxylate.

NMR spectrum (CDCl$_3$): δ(ppm); 2.40, 2.47(3H, each s,

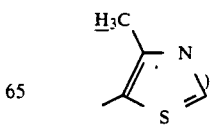

2.84–3.48(2H, m,

3.65(2H, s, —COCH$_2$—), 3.78(3H, s, —OCH$_3$), 5.00, 5.04(2H, each s, —COOCH$_2$—), 5.11, 5.36(1H, each d, CH at 6 position, 5.67, 5.87(1H, each dd, CH at 7 position), 5.83, 6.43(each d,

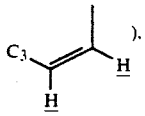

6.76, 6.82, 7.14, 7.22(2H, each d,

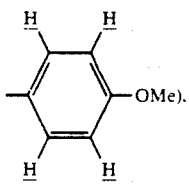

7.20-7.74(6H, m,

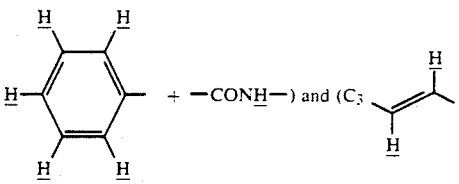

8.47, 8.56(1H, each s,

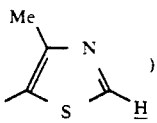

Mass spectrum FAB (Pos.); 562(M+H)$^+$.

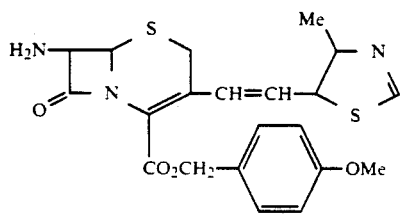

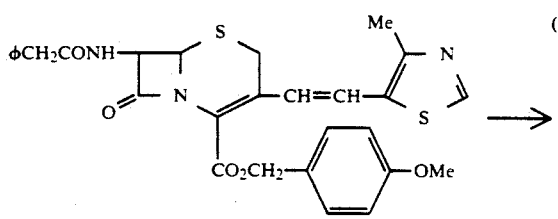

In 70 ml of methylene chloride 4.76 g (22.9 mmol) of phosphorus pentachloride and 6.16 ml (76.2 mmol) of pyridine were dissolved, and a solution of 21 ml of methylene chloride of 4.28 g (7.62 mmol) of 4-methyloxybenzyl 7β-phenylacetamido-3-[2-(4-methyl-5-thizolyl)vinyl]-3-cephem-4-carboxylate was added at −30° C. After stirring for 3 hrs. under ice-cooling, the mixture was added to 70 ml of methanol at −50° C. The reaction was performed for 1 hr. under ice-cooling and then the reaction solution was added to 200 ml of saturated saline solution and 200 ml of methylene chloride under ice-cooling, and stirred for 1 hr. The methylene chloride layer was separated and the aqueous layer was further extracted with methylene chloride. The methylene chloride layers were combined, washed with aqueous saturated sodium hydrogen carbonate solution and dried over anhydrous magnesium sulfate and then, the solvent was evaporated to give 7.0 g of caramel. This was subjected to silicate gel column chromatography and eluted with chloroform to give 626 mg of 4-methoxybenzyl 7β-amino-3-[2-(3-methyl-5-thiazolyl)-vinyl]-3-cephem-4-carboxylate.

NMR spectrum (CDCl$_3$): δ(ppm); 1.67 (2H, brs, —NH$_2$), 2.42, 2.49(3H, each s,

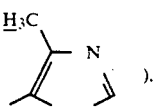

3.22-3.67(2H, m,

3.80(3H, s, —OCH$_3$), 4.80-5.36(4H, m, CH at 6 position +CH+—COOOCH$_2$— at 7 position), 6.31, 6.58(each d,

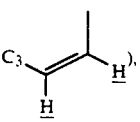

6.75-6.91, 7.13-7.38(4H, m,

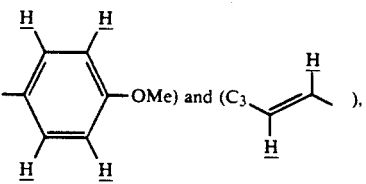

8.50, 8.58(1H, each s,

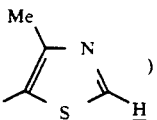

Mass spectrum FAB (Pos.); 444(M+H)$^+$.

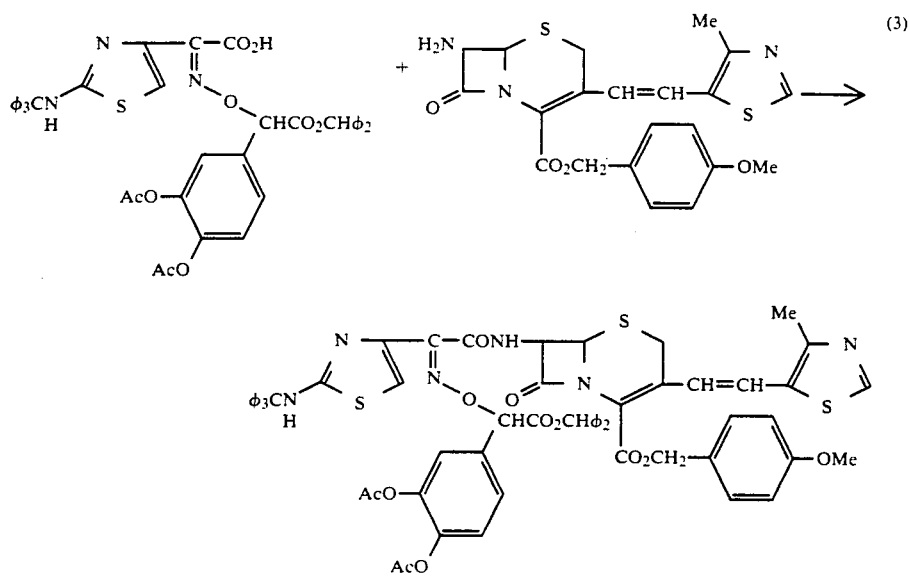

In 5.8 ml of methylene chloride 1.167 g (1.38 mmol) of (Z)-2-(2-tritylamino-4-thiazolyl)-2-[diphenylmethoxycarbonyl(3,4-diacetoxyphenyl)methoxy]iminoacetic acid and 302 mg (1.45 mmol) of phosphorus pentachloride were dissolved under ice-cooling and the reaction was performed for 30 min. This solution was added to a solution of 610 mg (1.38 mmol) of 4-methoxybenzyl 7β-amino-3-[2-(4-methyl-5-thizolyl)vinyl]-3-cephem-4-carboxylate and 0.558 ml (6.9 mmol) of pyridine in 18 ml of methylene chloride at −55° C. and then the reaction temperature was raised to −30° C. over 90 min and the reaction was performed. Then 6.9 ml of 1N hydrochloric acid was added at −30° C. To the reaction solution was added water and extracted with methylene chloride (×3). The methylene chloride layers were combined, washed with saturated saline solution and dried over anhydrous magnesium sulfate, and then the solvent was evaporated to give 2.3 of carmel. This was subjected to silica gel column chromatagraphy and eluted with chloroformethyl acetate to give 729 mg of 4-methoxybenzyl 7β-[(Z)-2-(2-tritylamino-4-thiazolyl)-2-[(R    S)-dipheylmethoxycarbonyl)(3,4-diacetoxyphenyl)methoxyl]imino]acetamido]-3-[2-(4-methyl-5-thiazolyl)vinyl]-3-cephem-4-carboxylate.

NMR spectrum (CDCl$_3$) δ(ppm); 2.20, 2.24, 2.26, 2.29(6H, each s, —OCO—C$\underline{H}_3$), 2.41, 2.42, 2.51, 2.53(3H, each s, 2.88–3.50(2H, m, 3.78, 3.80(3H, each s, —OC$\underline{H}_3$), 4.92, 4.99, 5.03, 5.07(1H, each d, C$\underline{H}$ at 6 position), 5.10, 5.13(2H, each s, —COOC$\underline{H}_2$—), 5.75–5.93(1H, m, C$\underline{H}$ at 7 position), 6.01, 6.10(1H, each s, >C$\underline{H}$—CO$_2$—), 6.25, 6.31, 6.54, 6.56(each d, 6.75–7.45(35H, m,

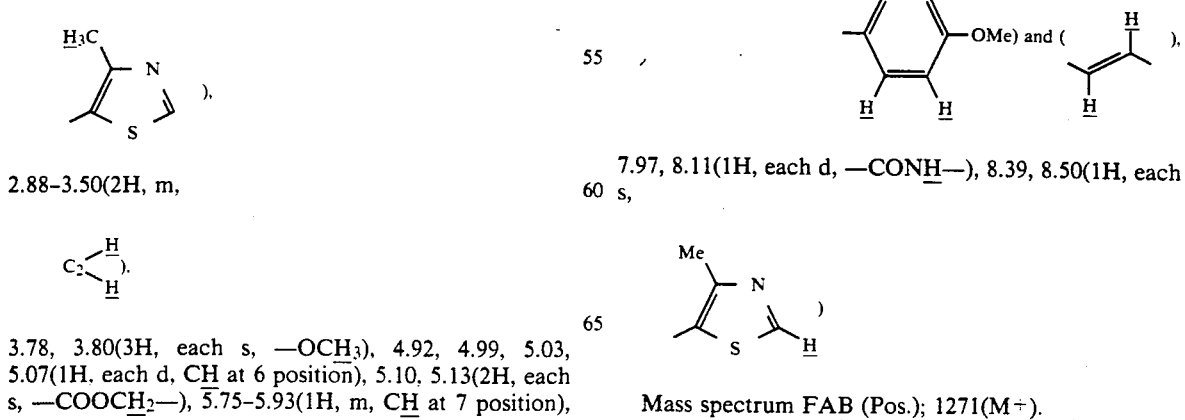

7.97, 8.11(1H, each d, —CON$\underline{H}$—), 8.39, 8.50(1H, each s,

Mass spectrum FAB (Pos.); 1271(M+).

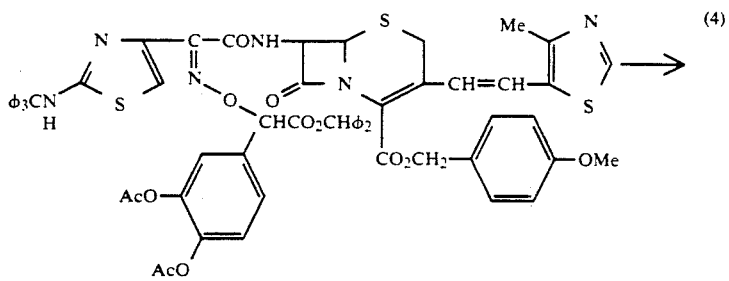

(4)

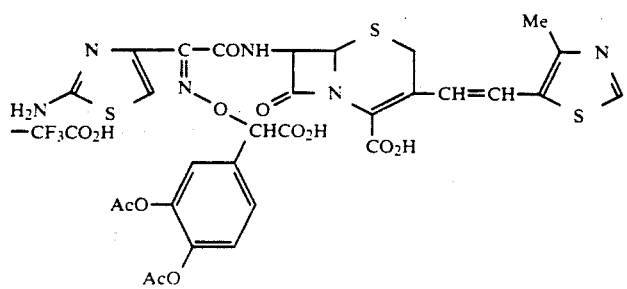

709 mg (0.558 mmol) of 4-methoxybenzyl 7β-[(Z)-2-(2-tritylamino-4-thiazolyl)-2-[[(R S)-(diphenylmethoxycarbonyl)(3,4-diacetoxyphenyl)methoxyl]imino]acetamido]-3-[2-(4-methyl-5-thiazolyl)vinyl]-3-cephem-4-carboylate was dissolved in 7 ml of methylene chloride and 2.8 ml of anisole and then 11.2 ml of trifluoroacetic acid was added under and then 11.2 ml of trifluoroacetic acid was added under ice-cooling and the reaction was performed for 90 min. Methylene chloride and trifluoroacetic acid were evaporated under the reduced pressure and the resultant residue was powdered with ethyl ether-hexane(1:1). The powder collected by filtration was further dissolved in 40 ml of trifluoroacetic acid under ice-cooling and then 10 ml of water was added and the reaction was performed for 2.5 hrs. at the room temperature. Trifluoroacetic acid and water were evaporated under the reduced pressure and to the resultant residue was added ethyl ether to powder and collected by filtration to give 298 mg of 7β-[(Z)-2-(2-amino-4-thiazolyl)-2[[(R S)-carboxy)(3,4-diacetoxyphenyl)methoxy]imino]acetamido]-3-[2-(4-methyl-5-thiazolyl)vinyl]-3-cephem-4-carboxylic acid trifluoroacetate.

NMR spectrum (DMSO-d$_6$): δ(ppm); 2.20-2.44(9H, m, —OCO—C$\underline{H}_3$,

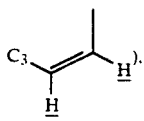

3.22-3.54(2H, m,

5.20-5.32(1H, m, C$\underline{H}$ at 6 position), 5.62(1H, s, >CH—CO$_2$H), 5.78-5.90(1$\underline{H}$, m, C$\underline{H}$ at 7 position), 6.36, 6.40, 6.73, 6.74(each d,

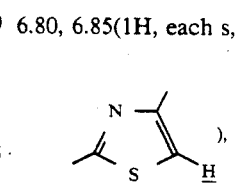

6.80, 6.85(1H, each s,

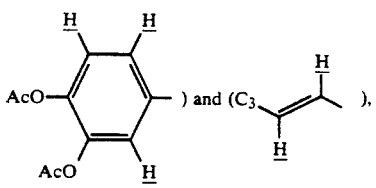

7.16-7.50(3H, m,

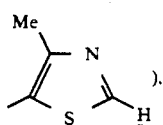

8.94, 8.95(1H, each s, 9.58-9.82(1H, m —CONH—)
Mass spectrum FAB (Pos.);
IR spectrum $\nu_{max}^{KBr}$ (cm$^{-1}$); 1776.

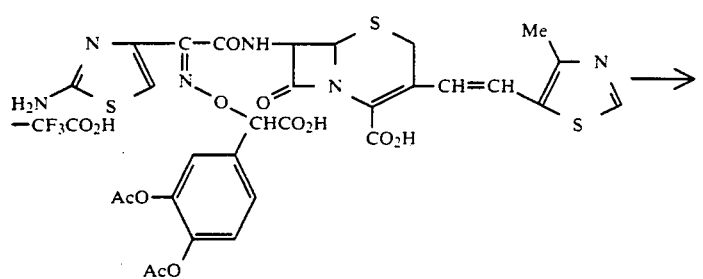

(5)

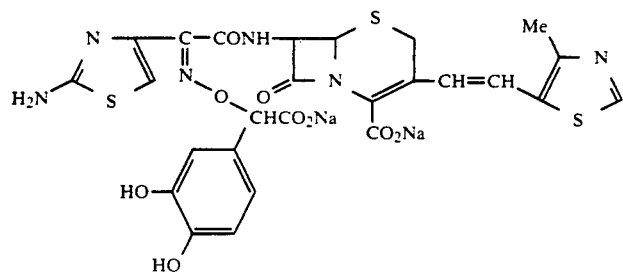

229.3 mg of 7β-[(Z)-2-(2-amino-4-thiazolyl)-2-[[(R S)-(carboxy)(3,4-diacetoxyphenyl)methoxy]imino]acetamido]-3-[2-(4-methyl-5-thiazolyl)vinyl]-3-cephem-4-carboxylic acid trifluoroacetate was dissolved in 23 ml of aqueous saturated sodium hydrogen carbonate solution at the room temperature and the reaction was performed for 4 hrs. and 20 min. The reaction solution was adsorbed on Diaion HP-20 and eluted with water-methanol, and the fractions containing the desired product were collected, concentrated and then lyophilized to give 155 mg of disodium 7β-[(Z)-2-(2-amino)-4-thiazolyl]-2-[[(R S)-(carboxylate)(3,4-dihydroxyphenyl)methoxy]imino]acetamido]-3-[2-(4-methyl-5-thiazolyl)vinyl]-3-cephem-4-carboxylate.

NMR spectrum (D$_2$O) δ(ppm); 2.42, 2.44, 2.48(3H, each s,

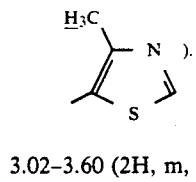

3.02–3.60 (2H, m,

C$_2$<$^H_H$), 5.36–5.50(2H, m, CH+>CH—COO$^\gamma$ at 6 position), 5.70–5.82(1H, m, C$\underline{H}$ at 7 position), 6.34, 6.48(each d, C$_3$—$\underset{\underline{H}}{\overset{H}{\diagup}}$ ), 6.64–7.12(4H, m,

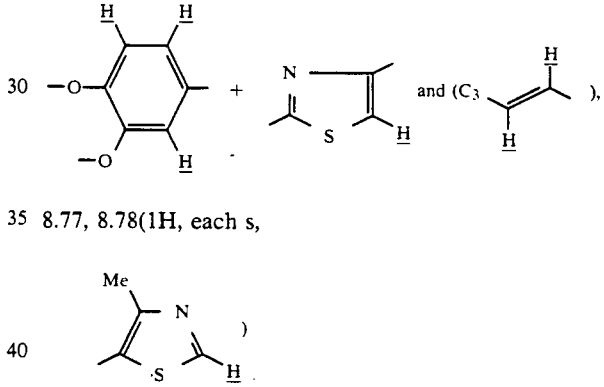

8.77, 8.78(1H, each s,

Mass spectrum FAB (Pos.); 703 (M+H)$^+$.
IR spectrum $\nu_{max}^{KBr}$ (cm$^{-1}$); 1764.

EXAMPLE 38

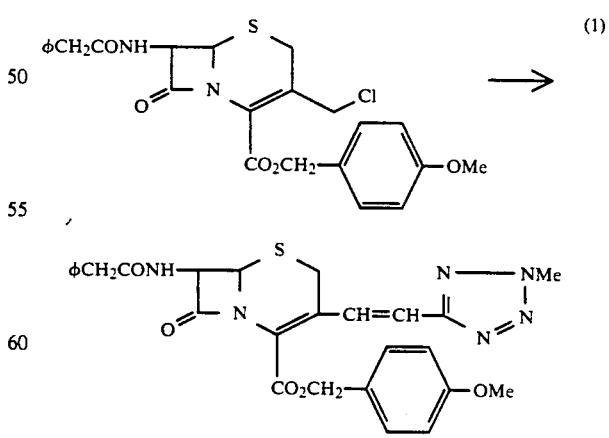

In 35 ml of dimethylformamide 5.0 g (10.3 mmol) of 4-methoxybenzyl 7β-phenylacetamido-3-chloromethyl-3-cephem-4-carboxylate and 2.84 g (10.8 mmol) of triphenylphosphine were dissolved, and 1.62 g (10.8 mmol) of sodium iodide was further added at the room temperature and stirred for 2 hrs. The reaction solution was collected by filtration and the solvent was evaporated and then to the residue was added isopropyl ether to powder. Among 9.68 g of the powder obtained from the collection by filtration, 4.64 g of the powder was dissolved in 44 ml of methylene chloride, and 16 ml of 1N aqueous sodium hydroxide solution was added under ice-cooling. After being stirred for 15 min. at the room temperature, the methylene chloride layer was separated. The aqueous layer was extracted with 5 ml of methylene chloride (×2). The methylene chloride layers were combined, and a solution of 5 ml of methylene chloride of 486 mg (4.34 mmol) of 2-methyl-5-formyl-tetrazole was added under ice-cooling and the reaction was performed for 15 hrs. The reaction solution was washed with 20 ml of water (×2) and further 20 ml of saturated saline solution (×1) and dried over anhydrous magnesium sulfate. The solvent was evaporated to give 3.98 g of carmel. This was subjected to silica gel column chromatography and eluted with chloroform-ethyl acetate to give 3.28 g of a composition of 4-methoxybenzyl 7β-phenylacetamido-3-[2-(2-methyl-5-tetrazolyl)vinyl]-3-cephem-4-carboxylate.

NMR spectrum (DMSO-d$_6$) δ(ppm); 3.5–3.7(4H, m,

—COCH$_2$—), 3.74(3H, S, —OCH$_3$, 4.29, 4.31(3H, each s, >NCH$_3$) 4.96, 5.16(1H, each d, CH at 6 position), 5.05, 5.11(2H, AB pattern, —COOCH$_2$—), 5.44, 5.76(1H, each dd, CH at 7 position), 6.33, 6.44, 6.85, 7.15(2H, each d,

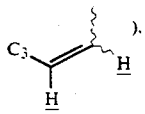

6.11, 6.83, 6.90, 7.28(4H, each d,

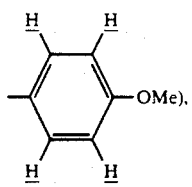

7.2–7.7(5H, m,

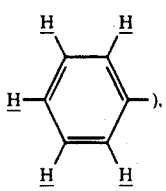

9.18(1H, d, —CONH—).
Mass spectrum FAB (Pos.) 547(M+H)$^+$.
IR spectrum $\nu_{max}^{KBr}$ (cm$^{-1}$); 1784.

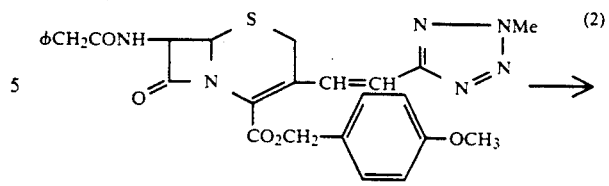

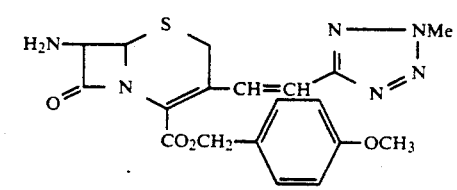

In 50 ml of methylene chloride 3.67 g (17.6 mmol) of phosphorus pentachloride and 4.7 ml (59 mmol) of pyridine were dissolved, and a solution of 10 ml of methylene chloride 3.21 g (5.87 mmol) of 4-methoxybenzyl 7β-phenylacetamido-3-[2-(2-methyl-5-tetrazolyl)vinyl]-3-cephem-4-carboxylate was added at −30° C. After stirring for 4 hrs. under ice-cooling, the mixture was added to 50 ml of methanol at −40° C. After stirring for 1 hr. under ice-cooling, the reaction solution was added to 100 ml of saturated saline solution and 100 ml of methylene chloride under ice-cooling and stirred for 1 hr. The methylene chloride layer was separated and the aqueous layer was further extracted with 50 ml of methylene chloride (×2). The methylene chloride layers were combined, washed with of 50 ml of aqueous saturated sodium hydrogen carbonate solution (×1), dried over anhydrous magnesium sulfate and then, the solvent was evaporated to give 4.8 g of carmel. This was dissolved in methylene chloride and subjected to silica gel column chromatography eluting with ethyl acetate to give 0.63 g of 4-methoxybenzyl 7β-amino-3-[2-(2-methyl-5-tetrazolyl)vinyl-3-cephem-4-carboxylate.

NMR spectrum (DMSO-d$_6$) δ(ppm); 2.32(2H, brs, —NH$_2$) 3.52, 3.65(2H, AB pattern,

3.75(3H, s, —OCH$_3$), 4.30(3H, s, >NCH$_3$), 4.84(1H, d, CH at 6 position), 5.01, 5.08(2H, AB pattern, —COOCH$_2$—), 5.06(1H, d, CH at 7 position) 6.57, 6.77(2H, each d,

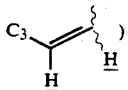

6.89, 7.26(4H, AB pattern,

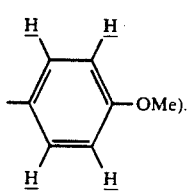

Mass spectrum FAB (Pos.); 429 (M+H)$^+$.
IR spectrum $\nu_{max}^{KBr}$ (cm$^{-1}$); 1778.

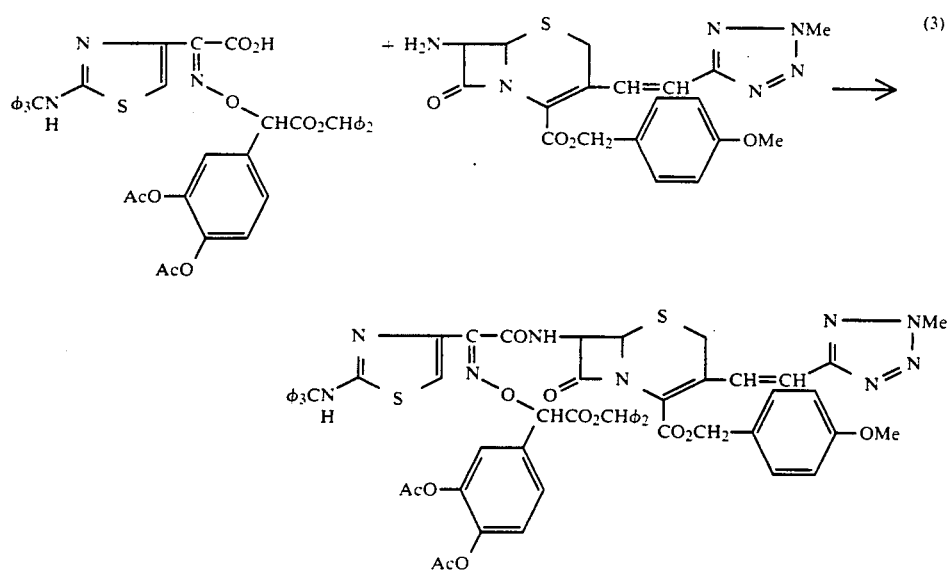

In 15 ml of methylene chloride 1.17 g (1.38 mmol) of (Z)-2-(2-tritylamino-4-thiazoyl)-2-[diphenylmethyoxycarbonyl (3,4-diacetoxyphenyl)methoxy]iminoacetic acid was dissolved and 287 mg (1.38 mmol) of phosphorus pentachloride was added at −5° C. and the reaction was performed for 30 min. This solution was added to a solution of 590 mg (1.38 mmol) of 4-methoxybenzyl 7β-amino-3-[2-(2-methyl-5-tetrazolyl)vinyl]-3-cephem-4-carboxylate and 0.56 ml (6.9 mmol) of pyridine in 15 ml of methylene chloride at −70° C. and then the reaction was performed for 30 min. at −30° C. To the reactant was added 400 ml of ethyl acetate and washed with 20 ml of water (×1) and 20 ml of saturated saline solution (×1), and then dried over anhydrous magnesium sulfate and the solvent was evaporated to give 1.89 g of caramel. This was dissolved in chloroform and subjected to silica gel column chromatography eluting with chloroform-ethyl acetate(4:1) to give 103 g of 4-methoxybenzyl 7β-[(Z)-2-(2-tritylamino-4-thiazoyl)-2-[[(R S)-(Diphenylmethoxycarbonyl)(3,4-diacetoxyphenyl)methoxyl]imino]acetoamido]-3-[2-(2-methyl-5-tetrazolyl]vinyl]-3-cephem-4-carboxylate.

NMR spectrum (DMSO-d$_6$) δ(ppm); 2.23, 2.24, 2.25, 2.26(6H, each s, —OCOC$\underline{H}_3$), 3.3-3.7(2H, m,

3.72, 3.73(3H, each s, —OCH$_3$), 4.26(3H, s, >NCH$_3$), 5.0-5.2(2H, m, —COOC$\underline{H}_2$φ), 5.13, 5.17(1H, each d, C$\underline{H}$ at 6 position), 5.68, 5.76(1H, each dd, C$\underline{H}$ at 7 position), 5.86(1H, d, >C$\underline{H}$—CO$_2$—). 5.57, 5.61, 5.76, 6.79(2H, each d,

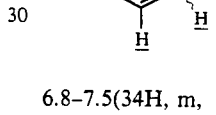

6.8-7.5(34H, m,

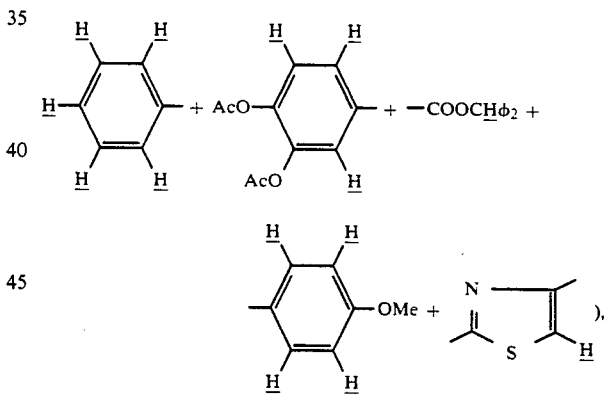

8.91(1H, s, φ$_3$CN$\underline{H}$—) 9.63, 9.76(1H, each d, —CON$\underline{H}$—).

Mass spectrum FAB (Pos.); 1256(M+H)$^+$. IR spectrum $\mu_{max}^{KBr}$(cm$^{-1}$); 1780.

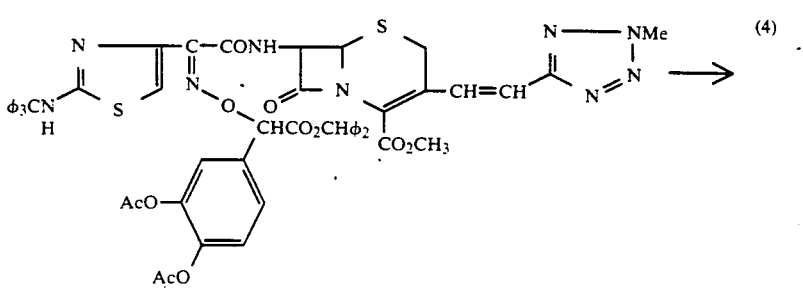

-continued

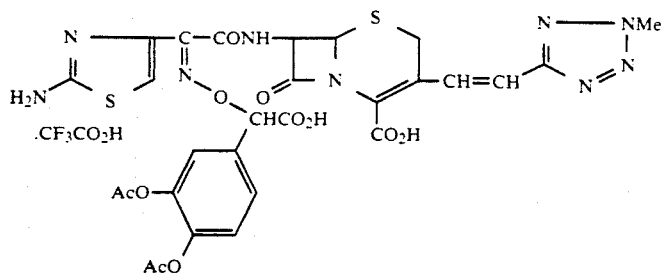

990 mg (0.789 mmol) of 4-methoxybenzyl 7β-[(Z)-2-(2-trit 1-amino-4-thiazoyl)-2-[[(R,S)-diphenylmethoxycarbonyl)(3,4-diacetoxyphenyl)methoxy]imino]acetamido[-3-[2-(2-methyl-5-tetrazoyl]vinyl]-3-cephem-4-carboxylate was dissolved in 10 ml of methylene chloride and 0.7 ml of anisole, and then 7 ml of trifluoroacetic acid was added under ice-cooling and the reaction was performed for 1 hr. at the room temperature Methylene chloride and trifluoroactic acid were evaporated under the reduced pressure and the resultant residue was dissolved again in 10 ml of trifluoroacetic acid and 7ml of water was added in 10 ml of trifluoroacetic acid and 7 ml of water was added and the reaction was performed for 2 hrs. at the room temperature. Trifluoroacetic acid and water were evaporated and to the resultant residue was added ethyl ether to powder and collected by filtration to give 603 mg of β-[(Z)-2-(2-amino-4-thiazolyl)-2-[[R.S)-(carboxy)(3,4-diacetoxyphenyl)methoxy]imino]acetamido]-3-[2-(2-methyl-5-tetrazolyl)vinyl]-3-cephem-4-carboxylacid trifluoroacetate.

NMR spectrum (DMSO-d₆) δ(ppm); 2.23, 2.50, 2.50, 2.51(6H, each s, —OCOC$\underline{H}$₃), 3.3–3.7(2H, m,

), 4.32(3H, s, >NC$\underline{H}$₃), 5.20, 5.21(1H, each d, CH at 6 position), 5.55, 5.57(1H, each s, >C$\underline{H}$—CO₂H), 5.7–5.9(1H, m, C$\underline{H}$ at 7 position), 6.60, 6.80(2H, each d,

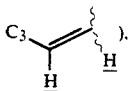

6.88, 6.91(1H, each d,

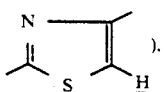), 7.2–7.5(3H, m,

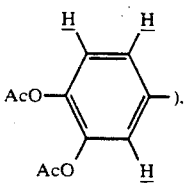), 9.7–10.1(1H, m, —CON$\underline{H}$—).
Mass spectrum FAB (Pos.); 728(M+H)⁺.
IR spectrum $\nu_{max}^{KBr}$ (cm⁻¹); 1774.

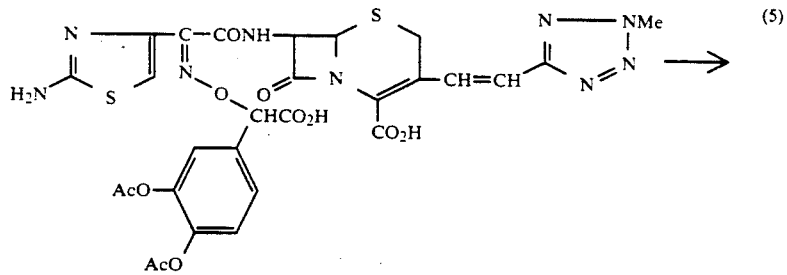

(5)

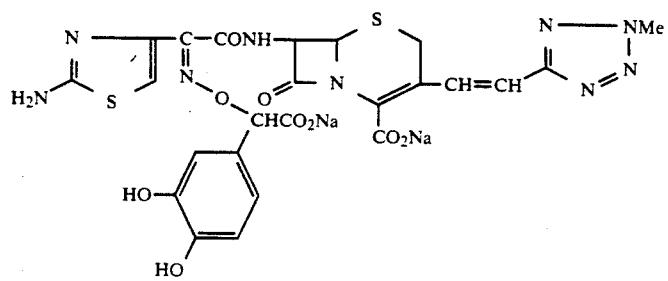

406 mg of 7β-[(Z)-2-(2-amino-4-thiazoyl)-2[[(R S)-(carboxy)(3,4-diacetoxyphenyl)methoxy]imino]acetamido]-3-[2-(2-methyl-5-tetrazolyl)vinyl]-3-cephem-4-carboxylic acid trifluoroacetate was dissolved in 100 ml of saturated sodium hydrogen carbonate at the room temperature and the reaction was performed for 3 hrs. at the room temperature. The reaction solution was adsorbed on Diaion HP-20 and eluted with water-methanol and the fractions containing the desired product were collected, concentrated and then lyophilized to give 177 mg of disodium 7β-[(Z)-2-(2-amino-4-thiazolyl)-2-[[(R S)-(carboxylate)(3,4-dihydroxyphenyl)methoxy]imino]acetamido]-3-[2-(2-methyl-5-tetrazolyl)vinyl]-3-cephem-4-carboxylate.

NMR spectrum (D₂O) δ(ppm); 3.0–3.7(2H, m,

4.36, 4.37(3H, each s, >NCH₃), 5.18, 5.19(1H, each d, CH at 6 position), 5.42(1H, s, >CH—COO⊖), 5.70, 5.75(1H, each d, CH at 7 position), 6.5–7.1(6H, m,

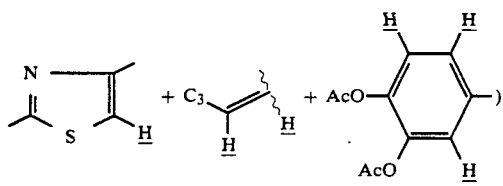

Mass spectrum FAB (Pos.); 688(M+H)⁺.
IR spectrum $\nu_{max}^{KBr}$ (cm⁻¹); 1770.

—OCH₃) 5.00(2H, —COOCH₂—) 5.20(1H, d, CH at 6 position) 5.78(1H, dd, CH at 7 position) 6.69, 6.91(each 1H, each of d,

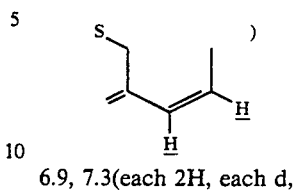

6.9, 7.3(each 2H, each d,

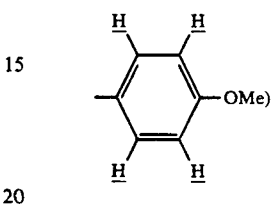

9.05(1H, s,

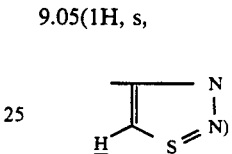

9.20(1H, d, CONH).
Mass Spectrum FAB (Pos.); 549(M+H)⁺.
IR spectrum $\nu_{max}^{KBr}$ (cm⁻¹); 1772.

EXAMPLE 39

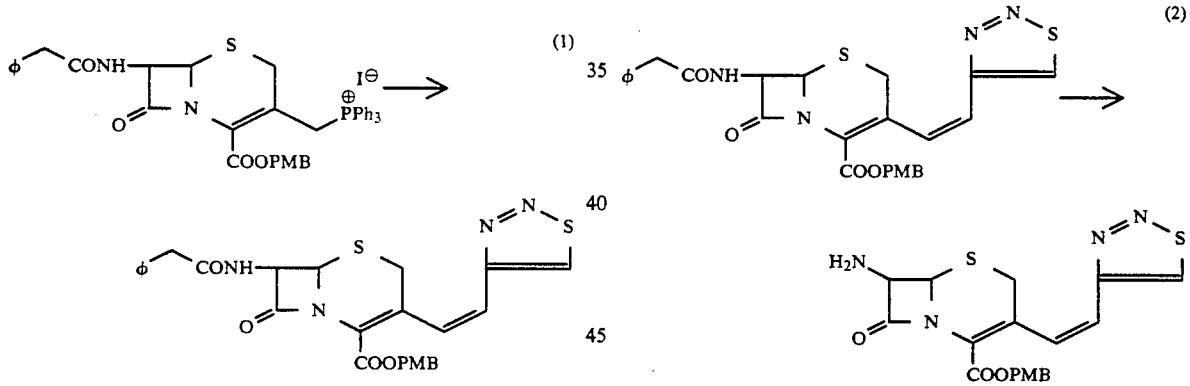

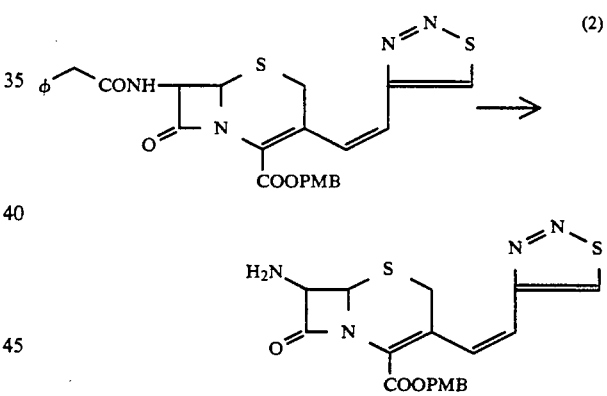

160 ml of methylene chloride and 70 ml of in aqueous sodium hydroxide solution were mixed and to the mixture was added 15 g of [(p-methoxybenzyl 7β-phenylacetamido-3-cephem-4-carboxylate]-3-yl]methyltriphenylphosphonium iodide with stirring. After stirring for 15 min, the organic layer was separated and dried over anhydrous magnesium sulfate. The drying agent was evaporated from the solution and to the solution was added a solution of methylene chloride of 2.00 g of 4-formyl-1,2,3-thiadiazole and the reaction was performed for 4 hrs. at the room temperature. The reaction solution was concentrated under the reduced pressure and then subjected to silica gel column chromatography eluting with methylene chloride:ethyl acetate=9:1. The fractions containing the desired product were collected, concentrated, and powdered with n-pentane to give 7.40 g of p-methoxybenzyl 7β-phenylacetamido-3-[2-(Z)(1,2,3-thiazol-4-yl)vinyl]-3-cephem-4-carboxylate.

NMR spectrum (DMSO-d₆) δ(ppm); 3.34(2H, s, φCH₂CO) 3.4–3.75(2H, m, CH at 2 position) 3.77(3H, s, In 15 ml of methylene chloride 1.25 g of phosphorus pentachloride and 1.58 g of pyridine were dissolved, and 1.10 g of p-methoxybenzyl 7β-phenylacetamido-3-[2-(Z)-(1,2,3-thiadiazol-4-yl)vinyl]-3-cephem-4-carboxylate was added simultaneously with 5 ml of methylene chloride at −30° C. After stirring for 4 hrs. under ice-cooling, to the mixture was added 15 ml of methanol at −30° C. The mixture was stirred for 30 min. at 4° C., and then 30 ml of saturated saline solution was added and stirred for 14 hours. The reaction solution was separated and the organic layer was washed with aqueous saturated sodium hydrogen carbonate solution, dried over anhydrous magnesium sulfate and then the solvent was evaporated to give the crude product. This was subject to silica gel column chromatography eluting with methylene chloride:ethyl acetate=3:1 to give 503 mg of p-methoxybenzyl 7β-amino-3-[2-(Z)-(1,2,3-thiazol-4-yl)vinyl]-3-cephem-4-carboxylate.

NMR spectrum (CDCl₃) δ(ppm); 1.88(2H, bs, NH₂) 3.23, 3.62(each 1H, d,

3.92(3H, s,

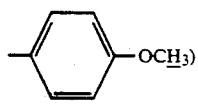

4.79(1H, d, CH at 6 position) 5.02(1H, d, CH at 7 position) 5.10–5.14(2H, dd,

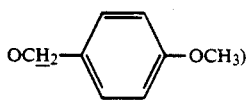

6.73, 6.90(each 1H, d,

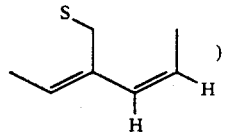

Mass spectrum FAB (Pos.); 431(M+H)+. IR spectrum $\nu_{max}^{KBr}$ (cm$^{-1}$); 1778.

phenylmethoxy]imino]acetamido]-3-[2-(Z)-(1,2,3-thiazol-4-yl)vinyl]-3-cephem-4-carboxylate.

NMR spectrum (DMSO-d$_6$), δ(ppm); 2.25, 2.51(each 3H, each s,

3.2–3.6(2H, m

3.74(3H, s,

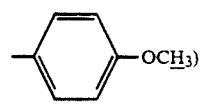

5.00, 5.01(2H, each s,

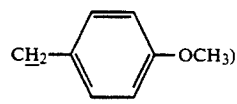

5.20, 5.25(1H, each d, CH at 6 position) 5.69, 5.77(1H, each dd, CH at 7 position) 5.89, 5.87(1H, each s,

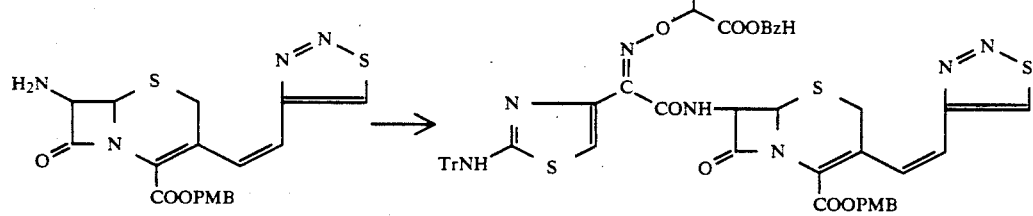

To 4 ml of methylene chloride were added 931 mg of (Z)-2-(2-tritylamino-4-thiazolyl)-2-[diphenylmethoxycarbonyl-(3,4-diacetoxyphenyl)methoxy]iminoacetic acid and 229 mg of phosphorus pentachloride at −20° C. and the mixture was stirred for 30 min. This solution was added to a solution of 474 mg of p-methoxybenzyl 7β-amino-3-[2-(Z)-(1,2,3-thiazol-4-yl)vinyl]-3-cephem-4-carboxylate and 552 mg of pyridine in 10 ml of methylene chloride at −70° C. The reaction solution was warmed to −30° C. and again cooled to −70° C., 3 ml of 1N-hydrochloric acid was added. The reaction solution was separated and the organic layer was washed with 1N hydrochlonic acid, saturated saline solution and then dried over anhydrous magnesium sulfate. The solvent was evaporated and the resultant residue was subjected to silica gel column chromatography eluting with methylene:ethyl acetate=9:1 to give 719 mg of p-methoxybenzyl 7β-[(Z)-2-(2-trityl-amino-4-thiazolyl)-2-[[(R　S)-(diphenylmethoxycarbonyl)-(3,4-diacetoxy- >CHCO$_2$—) 6.6–7.0,(36H, m,

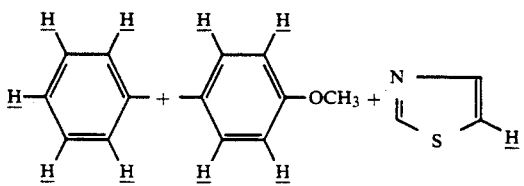

7.1–7.5

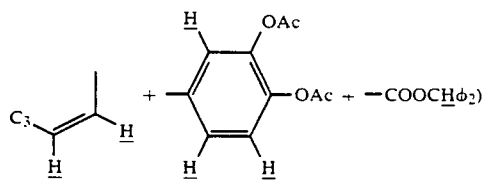

8.97, 8.99(1H, each s,

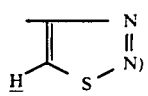

9.65, 9.77(1H, each d, CONH)
Mass spectrum FAB (Pos.); 1285(M+H)+.
IR spectrum $\nu_{max}^{KBr}$ (cm$^{-1}$); 1780.

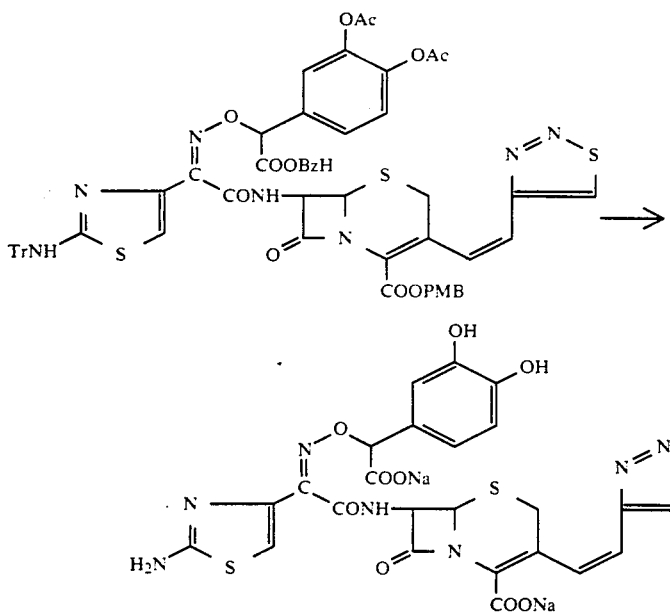

a) 1.70 g of p-methoxybenzyl 7β-[(Z)-2-(2-tritylamino-4-thiazolyl)-2-[[(R S)-diphenylmethoxycarbonyl)(3,4-diacetoxyphenyl)methoxyl-]imino]acetamido]-3-[2-(Z)-(1,2,3-thiazol-4-yl)vinyl]-3-cephem-4-carboxylate was dissolved in 3 ml of methylene chloride and 1.2 ml of anisole, and then 5 ml of trifluoroacetic acid was added under ice-cooling and the reaction was performed for 30 min. Trifluoroacetic acid was evaporated under the reduced pressure and the resultant residue was powdered with ethyl ether. The powder obtained from the collection by filtration was added to 9 ml of trifluoroacetic acid under ice-cooling and then 5 ml of water was added and the reaction was performed for 45 min. at the room temperature. Trifluoroacetic acid and water were evaporated under the reduced pressure and to the resultant residue was added ethyl ether to powder to give 930 mg of crude 7β-[(Z)-2-(2-amino-4-thiazolyl)-2-[[(R S)-carboxy)(3,4-diacetoxyphenyl)methoxy]imino]acetamido]-3-[2-(Z)-(1,2,3-thiadiazol-4-yl)vinyl]-3-cephem-4-carboxylic acid trifluoroacetate.

b) 900 mg of the powder obtained from a) was suspended in 100 ml of water and aqueous saturated sodium hydrogen carbonate solution was added to make pH 8. The reaction was performed for 4 hrs. at the room temperature and then the reaction solution was adsorbed on Diaion HP-20 and eluted with water-methanol. The fractions containing the desired product were collected, concentrated and then lyophilized to give 158 mg of the powder of disodium 7β-[(Z)-2-(2-amino-4-thiazolyl)-2-[[(R S)-carboxylate)(3,4-dihydroxyphenyl)methoxy]acetamido]-3-[2-(Z)-(1,2,3-thiadiazol-4-yl)vinyl]-3-cephem-4-carboxylate.

NMR spectrum (D$_2$O) δ(ppm); 3.97, 4.00, 4.43, 4.46(2H, AB pattern,

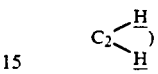

5.17, 5.18(1H, each d, CH at 6 position) 5.40, 5.41(1H, each d, >CHCOO—) 5.70, 5.74(1H, each dd, CH at 7 position) 6.6–7.1(6H, m, (4)

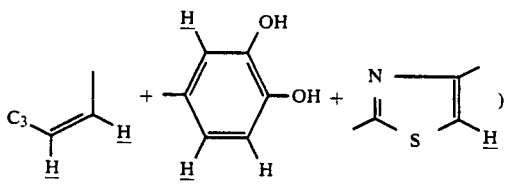

8.77, 8.78(1H, each s,

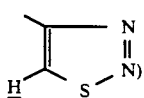

Mass spectrum FAB (Pos.); 690(2 tolium salt+H)+.
IR spectrum $\nu_{max}^{KBr}$ (cm$^{-1}$); 1768.

We claim:
1. A compound of Formula (I) or its salt

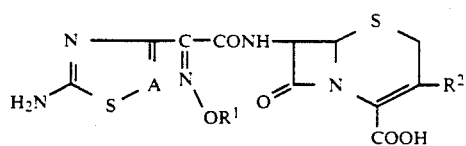  (I)

wherein A represents C or N; $R^2$ is a group represented by

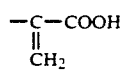

and $R_2$ represents —X—$R_6$, wherein X represents —CH$_2$O—, CH$_2$S—, —CH=CH or —CH=CH—S—, and $R^6$ represents

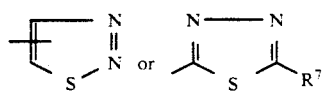

wherein $R^7$ is hydrogen or lower alkyl.

2. A compound of Formula (I) or its salt

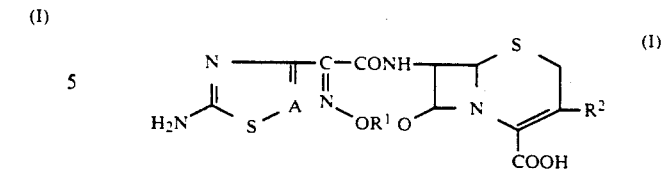  (I)

wherein A represents CH or N; $R^1$ is a group represented by

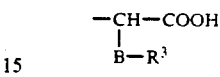

wherein B is a single bond and $R^3$ is thienyl; and $R^2$ represents —X—$R^6$, wherein X represents —CH$_2$O—, —CH$_2$—S—, or —CH=CH—S—, and $R^6$ represents

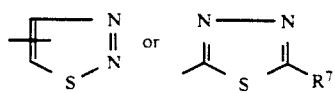

wherein $R^7$ is hydrogen or lower alkyl.

* * * * *